(12) United States Patent
Holtzapple et al.

(10) Patent No.: US 9,017,975 B2
(45) Date of Patent: Apr. 28, 2015

(54) PRODUCTION AND SECRETION OF FATTY ACIDS AND FATTY ACID DERIVATIVES

(71) Applicant: Synthetic Genomics, Inc., La Jolla, CA (US)

(72) Inventors: Erik Holtzapple, San Diego, CA (US); Robert C. Brown, San Diego, CA (US); Rekha Seshadri, San Diego, CA (US); Jennifer Coppersmith, San Diego, CA (US); John Verruto, San Diego, CA (US)

(73) Assignee: Synthetic Genomics, Inc., La Jolla, CA (US)

(*) Notice: Subject to any disclaimer, the term of this patent is extended or adjusted under 35 U.S.C. 154(b) by 0 days.

(21) Appl. No.: 13/629,492

(22) Filed: Sep. 27, 2012

(65) Prior Publication Data

US 2013/0078686 A1    Mar. 28, 2013

Related U.S. Application Data

(60) Provisional application No. 61/539,640, filed on Sep. 27, 2011.

(51) Int. Cl.

| | |
|---|---|
| *C12P 7/04* | (2006.01) |
| *C12P 5/02* | (2006.01) |
| *C12P 7/64* | (2006.01) |
| *C07K 14/21* | (2006.01) |
| *C07K 14/28* | (2006.01) |
| *C12N 9/10* | (2006.01) |
| *C12N 9/02* | (2006.01) |
| *C12N 9/16* | (2006.01) |
| *C12N 9/88* | (2006.01) |
| *C12N 1/21* | (2006.01) |
| *C12N 15/70* | (2006.01) |
| *C12N 15/74* | (2006.01) |

(52) U.S. Cl.
CPC ............ *C12P 7/6409* (2013.01); *C12P 5/02* (2013.01); *C07K 14/28* (2013.01); *C07K 14/21* (2013.01); *C12N 9/88* (2013.01); *C12Y 401/99005* (2013.01); *C12Y 401/01* (2013.01); *C12N 15/70* (2013.01); *C12N 15/74* (2013.01); *C12P 7/04* (2013.01); *C12N 9/1029* (2013.01); *C12Y 203/0102* (2013.01); *C12P 7/6436* (2013.01); *C12Y 203/01075* (2013.01); *C12Y 203/01084* (2013.01); *C12N 9/0008* (2013.01); *C12N 9/16* (2013.01); *C12Y 102/0108* (2013.01); *C12Y 301/0202* (2013.01)

(58) Field of Classification Search
None
See application file for complete search history.

(56) References Cited

U.S. PATENT DOCUMENTS

| | | | |
|---|---|---|---|
| 5,254,466 | A | 10/1993 | Picataggio et al. |
| 5,298,421 | A | 3/1994 | Davies et al. |
| 5,370,996 | A | 12/1994 | Metz et al. |
| 5,403,918 | A | 4/1995 | Metz |
| 5,411,879 | A | 5/1995 | Pollard et al. |
| 5,455,167 | A | 10/1995 | Voelker et al. |
| 5,654,495 | A | 8/1997 | Voelker et al. |
| 6,143,538 | A | 11/2000 | Somerville et al. |
| 6,492,509 | B1 | 12/2002 | Lardizabal et al. |
| 7,118,896 | B2 | 10/2006 | Kalscheuer et al. |
| 2004/0237144 | A1 | 11/2004 | Selvaraj et al. |
| 2009/0148918 | A1 | 6/2009 | Trimbur et al. |
| 2009/0298143 | A1 | 12/2009 | Roessler et al. |
| 2010/0105963 | A1 | 4/2010 | Hu et al. |
| 2010/0151567 | A1 | 6/2010 | Franklin et al. |
| 2010/0170148 | A1 | 7/2010 | Steen et al. |
| 2010/0203614 | A1 | 8/2010 | Wahlen et al. |
| 2011/0000125 | A1* | 1/2011 | McDaniel et al. .............. 44/388 |
| 2011/0008861 | A1 | 1/2011 | Berry et al. |
| 2011/0020883 | A1 | 1/2011 | Roessler et al. |
| 2011/0072714 | A1 | 3/2011 | Gaertner |
| 2011/0111470 | A1* | 5/2011 | Berry et al. ................... 435/134 |
| 2011/0195469 | A1 | 8/2011 | Roessler et al. |
| 2011/0250659 | A1 | 10/2011 | Roberts et al. |

FOREIGN PATENT DOCUMENTS

| | | |
|---|---|---|
| EP | 1 752 532 | 2/2007 |
| WO | WO 2007/136762 | 11/2007 |
| WO | WO 2008/100251 | 8/2008 |
| WO | WO 2008/119082 | 10/2008 |
| WO | WO 2008/130437 | 10/2008 |

(Continued)

OTHER PUBLICATIONS

Barret et al., Genomic analysis of the type VI secretion systems in *Pseudomonas* spp.: novel clusters and putative effectors uncovered, Microbiology, 2011, 157, 1726-39.*

(Continued)

*Primary Examiner* — Rebecca Prouty
*Assistant Examiner* — Todd M Epstein
(74) *Attorney, Agent, or Firm* — DLA Piper LLP (US)

(57) ABSTRACT

The invention relates to acyl-CoA-independent methods of producing fatty alcohols in recombinant host cells engineered to express an alcohol-forming acyl-ACP reductase. The recombinant host cells may be photosynthetic microorganisms, such as cyanobacteria. Isolated nucleic acid molecules, vectors, and recombinant host cells expressing an alcohol-forming acyl-ACP reductase, and systems for producing fatty alcohols via an acyl-CoA-independent pathway, are also provided. Also provided are microorganisms engineered for the secretion of fatty acids and fatty acid derivatives, including fatty alcohols, and methods of producing fatty acid derivatives using such engineering microorganisms.

30 Claims, 18 Drawing Sheets

(56) References Cited

FOREIGN PATENT DOCUMENTS

| | | |
|---|---|---|
| WO | WO 2008/151149 | 12/2008 |
| WO | WO 2009/076559 | 6/2009 |
| WO | WO 2009/111513 | 9/2009 |
| WO | WO 2009/124070 | 10/2009 |
| WO | WO 2010/011754 A2 | 1/2010 |
| WO | WO 2010/033921 | 3/2010 |
| WO | WO 2010/044960 | 4/2010 |
| WO | WO 2010/048568 | 4/2010 |
| WO | WO 2010/006312 | 5/2010 |
| WO | WO 2010/118410 | 10/2010 |
| WO | WO 2010/135624 | 11/2010 |
| WO | WO 2011/008535 | 1/2011 |
| WO | WO 2011/019858 | 2/2011 |
| WO | WO 2011/084647 A2 | 7/2011 |
| WO | WO 2012/087963 | 6/2012 |

OTHER PUBLICATIONS

Bingle et al., Type VI secretion: a beginner's guide, Curr. Opin. Microbiol., 2008, 11, 3-8.*

Cascales et al., Structural biology of the type VI secretion systems, Phil. Trans. R. Soc. B, 2012, 367, 1102-11.*

Leiman et al., Type VI secretion apparatus and phage tail-associated protein complexes share a common evolutionary origin, Proc. Natl. Acad. Sci. USA, 2009, 106, 4154-59.*

D0H6H4_VIBCH, UniProtKB, Dec. 15, 2009 (online). Retrieved Nov. 28, 2012. Retrieved from the internet <URL: http://www.uniprot.org/uniprot/D0H6H4.txt?version=6>.

International Search Report (ISR) from PCT/US2012/57671.

Blondel et al.: "Comparative genomic analysis uncovers 3 novel loci encodind type six secretion systems differentially distributed in Salmonella serotypes"; BMC Genomics 2009, 10:354.

Boyer et al.: "Dissecting the bacterial type VI secretion system by a genome wide in silico analysis: what can be learned from available microbial genomic resources?"; BMC Genomics 2009, 10:104.

Doan et al.: "Functional Expression of five Arabidopsis fatty acyl-CoA reductase cenes in E. coli"; (2009) J. Plant Physiol. 166: 787-796.

Domergue et al.: "Three Arabidopsis Fatty Acyl-CoA Reductases, FAR1, FAR4, and FAR5, Generate Fatty Alcohols Associated with Suberin Deposition"; (2010) Plant Physiol 153: 1539-1554.

Filloux, Alain: "The type VI secretion system: A tubular story"; EMBO Journal (2009) 28, 309-310.

Filloux et al.: "The bacterial type VI secretion machine: yet another player for protein transport across membranes"; Microbiology (2008), 154, 1570-1583.

Gupta et al,: "Expression of the photorhabdus luminescens lux genes (luxA, B, C, D, and E) in Saccharomyces cerevislae"; (2003) FEMS Yeast Res 4: 305-313.

Hachani et al.: "Type VI Secretion System in Pseudomonas aeruginosa Secretion and Multimerization of VgrG Proteins"; J Bio Chem, Apr. 8, 2011, 286:14, 12317-12327.

Hofvander et al.: "A prokaryotic acyl-CoA reductase performing reduction of fatty acyl-CoA to fatty alcohol" FEBS Letters, 2011. 585: 3538-43.

Honsho et al.: Posttranslational regulation of fatty acyl-CoA reductase 1, Far1, controls ether glycerophospholipid synthesis; J. Biol. Chem. 285:8537-8542 (2010).

Kanamaru, Shuji: "Structural similarity of tailed phages and pathogenic bacterial secretion systems"; PNAS Mar. 17; 2009, 106:11, 4067-4068.

Lienard et al.: "Evolution of multicomponent pheromone signals in small ermine moths involves a single fatty-acyl reductase gene"; Proc. Natl. Acad. Sci. 107:10955-10960 (2010).

Maes et al.: "Dissection of the phytohormonal regulation of trichome formation and biosynthesis of the antimalarial compound artemisinin in Artemisia annua plants"; (2011) New Phytol. 189:176-189.

Meighen, E.: "Bacterial bioluminescence: organization, regulation, and application of the lux genes"; (1993) The FASEB Journal 7: 1016-1022.

Metz et al.: "Purification of a Jojoba Embryo Fatty Acyl-Coenzyme A Reductase and Expression of Its cDNA in High Erucic Acid Rapeseed"; (2000) Plant Physiol. 122: 635-644.

Michinaka et al.: Extracellular Secretion of Free Fatty Acids by Disruption of a Fatty Acyl-CoA Synthetase Gene in Saccharomyces cervisiae; (2003) J. Bioscience and Bioengineering 95: 435-440.

Moto; K. et al.: "Pheremone gland-specific fatty-acyl reductase of the silkrnoth, Bombyx mori"; (2003) Proc. Nati. Acad. Sci, USA 100:9156-9161.

Pighin, J.A. et al.: "Plant cuticular lipid export requires an ABC transporter"; (2004) Science 306: 702-704.

Pukatzki et al.: "Type VI secretion system translocates a phage tail spike-like protein into target cells where it cross-links actin"; PNAS, Sep. 25, 2007, 104:39, 15508-15513.

Quintana et al.: "Renewable energy from Cyanobacteria: energy production optimization by metabolic pathway engineering"; (2011) Appl Microbiol Biotechnol 91: 471-490.

Records, Angela R.: "The Typo VI Secretion System: A Multipurpose Delivery System with a Phage-Like Machinery"; MPMI, 24:7, 2011, pp. 751-757.

Reiser et al.: "Isolation of Mutants of Acinetobacter calcoaceticus Deficient in Wax Ester Synthesis and Complementation of One Mutation with a Gene Encoding a Fatty Acyl Coenzyme a Reductase"; (1997) J. Bacteriol. 2969-2975.

Rowland et al.: "CER4 Encodes an Alcohol-Forming Fatty Acyl-Coenzyme A Reductase Involved in Cuticular Wax production in Arabidopsis"(2006) Plant Physiol 142: 866-877.

Schirmer et al,: "Microbial biosynthesis of alkanes"; (2010) Science 329(5991):559-562.

Shrivastava et al.: "Identification and Functional Characterization of Gene Components of Type VI Secretion System in Bacterial Genomes"; PLoS ONE, Aug. 2008, 3:8, 1-11, table 6 pgs.

Steen et al.: "Microbial production of fatty-acid-derived fuels and chemicals from plant biomass"; (2010) Nature 463: 559-563.

Tan et al.: "Photosynthesis driven conversion of carbon dioxide to fatty alcohols and hydrocarbons in cyanobacteria"; (2011) Metabolic Engineering, 2011. 13(2): p. 169-176.

Teerawanichpan et al.: "Fatty acyl-CoA reductase and wax synthase from Euglena gracilis in the biosynthesis of medium-chain wax esters"; (2010) Lipids 42: 263-273.

Teerawanichpan et al.: "A fatty acyl-CoA reductase highly expressed in the head of honey bee (Apis mellifera) involves biosynthesis of a wide range of aliphatic fatty alcohols"; (2010) Insect Biochem Mol. Biol. 40: 641-649.

Van Dyk et al.: "Characterization of the Escherichia coli AaeAB Efflux Pump: a Metabolic Relief Valve?"; Biochem J. 366: 63-71 (2002).

Vioque et al.: "Resolution and Purification of an Aldehyde-Generating and an Alcohol-Generating Fatty Acyl-CoA Reductase from Pea Leaves (Pisum sativum L.)"; (1997) Arch. Biochem. Biophys. 340: 64-72.

Voelker et al.: "Alteration of the specificity and regulation of fatty acid syntesis of Eschericia coil by expressionof a plant medium-chain acyl-acylcarrier protein thioesterase"; (1994) J. Bacteriol. 176: 7320-7327.

Wang et al.: "Solubilization and purification of aldehyde-generating fatty acyl-CoA reductase from green alga Botryococcus braunii"; FEBS Letters 370 (1995) 15-18.

Whalen et al.: "Purification, Characterization, and Potential Bacterial Wax Production Role of an NADPH-Dependent Fatty Aldehyde Reductase from Marinobacter aquaeolei VT8"; Appl Environ Microbiol, 75: 2758-2764 (2009).

* cited by examiner

MAIQQVHHADTSSSKVLGQLRGKRVLITGTTGFLGKVVLERLIRAVPDIGAIYLL
IRGNKRHPDARSRFLEEIATSSVFDRLREADSEGFDAFLEERIHCVTGEVTEAGF
GIGQEDYRKLATELDAVINSAASVNFREELDKALAINTLCLRNIAGMVDLNPKLA
VLQVSTCYVNGMNSGQVTESVIKPAGEAVPRSPDGFYEIEELVRLLQDKIEDVQA
RYSGKVLERKLVDLGIREANRYGWSDTYTFTKWLGEQLLMKALNGRTLTILRPSI
IESALEEPAPGWIEGVKVADAIILAYAREKVTLFPGKRSGIIDVIPVDLVANSII
LSLAEALGEPGRRRIYQCCSGGGNPISLGEFIDHLMAESKANYAAYDHLFYRQPS
KPFLAVNRALFDLVISGVRLPLSLTDRVLKLLGNSRDLKMLRNLDTTQSLATIFG
FYTAPDYIFRNDELMALANRMGEVDKGLFPVDARLIDWELYLRKIHLAGLNRYAL
KERKVYSLKTARQRKKAA    (SEQ ID NO: 2)

Figure 1

MKQSLTLTAFANKNVLITGTTGFVGKVVLEKLLRSVPTIGKIYLLIRGNSKNPTA
RKRFQNEIATSSIFDTLKASQGSRFEELCETRIHCVTGEVTEPLFGLSEKDFTDL
AADIDVIINSAASVNFREALDQALTINTLCLKNIIELSRRAADCPVVQVSTCYVN
GFNQGVMEEEIVSPAGERIERSERGYYEVEPLIARLLQDVEQVSAAAADDHSREK
DLIDLGIKEANKYGWNDTYTFTKWMGEQLLMKELYGKTLTILRPSIVESTLLGPA
PGWIEGVKVADAIILAYAREKVSLFPGKKNAVIDIIPADLVANSIILSATEALLD
SGAHRIYQCCSSEVNPIRIREVIGHVQQEAEHNYQTHDKLFYRKPKKPFVMIPGA
VFHALMAISFHMLKWSSRLQSLFGRKASGRKLSNMETTMKLSKVFSFYTSPSYTF
SNRRLQELSTRLGEYDQSEFPVNAGMYDWAHYLREVHVAGLNKYALRPKVVKMNP
PAAKPRSRAA        (SEQ ID NO: 4)

Figure 2

MATQQQQNGASASGVLEQLRGKHVLITGTTGFLGKVVLEKLIRTVPDIGGIHLLI
RGNKRHPAARERFLNEIASSSVFERLRHDDNEAFETFLEERVHCITGEVTESRFG
LTPERFRALAGQVDAFINSAASVNFREELDKALKINTLCLENVAALAELNSAMAV
IQVSTCYVNGKNSGQITESVIKPAGESIPRSTDGYYEIEELVHLLQDKISDVKAR
YSGKVLEKKLVDLGIREANNYGWSDTYTFTKWLGEQLLMKALSGRSLTIVRPSII
ESALEEPSPGWIEGVKVADAIILAYAREKVSLFPGKRSGIIDVIPVDLVANSIIL
SLAEALSGSGQRRIYQCCSGGSNPISLGKFIDYLMAEAKTNYAAYDQLFYRRPTK
PFVAVNRKLFDVVVGGMRVPLSIAGKAMRLAGQNRELKVLKNLDTTRSLATIFGF
YTAPDYIFRNDSLMALASRMGELDRVLFPVDARQIDWQLYLCKIHLGGLNRYALK
ERKLYSLRAADTRKKAA    (SEQ ID NO: 6)

Figure 3

MATQQLNPDASSKVLERLRGKHVLITGTTGFLGKVVLEKLIRAVPDIGGIHLLIR
GNKRHPDARDRFFEEIATSSVFDRLRQDDNEAFETFIEDRVHCVTGEVTEPLFGL
SADRFRKLAGGIDVVVNSAASVNFREELDKALAINTRCLDNVAELARQNKSLAVL
QVSTCYVNGMNSGQITETVIKPAGEAIPRSTEGYYEIEELVRLLEDKIADVRSRY
SGKALEKKLVDLGIREANHYGWSDTYTFTKWLGEQLLLKALSGRALTIVRPSIIE
SALEEPAPGWIEGVKVADAIILAYAREKVTLFPGKRAGVIDVIPVDLVANAIILA
AAEAVADSPRHRIYQCCSGSSNPVSLGQFIDHLMAESKANFAEYDQLFYRQPTKP
FIAVNRRLFDAVVGGVRIPLSITGKVLRMLGQNRELKVLRNLDTTRSLATIFGFY
TAPDYIFRNDDLLALASRMGELDKVLFPVDARQIDWSVYLRKIHLAGLNRYALKE
RKVYSLRSAKARKKAA    (SEQ ID NO: 8)

Figure 4

MSQYSAFSVSQSLKGKHIFLTGVTGFLGKAILEKLLYSVPQLAQIHILVRGGKVS
AKKRFQHDILGSSIFERLKEQHGEHFEEWVQSKINLVEGELTQPMFDLPSAEFAG
LANQLDLIINSAASVNFRENLEKALNINTLCLNNIIALAQYNVAAQTPVMQISTC
YVNGFNKGQINEEVVGPASGLIPQLSQDCYDIDSVFKRVHSQIEQVKKRKTDIEQ
QEQALIKLGIKTSQHFGWNDTYTFTKWLGEQLLIQKLGKQSLTILRPSIIESAVR
EPAPGWVEGVKVADALIYAYAKGRVSIFPGRDEGILDVIPVDLVANAAALSAAQL
MESNQQTGYRIYQCCSGSRNPIKLKEFIRHIQNVAQARYQEWPKLFADKPQEAFK
TVSPKRFKLYMSGFTAITWAKTIIGRVFGSNAASQHMLKAKTTASLANIFGFYTA
PNYRFSSQKLEQLVKQFDTTEQRLYDIRADHFDWKYYLQEVHMDGLHKYALADRQ
ELKPKHVKKRKRETIRQAA    (SEQ ID NO: 10)

[Bar chart showing total fatty alcohol (ug/mL) on y-axis (0 to 7). Two conditions on x-axis: "Dodecane Type VI secretion and HcFAR reductase 25 uM nickel" shows approximately 4 ug/mL with error bar; "Dodecane Type VI secretion and HcFAR 0uM Ni" shows 0.]

PRODUCTION AND SECRETION OF FATTY ACIDS AND FATTY ACID DERIVATIVES

This application claims benefit of priority under 35 U.S.C. §119(e) to U.S. Provisional application 61/539,640 filed Sep. 27, 2011 entitled "Fatty Alcohol-Forming Acyl-ACP Reductases", which is incorporated by reference in its entirety.

REFERENCE TO A SEQUENCE LISTING

This application contains references to amino acid sequences and/or nucleic acid sequences which have been submitted concurrently herewith as the sequence listing text file "SGI1670-1_ST25.txt", file size 129 KiloBytes (KB), created on Sep. 27, 2012. The aforementioned sequence listing is hereby incorporated by reference in its entirety pursuant to 37 C.F.R. §1.52(e)(5).

TECHNICAL FIELD

The present application relates to genetic engineering of microorganisms for the production of compounds that may be used for various products, including biofuels.

BACKGROUND

The ever-increasing global demand for energy has led to depletion of fossil fuels, which are buried combustible geologic deposits of organic materials that have been converted to crude oil, coal, natural gas, or heavy oils. Because fossil fuels are formed by exposure to heat and pressure in the earth's crust over hundreds of millions of years, they are a finite, non-renewable resource. Accordingly, there is a need for non-fossil fuel energy sources.

Hydrocarbons from biological sources represent a clean, sustainable alternative energy source. Further, many industries, including plastics and chemical manufacturers, rely heavily on the availability of hydrocarbons for manufacturing processes. Currently, energy-rich lipids and fatty acids ("nature's petroleum") are isolated from plant and animal oils to produce diverse products such as fuels and oleochemicals. Recent efforts have focused on the microbial production of fatty acids and fatty acid derivatives by cost-effective bioprocesses. Methods of producing fatty acids and/or fatty acid derivatives in microbial hosts are described in, e.g., PCT Publication Nos. WO 2007/136762, WO 2008/119082, WO 2009/009391, WO 2009/076559, WO 2009/111513, WO 2010/006312, WO 2010/044960, WO 2010/118410, WO 2010/126891, WO 2011/008535, and WO 2011/019858, and in Schirmer et al., *Science* 329(5991):559-562 (2010).

Long chain fatty alcohols possess high energy density relative to shorter-chain biofuel products such as ethanol, and can be produced in cultured cells via a series of enzymatic processes. Fatty alcohols can also be enzymatically or catalytically converted to hydrocarbons such as alkenes. Fatty alcohols and their derivatives have numerous commercial applications, including use as surfactants, lubricants, plasticizers, solvents, emulsifiers, emollients, thickeners, flavors, fragrances and fuels.

Enzymes that convert fatty acyl-CoA to fatty alcohols or fatty aldehydes are commonly known as fatty acyl-CoA reductases ("FARs"). FARs have been identified in, e.g., *Euglena* (see, e.g., Teerawanichpan et al., *Lipids* 45:263-273 (2010)), *Arabidopsis* (see, e.g., Rowland et al., *Plant Physiol.* 142:866-877 (2006), Doan et al., *J. Plant Physiol.* 166:787-796 (2009) and Domergue et al., *Plant Physiol.* 153:1539-1554 (2010)), *Artemisia* (see, e.g., Maes et al., *New Phytol.* 189:176-189 (2011)), jojoba (see, e.g., Metz et al., *Plant Physiol.* 122:635-644 (2000)), moth (see, e.g., Lienard et al., *Proc. Natl. Acad. Sci.* 107:10955-10960 (2010)), bee (see, e.g., Teerawanichpan et al., *Insect Biochemistry and Molecular Biology* 40:641-649 (2010)) and in mammals (see, e.g., Honsho et al., *J. Biol. Chem.* 285:8537-8542 (2010)). Alcohol-forming acyl-CoA reductases are thought to generate fatty alcohols directly from acyl-CoA. Enzyme-based conversion of acyl-CoA to fatty alcohol can also occur in a two-enzyme, two-step reaction; in the first step, acyl-CoA is reduced to fatty aldehyde by an aldehyde-forming acyl-CoA reductase, and in the second step, the fatty aldehyde is reduced to a fatty alcohol by a fatty aldehyde reductase.

Typically, to produce fatty alcohols in a microorganism, it is necessary to introduce various enzymes in addition to at least one FAR. For example, in a host that does not endogenously produce acyl-CoA, such as a cyanobacterial host, it may be necessary to introduce, e.g., a fatty acid thioesterase to convert acyl-acyl carrier protein (acyl-ACP) to free fatty acids and acyl-CoA synthetase to convert free fatty acids to acyl-CoA, in addition to an acyl-CoA reductase to reduce acyl-CoA to fatty alcohols. Even in host organisms that naturally produce acyl-CoA, it can be advantageous to introduce a gene encoding an acyl-CoA synthetase (and, in many cases, an acyl-ACP thioesterase or an acyl-CoA thioesterase to provide the fatty acid substrate for the acyl-CoA synthetase) such that acyl-CoA is produced in higher amounts than occur in the absence of acyl-CoA synthetase overexpression. Other enzymes that can be engineered into a host strain to provide substrates for alcohol-forming FARs include aldehyde-forming acyl reductases such as aldehyde-forming acyl-CoA reductases (e.g., Reiser amd Somerville (1997) *J. Bacteriol.* 179: 2969-2975; Wang and Kolattukudy (1995) *FEBS Lett.* 370: 15-18; Vioque and Kolattukudy (1997) *Arch. Biochem. Biophys.* 340: 64-72) or aldehyde-forming acyl-ACP reductases (e.g., WO 2011/006137). Introducing several heterologous pathway components, however, may lead to difficulties in appropriately balancing enzyme expression and activity to produce the desired end product in sufficiently high yields for large scale production. Moreover, the buildup of intermediates such as free fatty acids can be toxic to the host cell, further reducing yield.

Secretion of a free fatty acid or a fatty acid derivative such as a fatty alcohol can also improve the efficiency of a production system. The multidrug resistance (MDR) transporters of prokaryotes can export a wide variety of substrates using energy supplied by either hydrolysis of ATP or a proton or sodium-motive force. The ATP-binding cassette (ABC) "primary transporters" or efflux pumps use ATP hydrolysis to drive substrate export, whereas the "secondary transporters" use proton motive force or proton motive force to drive substrate export. Included in the family of secondary transporters or efflux pumps are the Major Facilitator Superfamily (MFS), the Small Multidrug Resistance (SMR) family, the Resistance-cell Division (RND) family, the Multi Antimicrobial Extrusion (MATE) family, and the Putative E Transporter (PET) family (Mazurkiewicz et al. (2005) *Cur Issues Mol Biol* 7: 7-22; Haley and Saier (2000) *J. Mol. Microbiol. Biotechnol.* 2: 195-198). Prokaryotes also have protein secretion systems, currently classified as Secretion Systems I to VI, that transport effector proteins out of the bacterial cell (Shrivastava and Mande (2009) *PLoS ONE* 3: e2955).

SUMMARY OF THE INVENTION

The present invention provides acyl-CoA-independent methods for producing fatty alcohols. The invention is based in part on the inventors' discovery that expression of certain fatty acyl reductases in a heterologous acyl-CoA-free host results in the production of fatty alcohol.

In methods of the invention, fatty alcohols are produced by introducing into host cells a gene encoding an alcohol-forming reductase that is capable of using a non-acyl-CoA substrate. The acyl-CoA-independent pathway can bypass the generation of acyl-CoA pathway intermediates such as, for example, free fatty acids, which can be toxic to the host cell. Further, because the acyl-CoA-independent pathway does not require the ATP-dependent step of forming a fatty acyl-CoA substrate from free fatty acid, this pathway may be more energy-efficient than traditional acyl-CoA-dependent pathways.

In certain embodiments the fatty alcohols are produced by a recombinant microorganism that includes a non-native gene that encodes an alcohol-forming reductase that uses acyl-ACP as a substrate (an "alcohol-forming acyl-ACP reductase"), in which the recombinant microorganism does not express any of: an exogenous acyl-ACP thioesterase, an exogenous acyl-CoA thioesterase, or an exogenous acyl-CoA synthetase. The methods include culturing the recombinant microorganism in a suitable culture medium, and allowing expression of the alcohol-forming acyl-ACP reductase gene. Additionally, expression of the alcohol-forming acyl-ACP reductase gene can result in the production of at least 0.5 milligrams (mg) fatty alcohols per liter (L) of culture in a seven day culture period. In some embodiments, the recombinant microorganism can be a microorganism that does not produce acyl-CoA. Additionally or alternatively, the recombinant microorganism does not include an endogenous gene encoding an acyl-CoA synthetase. Alternatively, the recombinant microorganism can include an endogenous gene encoding an acyl-CoA synthetase, in which expression of the endogenous gene is attenuated, for example by insertional inactivation or gene replacement.

Because alcohol-forming acyl-ACP reductases are capable of directly converting acyl-ACP to fatty alcohols and do not require an acyl-CoA substrate, by using alcohol-forming acyl-ACP reductases for microbial production of fatty alcohols, the difficulties of introducing and balancing several enzyme expression levels and/or activities may be avoided. Further advantages include the comparative ease of mutagenizing or modifying the expression level of a single gene, as compared to multiple genes, to achieve, e.g., higher production levels or different chain length specificity.

Accordingly, the invention provides acyl-CoA-independent methods for producing a fatty alcohol using a host microorganism transformed with a gene encoding an alcohol-forming acyl-ACP reductase, where the alcohol-forming acyl-ACP reductase can be a microbial alcohol-forming acyl-ACP reductase, e.g., a prokaryotic alcohol-forming acyl-ACP reductase, such as an alcohol-forming acyl-ACP reductase derived from a marine bacterium, such as, for example, the Maqu_2220 reductase (SEQ ID NO: 2) or the Hch_05075 reductase (SEQ ID NO: 4), or can be transformed with a gene encoding an alcohol-forming acyl-ACP reductase with at least 40%, 50%, 60%, 70%, 75%, 85%, 90%, 92%, 93%, 94%, 95%, 96%, 97%, 98%, or 99% amino acid sequence identity to Maqu_2220 or Hch_05075. For example, a host microorganism can include a non-native gene encoding an alcohol-forming acyl-ACP reductase having an amino acid sequence with at least 90% identity with SEQ ID NO: 2. Alternatively, the non-native gene may include an alcohol-forming acyl-ACP reductase having an amino acid sequence with at least 90% sequence identity with SEQ ID NO: 4.

In some embodiments, the invention provides acyl-CoA-independent methods for producing a fatty alcohol using a host microorganism expressing an alcohol-forming acyl-ACP reductase encoded by a non-native nucleic acid sequence with at least 30%, 40%, 50%, 60%, 70%, 75%, 85%, 90%, 92%, 93%, 94%, 95%, 96%, 97%, 98%, or 99% sequence identity to a nucleic acid sequence encoding Maqu_2220 (SEQ ID NO: 1) or a nucleic acid sequence encoding Hch_05075 (SEQ ID NO: 3). The non-native amino acid sequence may have at least 85% identity with SEQ ID NO: 1. Alternatively, the non-native amino acid sequence may have at least 85% sequence identity with SEQ ID NO: 3.

In some embodiments, the invention provides acyl-CoA-independent methods for producing a fatty alcohol, in which the methods include expressing in a host microorganism a gene encoding an alcohol-forming acyl-ACP reductase from *Marinobacter algicola* strain DG893 ("MDG893_11561"; SEQ ID NO: 6), *Marinobacter adhaerens* strain HP15 ("HP15_810"; SEQ ID NO: 8); or *Oceanobacter* sp. strain RED65 ("RED65_09894"; SEQ ID NO: 10), or to a gene encoding an alcohol-forming acyl-ACP reductase with at least 40%, 50%, 60%, 70%, 75%, 85%, 90%, 92%, 93%, 94%, 95%, 96%, 97%, 98%, or 99% amino acid sequence identity to any of these polypeptides. For example, the methods may include expressing in a host microorganism a gene encoding an acyl-ACP reductase having at least 90% amino acid sequence identity to SEQ ID NO: 6; or alternatively at least 90% amino acid sequence identity to SEQ ID NO: 8; or alternatively at least 90% amino acid sequence identity to SEQ ID NO: 10. In some embodiments, the invention provides acyl-CoA-independent methods for producing a fatty alcohol using an alcohol-forming acyl-ACP reductase encoded by a nucleic acid sequence with at least 30%, 40%, 50%, 60%, 70%, 75%, 85%, 90%, 92%, 93%, 94%, 95%, 96%, 97%, 98%, or 99% sequence identity to a nucleic acid sequence encoding MDG893_11561 (SEQ ID NO: 5), a nucleic acid sequence encoding HP15_810 (SEQ ID NO: 7), or a nucleic acid sequence encoding RED65_09894 (SEQ ID NO: 9). For example the nucleic acid sequence may have at least 85% identity to SEQ ID NO: 5. Alternatively, the nucleic acid sequence may have at least 85% identity to SEQ ID NO: 7 or the nucleic acid sequence may have at least 85% identity to SEQ ID NO: 9.

In some additional embodiments, the invention provides methods for producing a fatty alcohol in a photosynthetic microorganism. In some embodiments, the photosynthetic microorganism can be, e.g., a cyanobacterium or a eukaryotic microalga. Photosynthetic microorganisms are able to use inorganic carbon (e.g., carbon dioxide) as a carbon source, and may thus provide a more efficient and cost-effective method of fatty alcohol production than host cells that wholly depend on reduced carbon sources. In some embodiments, the photosynthetic microorganism may be transformed with a gene encoding an alcohol-forming reductase selected from, e.g., Maqu_2220 (SEQ ID NO: 2), Hch_05075 (SEQ ID NO: 4), MDG893_11561 (SEQ ID NO: 6), HP15_810 (SEQ ID NO: 8) or RED65_09894 (SEQ ID NO: 10), or an alcohol-forming acyl-ACP reductase having at least about 40%, 50%, 60%, 70%, 75%, 85%, 90%, 92%, 93%, 94%, 95%, 96%, 97%, 98%, or 99% sequence identity thereto. For example, the gene may encode an alcohol-forming acyl-ACP reductase having at least 90% sequence identity with SEQ ID NO: 2. Alternatively, the gene may encode an alcohol-forming aryl-ACP reductase having at least 90% sequence identity with SEQ ID NO: 4. The gene may encode an alcohol-forming acyl-ACP reductase having 90% sequence identity with SEQ ID NO: 6 or the gene may encode an alcohol-forming acyl-ACP reductase having at least 90% sequence identity with SEQ ID NO: 8. The gene may encode an alcohol-forming acyl-ACP reductase having 90% sequence identity with SEQ ID NO: 10. The gene encoding the alcohol-forming acyl-ACP reductase may in some embodiments be codon-optimized for expression in the photosynthetic host microorganism.

In some embodiments, the invention provides methods that include culturing a photosynthetic microorganism that includes a non-native nucleic acid sequence encoding an alcohol-forming acyl-ACP reductase and allowing expression of the nucleic acid sequence, such that the recombinant photosynthetic microorganism produces at least about 0.5 mg of fatty alcohols per liter of culture in a culture period of seven days, for example, at least about 1 mg/L, 2 mg/L, 5 mg/L or 10 mg/L of fatty alcohol/culture in a period of seven days, or an average of at least about 0.1 mg/L, 0.2 mg/L, 0.5 mg/L, 1 mg/L or 2 mg/L of fatty alcohol/culture for a culture period of from about one day to about thirty days, or between about 0.5 milligrams per liter and about 500 milligrams per liter, or between about 1 mg/L and about 250 mg/L, or between about 1 mg/L and about 100 mg/L, or between about 2 mg/L and about 200 mg/L, or between about 2 mg/L and about 25 mg/L, or between about 5 mg/L and about 100 mg/L, or between about 2 mg/L and about 50 mg/L, or between about 2 mg/L and about 25 mg/L, or between about 5 mg/L and about 25 mg/L, or between about 5 mg/L and about 50 mg/L, or between about 10 mg/L and about 50 mg/L, or between about 10 mg/L and about 100 mg/L of fatty alcohol/culture per day for a culture period of from about one day to about thirty days. Additionally, in certain embodiments, at least a portion of the fatty alcohol produced by the photosynthetic microorganism can be secreted. The ratio of the amount of the fatty alcohol produced to the amount of fatty alcohol secreted can be, for example, less than about 5:1, 4:1, 3:1, 2:1, 1.5:1, or can be about 1:1. The photosynthetic microorganism can be cultured phototrophically for alcohol production, in a culture medium that includes inorganic carbon, for example, $CO_2$ or a carbonate, as substantially the sole source of carbon, wherein the microorganism is exposed to light for at least a portion of the culture period.

In some embodiments, the recombinant photosynthetic microorganism used in the methods of the invention can be a photosynthetic microorganism that does not produce acyl-CoA. For example, in any of the embodiments provided herein, the recombinant photosynthetic microorganism may be a microorganism that does not produce an acyl-CoA synthetase. In some embodiments, the recombinant photosynthetic microorganism can be a photosynthetic microorganism that does not endogenously produce acyl-CoA, for example, a photosynthetic microorganism that does not include an endogenous gene encoding an acyl-CoA synthetase. Alternatively, endogenous expression of enzymes directly involved in the synthesis of acyl-CoA can be attenuated or eliminated in the photosynthetic microorganism, for example, by genetic engineering. This attenuation or elimination may be accomplished by using, for example, antisense, RNAi, or ribozymes constructs, or gene disruption by homologous recombination. In certain embodiments, the photosynthetic microorganism does not include an introduced gene encoding an acyl-CoA synthetase.

Additionally, in various embodiments, the photosynthetic microorganism can be a microorganism that does not include an exogenous gene encoding an acyl-ACP thioesterase and/or can be a microorganism that does not include an exogenous gene encoding an acyl-CoA thioesterase. Alternatively or in addition, the photosynthetic microorganism can be a microorganism that does not include an endogenous gene encoding an acyl-ACP thioesterase and/or does not include an endogenous gene encoding an acyl-CoA thioesterase; and/or the photosynthetic microorganism can be engineered for reduced expression of an endogenous gene encoding an acyl-ACP thioesterase and/or an endogenous gene encoding an acyl-CoA thioesterase. In an exemplary embodiment, the photosynthetic microorganism that includes a non-native gene encoding an alcohol-forming acyl-ACP reductase does not include an endogenous or exogenous gene encoding any of an acyl-ACP thioesterase, an acyl-CoA thioesterase, and an acyl-CoA synthetase.

In certain embodiments, the methods of the invention can be advantageously carried out in cyanobacterial host cells. Cyanobacteria synthesize acyl-ACP, but do not naturally make acyl-CoA or fatty alcohols. Further, genes encoding acyl-CoA synthetases, acyl-ACP thioesterases or acyl-CoA thioesterases are not found in cyanobacterial genomes. By the methods of the present invention, cyanobacterial host cells can be engineered to produce fatty alcohols by introducing an alcohol-forming acyl-ACP reductase gene (for example, a gene encoding Maqu_2220 (e.g., SEQ ID NO: 2), Hch_05075 (e.g., SEQ ID NO: 4), MDG893_11561 (e.g., SEQ ID NO: 6), HP15_810 (e.g., SEQ ID NO: 8) or RED65_09894 (e.g., SEQ ID NO: 10), or a gene encoding an alcohol-forming acyl-ACP reductase having at least 40%, 50%, 60%, 70%, 75%, 85%, 90%, 92%, 93%, 94%, 95%, 96%, 97%, 98%, or 99% sequence identity to SEQ ID NO: 2, 4, 6, 8, or 10. Further, because cyanobacteria are photosynthetic microorganisms that can utilize inorganic (non-reduced) carbon sources, such as $CO_2$, compared to, e.g., heterotrophic cells that depend on reduced (organic) carbon sources, cyanobacteria transformed with an alcohol-forming acyl-ACP reductase gene may provide a more streamlined and energy-efficient biological system for fatty alcohol production.

In some embodiments, in addition to expressing a non-native nucleic acid sequence encoding an alcohol-forming acyl-ACP reductase, a recombinant microorganism used in the methods of the invention can optionally express an exogenous and/or endogenous fatty aldehyde-forming reductase, e.g., a carboxylic acid reductase or an aldehyde-forming acyl-ACP reductase. Optionally, a recombinant microorganism as provided herein can express an exogenous cyanobacterial aldehyde-forming acyl-ACP reductase; additionally or alternatively, the recombinant microorganism can include an endogenous gene encoding an aldehyde-forming acyl-ACP reductase, i.e., a gene derived from the host microorganism; for example, the recombinant microorganism can overexpress an endogenous gene encoding an aldehyde-forming acyl-ACP reductase. In particular embodiments, the host microorganism used in the methods of the invention may not express a gene encoding na exogenous aldehyde-forming acyl-ACP reductase.

In some embodiments, a host microorganism as disclosed herein that expresses an alcohol-forming acyl-ACP reductase can also be engineered to overexpress one or more additional enzymes in the acyl-ACP-dependent fatty alcohol biosynthesis pathway, such as, for example, a beta-ketoacyl synthetase, an acetyl-CoA carboxylase, a malonyl-CoA:ACP transacylase, an acyl-ACP synthetase, or acyl carrier protein. One or more genes encoding the additional enzyme(s) may be introduced into the host microorganism, or one or more genes endogenous to the host microorganism can be engineered for overexpression. For example, a host microorganism that expresses a non-native acyl-ACP reductase can further include an exogenous gene encoding an acetyl-CoA carboxylase, or can be engineered for up-regulation or overexpression of an endogenous gene encoding an acetyl-CoA carboxylase.

In another aspect, the invention provides an isolated nucleic acid molecule that encodes an alcohol-forming acyl-ACP reductase, wherein the isolated nucleic acid molecule comprises a nucleic acid sequence encoding a reductase having at least 40%, 50%, 60%, 70%, 75%, 85%, 90%, 92%, 93%, 94%, 95%, 96%, 97%, 98%, or 99% sequence identity to a nucleic acid sequence encoding SEQ ID NO: 2, SEQ ID NO: 4, SEQ ID NO: 6, SEQ ID NO: 8, or SEQ ID NO: 10, wherein the isolated nucleic acid molecule further comprises an additional nucleic acid sequence of at least 50 nucleotides from a photosynthetic microorganism. In some embodiments, the nucleic acid molecule can include a promoter operably linked to the sequence encoding the alcohol-forming acyl-ACP reductase. In certain embodiments, the promoter can be heterologous with respect to the alcohol-forming acyl-ACP reductase. Further, the invention provides vectors comprising at least one of the isolated nucleic acid molecules and recombinant host cells comprising at least one of the isolated nucleic acid molecules or vectors.

The invention also provides recombinant microorganisms that express a non-native gene encoding an alcohol-forming acyl-ACP reductase and produce at least one fatty alcohol. In some embodiments, the host microorganism can produce a greater amount of fatty alcohol, e.g., at least 50% more alcohol, than a microorganism cultured under identical conditions and identical in all respects except that it does not include a non-native gene encoding an alcohol-forming acyl-ACP reductase. The gene encoding the alcohol-forming acyl-ACP reductase can be integrated into the genome of the host microorganism, or can be maintained within the host on a vector (for example, a replicating vector such as an episome). The recombinant host microorganism that expresses a non-native gene encoding an alcohol-forming acyl-ACP reductase can be a recombinant microorganism that does not produce one or more of an acyl-ACP thioesterase, an acyl-CoA thioesterase, or an acyl-CoA synthetase. In some embodiments, the recombinant microorganism does not produce any of an acyl-CoA synthetase, an acyl-CoA thioesterase, and an acyl-ACP thioesterase. In some embodiments, the alcohol-producing host microorganism can be a microorganism that does not include one or more endogenous genes encoding one or more of an acyl-ACP thioesterase, an acyl-CoA thioesterase, or an acyl-CoA synthetase. For example, the host microorganism can lack endogenous genes for all of an acyl-ACP thioesterase, an acyl-CoA thioesterase, or an acyl-CoA synthetase. Alternatively, the host microorganism can be a microorganism in which expression of endogenous gene(s) encoding one or more of an acyl-ACP thioesterase, an acyl-CoA thioesterase, or an acyl-CoA synthetase is attenuated. For example, the host microorganism can have attenuated expression of an acyl-CoA synthetase.

The host microorganism in certain embodiments can optionally further include one or more exogenous nucleic acid sequences, or overexpress one or more endogenous genes, encoding: an aldehyde-forming reductase, a polypeptide for increasing acyl-ACP production, a polypeptide for increasing carbon fixation, or a transmembrane pump or transporter. For example, a host microorganism may express exogenous gene(s), or overexpress endogenous gene(s), encoding one or more of a beta-ketoacyl synthetase, an acetyl-CoA carboxylase, a malonyl-CoA:ACP transacylase, acyl carrier protein, an acyl-ACP synthetase, ribulose 1,5-bisphosphate carboxylase and a phycobiliprotein (e.g., phycocyanin). Additionally or alternatively, the host microorganism may have attenuated or eliminated expression of at least one of glycerol-3-phosphate dehydrogenase, acetaldehyde-CoA dehydrogenase, pyruvate dehydrogenase and acetate kinase.

In some embodiments, a recombinant microorganism of the invention can be a recombinant microorganism that produces at least about 1 mg/L, 2 mg/L, 5 mg/L or 10 mg/L of fatty alcohol/culture in a culture period of seven days, or an average of at least about 0.1 mg/L, 0.2 mg/L, 0.5 mg/L, 1 mg/L or 2 mg/L of fatty alcohol/culture per day, for a culture period of from about one day to about thirty days, or between about 0.5 milligrams per liter and about 500 milligrams per liter, or between about 1 mg/L and about 250 mg/L, or between about 1 mg/L and about 10 mg/L, or between about 2 mg/L and about 200 mg/L, or between about 2 mg/L and about 25 mg/L, or between about 5 mg/L and about 100 mg/L, or between about 2 mg/L and about 50 mg/L, or between about 2 mg/L and about 25 mg/L, or between about 5 mg/L and about 25 mg/L, or between about 5 mg/L and about 50 mg/L, or between about 10 mg/L and about 50 mg/L, or between about 10 mg/L and about 100 mg/L of fatty alcohol/culture per day for a culture period of from about one day to about thirty days. Additionally, at least a portion of the fatty alcohol produced by the photosynthetic microorganism can be secreted. The ratio of the amount of the fatty alcohol produced to the amount of fatty alcohol secreted can be, for example, less than about 5:1, 4:1, 3:1, 2:1, 1.5, or can be about 1:1.

In some embodiments, the recombinant microorganism can be a recombinant photosynthetic microorganism. For example, the recombinant microorganism can be a eukaryotic microalga, including but not limited to any of the species disclosed herein, such as, but not limited to an *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox* species.

Alternatively, the recombinant microorganisms can be a cyanobacterium, including, as a nonlimiting examples, a species of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanobacterium, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria,*

*Stigonema, Symploca, Synechococcus, Synechocystis, Thermosynechococcus, Tolypothrix, Trichodesmium, Tychonema* or *Xenococcus*. For example, the recombinant photosynthetic microorganism can be a *Synechococcus, Synechocystis*, or *Thermosynechococcus* species. Alternatively, the recombinant photosynthetic microorganism can be a *Cyanobium, Cyanothece*, or *Cyanobacterium* species, or further alternatively, the recombinant photosynthetic microorganism can be a *Gloeobacter, Lyngbya* or *Leptolyngba* species.

In certain embodiments, the photosynthetic microorganism does not include a gene encoding an acyl-CoA synthetase. In certain embodiments, the photosynthetic microorganism does not include an introduced gene encoding an acyl-CoA synthetase. Additionally or alternatively, the photosynthetic microorganism can lack an exogenous or endogenous gene encoding one or both of an acyl-ACP thioesterase or an acyl-CoA thioesterase. Alternatively, the photosynthetic microorganism can have attenuated expression of an endogenous gene encoding an acyl-ACP thioesterase and/or an acyl-CoA thioesterase.

A recombinant microorganism used in the methods of the invention can optionally express an exogenous and/or endogenous fatty aldehyde-forming reductase, e.g., a carboxylic acid reductase or an aldehyde-forming acyl-ACP reductase. For example, a recombinant microorganism as provided herein can express an exogenous cyanobacterial aldehyde-forming acyl-ACP reductase; additionally or alternatively, the recombinant microorganism can include a homologous gene encoding an aldehyde-forming acyl-ACP reductase, i.e., a gene derived from the host microorganism; for example, the recombinant microorganism can overexpress a homologous gene (e.g., an endogenous gene) encoding an aldehyde-forming acyl-ACP reductase.

The invention also provides systems for producing a fatty alcohol in an acyl-CoA-independent manner, e.g., culture systems that include a recombinant photosynthetic microorganism expressing an alcohol-forming acyl-ACP reductase. In some embodiments, the culture system includes a culturing vessel that contains the photosynthetic microorganism during the production period and permits exposure of the cultured microorganism to light. The culture vessel may further include media for photoautotrophic growth, e.g., media that does not include a substantial amount of a reduced carbon source. The invention further provides fatty alcohols produced using hosts and systems as provided herein.

Further provided are microorganisms engineered to produce free fatty acids or fatty acid derivatives, such as, but not limited to, fatty alcohols, that are also engineered to express one or more non-native genes encoding a component of a transmembrane transporter system, such as, for example, a component of a multidrug resistance transporter or a component of a bacterial protein secretion system. For example, a microorganism that includes at least one non-native gene that encodes a polypeptide that participates in the production of a free fatty acid or fatty acid derivative can further include at least one non-native gene that encodes a component of an ATP-Binding Cassette (ABC) transporter, or a component of a secondary transporter, such as, for example, a component of a Multi Antimicrobial Extrusion (MATE) transporter, a component of a Major Facilitator Superfamily (MFS) transporter, a component of a Small Multidrug Resistance (SMR) transporter, a component of a Putative Efflux Transporter (PET), or a component of a Resistance Nodulation-cell Division (RND) transporter. For example, a microorganism engineered to produce a free fatty acid or fatty acid derivative can further include a non-native gene encoding a polypeptide of an RND transporter, for example, a membrane fusion protein of an RND transporter, an inner membrane permease protein of an RND transporter, or an outer membrane protein component of an RND transporter. The non-native gene encoding a prokaryotic transporter protein can be an endogenous gene, for example, an endogenous gene operably linked to a heterologous promoter for regulated expression. Alternatively or in addition, the recombinant microorganism includes, in addition, to at least one non-native gene encoding an enzyme that participates in the production of a fatty acid or fatty acid derivative, a non-native gene encoding a component of a protein secretion system such as the Type VI Secretion System (T6SS). For example, the recombinant microorganism engineered for the production of a free fatty acid or fatty acid derivative can include a non-native gene encoding a VgrG protein or a functional fragment thereof.

A microorganism that expresses a non-native gene encoding a component of a prokaryotic secretion system can be a photosynthetic microorganism, and can be engineered to produce, for example, a free fatty acid, a fatty aldehyde, a fatty alcohol, a fatty acid ester, a wax ester, an alkane, or an alkene. In some examples the engineered microorganism that includes a non-native gene encoding a component of a prokaryotic secretion system or a transmembrane transporter can be engineered to produce a free fatty acid and can include a non-native gene encoding a thioesterase, such as an acyl-ACP thioesterase, an acyl-CoA thioesterase, or a hydroxybenzoyl thioesterase, where the microorganism produces and secretes at least one free fatty acid.

In related aspects, provided herein are methods for producing a free fatty acid or a fatty acid derivative, in which the method includes culturing a recombinant photosynthetic microorganism engineered for secretion of a free fatty acid or fatty acid product in a suitable culture medium, in which the recombinant photosynthetic microorganism comprises at least one non-native nucleic acid sequence that encodes a polypeptide that participates in the production of a free fatty acid or a fatty acid derivative and at least one non-native nucleic acid sequence that encodes a component of a prokaryotic multidrug resistance transporter; and allowing expression of the non-native nucleic acid sequences, wherein the expression results in the production and secretion of the free fatty acid or fatty acid derivative. In some examples, the recombinant photosynthetic microorganism produces a greater amount of the free fatty acid or fatty acid derivative than is produced by a control photosynthetic microorganism substantially identical in all respects to the recombinant photosynthetic microorganism engineered for secretion of a free fatty acid or fatty acid product, except that the control microorganism does not include a non-native gene encoding a component of a prokaryotic multidrug resistance transporter. Additionally or alternatively, the recombinant photosynthetic microorganism can secrete a greater amount of the free fatty acid or fatty acid derivative than is secreted by a control photosynthetic microorganism substantially identical in all respects to the recombinant photosynthetic microorganism engineered for secretion of a free fatty acid or fatty acid product, except that the control microorganism does not include a non-native gene encoding a component of a prokaryotic multidrug resistance transporter. In some examples, the prokaryotic multidrug resistance transporter is not an ABC transporter. In come examples, the recombinant photosynthetic microorganism includes a non-native gene encoding a component of a secondary multidrug resistance transporter. In some examples, the recombinant photosynthetic microorganism includes a non-native gene encoding a component of an RND transporter of an SMR transporter, for example, a component of a Mex efflux pump, an Acr efflux pump, an emr efflux pump, or a far efflux pump. In various examples, the recombinant photosynthetic microorganism can include one or more non-native genes encoding a membrane fusion protein of a secondary multidrug resistance transporter, an inner membrane permease protein of a secondary multidrug resistance transporter, or an outer membrane protein component of a secondary multidrug resistance transporter, where a secondary multidrug resistance transporter can be, e.g., an MFS, SMR, RND, MATE, or PET efflux pump.

In a further aspect, methods are provided for producing a free fatty acid or a fatty acid derivative, in which the method includes culturing a recombinant microorganism engineered for secretion of a free fatty acid or fatty acid product in a suitable culture medium, in which the recombinant microorganism comprises at least one non-native nucleic acid sequence that encodes a polypeptide that participates in the production of a free fatty acid or a fatty acid derivative and at least one non-native nucleic acid sequence that encodes a component of a prokaryotic protein secretion system; and allowing expression of the non-native nucleic acid sequences, wherein the expression results in the production and secretion of the free fatty acid or fatty acid derivative. In some examples, the recombinant microorganism produces a greater amount of the free fatty acid or fatty acid derivative than is produced by a control microorganism substantially identical in all respects to the recombinant microorganism engineered for secretion of a free fatty acid or fatty acid product, except that the control microorganism does not include a non-native gene encoding a component of a prokaryotic protein secretion system. Additionally or alternatively, the recombinant microorganism can secrete a greater amount of the free fatty acid or fatty acid derivative than is secreted by a control microorganism substantially identical in all respects to the recombinant microorganism engineered for secretion of a free fatty acid or fatty acid product, except that the control microorganism does not include a non-native gene encoding a component of a prokaryotic protein secretion system. In some examples, the prokaryotic protein secretion system is a Type VI Secretion System (T6SS). In come examples, the recombinant microorganism includes a non-native gene encoding a VgrG protein or an ortholog thereof, or an active fragment thereof. The microorganism engineered to express a component of a prokaryotic protein secretion system may be prokaryotic or eukaryotic and may be, for example, a species of archebacteria, eubacteria, heterokont, or fungus.

A recombinant photosynthetic microorganism may be cultured photoautotrophically or mixotrophically, where the recombinant photosynthetic microorganism is exposed to light for at least a portion of the culture period. In some embodiments, the recombinant microorganism is cultured phototrophically. In particular embodiments, the culture medium includes inorganic carbon as substantially the sole carbon source. For example, an inorganic carbon source such as $CO_2$, carbonic acid, or a carbonate compound can be substantially the sole source of carbon in the culture, providing the carbon for incorporation into biomolecules, including fatty alcohols.

BRIEF DESCRIPTION OF THE DRAWINGS

FIG. 1 shows the amino acid sequence of *Marinobacter aquaoelei* strain VT8 Maqu_2220 acyl-ACP reductase ("Maqu_2220"; SEQ ID NO: 2).

FIG. 2 shows the amino acid sequence of *Hahella chejuensis* strain KCTC 2396 alcohol-forming acyl-ACP reductase ("Hch_05075"; SEQ ID NO: 4).

FIG. 3 shows the amino acid sequence of a *Marinobacter algicola* strain DG893 alcohol-forming acyl-ACP reductase ("MDG893_11561"; SEQ ID NO: 6).

FIG. 4 shows the amino acid sequence of a *Marinobacter adhaerens* strain HP15 alcohol-forming acyl-ACP reductase ("HP15_810"; SEQ ID NO: 8).

FIG. 5 shows the amino acid sequence of an *Oceanobacter* sp. strain RED65 alcohol-forming acyl-ACP reductase ("RED65_09894"; SEQ ID NO: 10).

FIG. 21 is a graph showing the amount of fatty alchols in the dodecane layer of *Synechocystis* cultures expressing of the PfVgrG gene in addition to a Hch_05075 alcohol-forming acyl-ACP reductase gene in *Synechocystis* (left bar) as compared with a control *Synechocystis* strain that included the Hch_05075 alcohol-forming acyl-ACP reductase gene but did not include the PfVgrG gene (right bar).

DETAILED DESCRIPTION OF THE INVENTION

Figure 6:
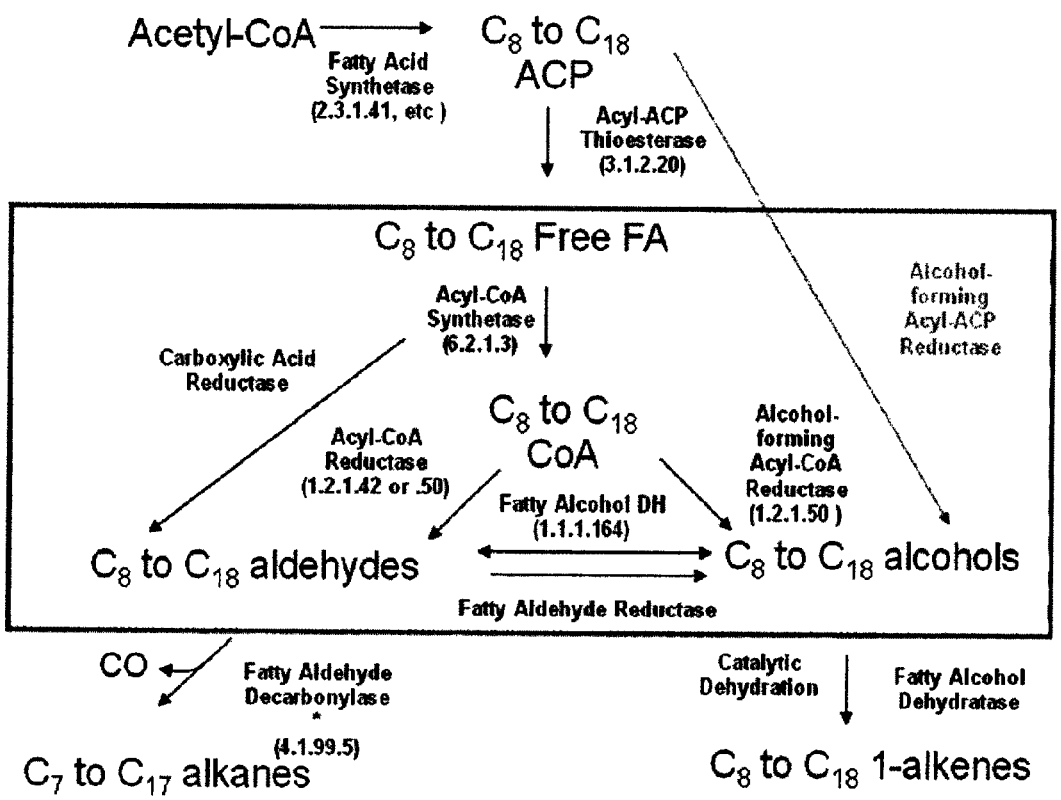
FIG. 6 is a schematic representation of fatty acid derivative metabolic pathways.

The invention provides acyl-CoA-independent methods of producing a fatty alcohol in recombinant host cells, as well as isolated nucleotide molecules, vectors, and recombinant host cells and systems for producing a fatty alcohol via an acyl-CoA-independent pathway.

The person skilled in the art will appreciate that the disclosure of this application includes the disclosure of embodiments comprising combinations of two or more features described for convenience by reference to specific embodiments. Headings within the application are solely for the convenience of the reader, and do not limit in any way the scope of the invention or its embodiments.

All publications and patent applications cited in this specification are incorporated herein by reference as if each individual publication or patent application were specifically and individually indicated to be incorporated by reference.

DEFINITIONS

Unless defined otherwise, all technical and scientific terms used herein have the same meaning as commonly understood by one of ordinary skill in the art to which this invention is related.

Throughout this specification and embodiments, the word "comprise," or variations such as "comprises" or "comprising," will be understood to imply the inclusion of a stated entity, item, or group of items but not the exclusion of any other entity, item, or group of items.

Singular articles "a," "an" and "the" include plural references unless the context clearly dictates otherwise. A reference to a cell, for example, includes a plurality of cells.

The term "alcohol-forming acyl-ACP reductase" refers to a protein that is able to convert acyl-ACP to a fatty alcohol. An "alcohol-forming acyl-CoA reductase" is a protein that is able to convert acyl-CoA to fatty alcohol. "Alcohol-forming fatty acyl reductase" refers to enzymes that can convert either acyl-ACP or acy-CoA to fatty alcohols, and includes "promiscuous alcohol-forming fatty acyl reductases" that are able to use both acyl-ACP and acyl-CoA as substrates for the production of fatty alcohols.

A "fatty alcohol" is a primary alcohol having the formula ROH, in which R is an aliphatic group, preferably an alkyl group. R can comprise between about 6 and about 24 carbon atoms. The aliphatic chain can be saturated, monounsaturated, or polyunsaturated. "One or more fatty alcohols" refers to one or more fatty alcohols of different chain length and/or saturation pattern, for example, a C16:1 fatty alcohol, a C18:2 fatty alcohol, and a C14 fatty alcohol are particular fatty alcohols.

The term "aldehyde-forming acyl reductase" or "aldehyde-forming reductase" refers to an enzyme that produces a fatty aldehyde from an acyl substrate, such as a carboxylic acid (e.g., a free fatty acid), an acyl-ACP, or an acyl-CoA. An "aldehyde-forming acyl-ACP reductase" refers to a protein that converts acyl-ACP to a fatty aldehyde.

A "fatty alcohol" is a primary alcohol having the formula ROH, in which R is an aliphatic group, preferably an alkyl group. R can comprise between about 6 and about 22 carbon atoms. The aliphatic chain can be saturated, monounsaturated, or polyunsaturated. "One or more fatty alcohols" refers to one or more fatty alcohols of different chain length and/or saturation pattern, for example, a C16:1 fatty alcohol, a C18:2 fatty alcohol, and a C14 fatty alcohol are different fatty alcohols.

A "wax ester" is an ester of a fatty acid and a long chain aliphatic alcohol. Wax esters have an A chain, derived from a fatty alcohol, of at least 8 carbons and a B chain, derived from an acyl-thioester, of at least 8 carbons.

The terms "peptide," "polypeptide" and "protein" are used interchangeably herein, although "peptide," in some instances, may be used to refer to a polypeptide having no more than about 100 amino acids, or no more than about 60 amino acids.

The term "functional fragment" refers to a polypeptide that has an amino-terminal and/or carboxy-terminal deletion, where the remaining amino acid sequence has at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% sequence identity to the corresponding positions in the reference sequence, and retains about 75%, 80%, 85%, 90%, 91%, 92%, 93%, 94%, 95%, 96%, 97%, 98%, 99% or 100% of the activity of the full-length polypeptide. Functional fragments may comprise, e.g., 90% or less, 80% or less, 70% or less, 60% or less, 50% or less, 40% or less, 30% or less, or 20% or less of the full-length polypeptide, and can include, for example, up to about 50%, 55%, 60%, 65%, 70%, 75%, 80%, 85%, 90%, 95%, 96%, 97%, 98%, or 99% of the full-length polypeptide. For example, a functional fragment in some examples has at least 85% identity to a corresponding amino acid sequence of a reference polypeptide, and retains at least 80% of the activity of the reference polypeptide. In some examples, a functional fragment in some examples has at least 90% identity to a corresponding amino acid sequence of a reference polypeptide, and retains at least 90% of the activity of the reference polypeptide.

This application discloses and refers to genes and proteins by identifiers used in long-established and extensively referenced databases maintained by the National Center for Biotechnology Information (NCBI). Accession numbers are unique identifiers for a sequence record publicly available at the National Center for Biotechnology Information website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

Percent identity or homology with respect to amino acid or nucleotide sequences is defined herein as the percentage of amino acid or nucleotide residues in the candidate sequence that are identical with the known polypeptides, after aligning the sequences for maximum percent identity and introducing gaps, if necessary, to achieve the maximum percent homology. Homology or identity at the nucleotide or amino acid sequence level may be determined using methods known in the art, including but not limited to BLAST (Basic Local Alignment Search Tool) analysis using the algorithms employed by the programs blastp, blastn, blastx, tblastn and tblastx (Altschul (1997), Nucleic Acids Res. 25, 3389-3402, and Karlin (1990), Proc. Natl. Acad. Sci. USA 87, 2264-2268), which are tailored for sequence similarity searching.

"Pfam" is a large collection of protein domains and protein families maintained by the Pfam Consortium and is available at several sponsored world wide web sites, including: pfam.sanger.ac.uk/ (Welcome Trust, Sanger Institute); pfam.sbc.su.se/ (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr/. The latest release of Pfam is Pfam 25.0 (March 2011, 12,273 families) based on the UniProt protein database release 2020_05. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment. (Unless otherwise specified, matches of a queried protein to a Pfam are Pfam-A matches.) All identified sequences belonging to the family are then used to automatically generate a full alignment for the familiy (Sonnhammer et al. (1998) Nucleic Acids Research 26: 320-322; Bateman et al. (2000) Nucleic Acids Research 26: 263-266; Bateman et al. (2004) Nucleic Acids Research 32, Database Issue: D138-D141; Finn et al. (2006) Nucleic Acids Research Database Issue 34: D247-251; Finn et al. (2010) Nucleic Acids Research Database Issue 38: D211-222). By accessing the pfam database (for example, using any of the above-reference websites), protein sequences can be queried against the HMMs using HMMER homology search software (e.g., HMMER3, hmmer.janelia.org/). Significant matches that identify a queried protein as being in a pfam family (or as having a particular pfam domain) are those in which the bit score is greater than or equal to the gathering threshold for the Pfam domain. Expectation values (e values) can also be used as a criterion for inclusion of a queried protein in a pfam or for determining whether a queried protein has a particular pfam domain, where low e values (much less than 1.0, for example less than 0.1, or less than or equal to 0.01) represent low probabilities that a match is due to chance.

A "conservative variant" of a polypeptide is a polypeptide having one or more conservative amino acid substitutions with respect to the reference polypeptide, in which the activity (e.g. effect on transcription), affinity for co-regulators or ligands, or DNA-binding affinity of the polypeptide does not substantially differ from that of the reference polypeptide.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg and His; an "aromatic or cyclic group" including Pro, Phe, Tyr and Trp; and an "aliphatic group" including Gly, Ala, Val, Leu, Ile, Met, Ser, Thr and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained.

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences). Genes may further comprise the regulatory sequences required for their expression. Genes can be obtained from a variety of sources, including cloning from a source of interest or synthesizing from known or predicted sequence information, and may include sequences designed to have desired parameters.

The term "nucleic acid" or "nucleic acid molecule" refers to, e.g., DNA or RNA (e.g., mRNA). The nucleic acid molecules can be double-stranded or single-stranded; single stranded RNA or DNA can be the coding (sense) strand or the non-coding (antisense) strand.

The nucleic acid molecules of the present invention may be isolated or purified. As used herein, an "isolated" nucleic acid molecule or nucleotide sequence refers to a nucleic acid molecule or nucleotide sequence that is not flanked by nucleotide sequences normally flanking the gene or nucleotide sequence (as in genomic sequences) and/or has been completely or partially removed from its native environment (e.g. a cell, tissue). For example, nucleic acid molecules that have been removed or purified from cells are considered isolated. In some instances, the isolated material will form part of a composition (for example, a crude extract containing other substances), buffer system or reagent mix. In some embodiments, the nucleic acid molecules may be purified to near homogeneity, for example as determined by PAGE or column chromatography such as HPLC. An isolated nucleic acid molecule or nucleotide sequence can includes a nucleic acid molecule or nucleotide sequence that is chemically synthesized, using recombinant DNA technology or using any other suitable method. A nucleic acid contained in a vector would also be included in the definition of "isolated" as used herein. Both in vivo and in vitro RNA transcripts of an isolated DNA molecule of the present invention are also encompassed by "isolated" nucleotide sequences.

The term "codon optimized" refers to changes in the codons of a nucleotide sequence encoding a protein to those preferentially used in a particular organism such that the encoded protein is efficiently expressed in the organism of interest. In some embodiments, a nucleotide sequence encoding a protein may be codon optimized for optimal production of the protein from a host organism. As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently than the original codon(s), whether or not they are used most frequently in the organism to encode a particular amino acid.

The terms "expression vector" and "expression construct" refer to a nucleic acid molecule that has been generated via human intervention, including by recombinant means and/or direct chemical synthesis, with a series of specified nucleic acid "expression control elements" that permit transcription and/or translation of a particular nucleic acid in a host cell. The expression vector can be a plasmid, a part of a plasmid, a viral construct, a nucleic acid fragment, or the like, or a combination thereof.

An "expression cassette," as used herein, refers to a nucleotide sequence encoding a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc. "Operable linkage" or "operably linked" refers to a functional linkage between two nucleic acid sequences, such as a control sequence (such as a promoter) and the linked sequence (such as a sequence that encodes a protein and/or functional RNA). A promoter is in operable linkage with a nucleic acid sequence if it can mediate transcription of the nucleic acid sequence.

"Stringency conditions" for hybridization of nucleotide sequences refer to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity, which is less than perfect, e.g., 60%, 75%, 85%, 95% or more. For example, certain high stringency conditions can be used which distinguish perfectly complementary nucleic acids from those of less complementarity.

"High stringency conditions", "moderate stringency conditions", and "low stringency conditions" for nucleic acid hybridizations are explained in Current Protocols in Molecular Biology (2011) (John Wiley & Sons). The exact conditions which determine the stringency of hybridization depend not only on ionic strength (e.g. 0.2×SSC, 0.1×SSC, etc.) of the wash buffers, temperature (e.g. 23° C., 42° C., 68° C., etc.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary hybridization conditions are described in Krause (1991) *Methods in Enzymology*, 200, 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Examples of progressively higher stringency conditions include, after hybridization, washing with 0.2×SSC and 0.1% SDS at about room temperature (low stringency conditions); washing with 0.2×SSC and 0.1% SDS at about 42° C. (moderate stringency conditions); and washing with 0.1×SSC at about 68° C. (high stringency conditions). Washing can be carried out using only one of these conditions, e.g. high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example.

"Substantially free" is not intended to mean that other components beyond the novel nucleic acid molecules are undetectable.

A "recombinant" or "engineered" nucleic acid molecule or nucleotide sequence, or protein or polypeptide sequence, has been altered through human manipulation. As non-limiting examples, a recombinant nucleic acid molecule: (1) includes conjoined nucleotide sequences that are not conjoined in nature, (2) has been engineered using molecular cloning techniques such that it possesses and/or lacks one or more nucleotides with respect to the naturally occurring nucleic acid molecule sequence, or (3) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. Similarly, the term "recombinant protein" as used herein may refer to a protein produced by genetic engineering.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "heterologous" is used broadly in this aspect to refer to nucleic acid molecules or proteins introduced into a host cell, wherein said nucleic acid molecules or proteins are derived from a different strain/organism. A heterologous gene may have an equivalent in the transformed host, i.e., a gene which normally performs the same or a similar function, or the heterologous gene may encode a protein that does not have an endogenous homolog in the host strain/organism. When referring to a gene regulatory sequence or to an auxiliary nucleic acid sequence used for maintaining or manipulating a gene sequence (e.g. a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and reintroduced into a host cell is considered "non-native."

The terms "releasing" and "secreting," as used herein, are used interchangeably to refer to active and/or passive mechanisms to transport substances across the cell membrane. Examples of such transport mechanisms include, but are not limited to, passive diffusion, gradient diffusion, facilitated diffusion, active transport, and combinations thereof.

A transporter as used herein is a protein or protein complex that mediates the movement of a compound from one side of a biological membrane to the other. Transporters that use ATP hydrolysis, a proton motive force, or a sodium motive force to supply the energy for translocating a compound across the cell membrane to the exterior of a cell may be referred to "efflux pumps". Prokaryotic transporters of interest include multidrug resistance (MDR) transporters, that include primary transporters (ABC efflux pumps) that hydrolyze ATP and secondary transporters (e.g., MFS, SMR, MATE, RND, and PET efflux pumps) that use either a proton motive force or a sodium motive force for energy. Another type of transport system is a protein secretion system, for example, a prokaryotic Type I, Type II, Type III, Type IV, Type V, or Type VI secretion system.

The terms "recombinant," "engineered" or "genetically engineered," when applied to host cells, refer to cells that have been manipulated by introduction of a non-native (e.g., heterologous or recombinant) nucleic acid sequence into the host cell, or deletion of a native nucleic acid sequence from the host cell, and include, e.g., gene knockouts; targeted mutations and gene replacement; promoter replacement, deletion or insertion; as well as introduction of transgenes into the host cell. In some embodiments, an introduced non-native nucleic acid molecule is integrated into the genome of the recombinant/genetically engineered host. In other embodiments, an introduced non-native nucleic acid molecule is not integrated into the genome of the recombinant/genetically engineered host.

The terms "transformation," "transfection," "conjugation" and "transduction," as used in the present context, are intended to comprise a multiplicity of methods known to those skilled in the art for the introduction of foreign nucleic acids (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Transfection may be transient or stable (e.g., genomic integration). Examples of suitable methods for the transformation and/or transfection of host cells, e.g. can be found in Molecular Cloning—A Laboratory Manual (2010), Cold Spring Harbor Laboratory Press.

The term "culturing" refers to the intentional fostering of growth (e.g. increases in cell size, cellular contents and/or cellular activity, (such as production of biomolecules)) and/or propagation (e.g. increases in cell numbers via mitosis) of one or more cells by use of selected and/or controlled conditions. The combination of both growth and propagation may be termed proliferation. Nonlimiting examples of selected and/ or controlled conditions can include the use of a defined medium (with known characteristics such as pH, ionic strength and/or carbon source), specified temperature, oxygen tension, carbon dioxide levels, growth in a bioreactor, or the like, or combinations thereof.

The term "bioreactor" refers to an enclosure or partial enclosure in which cells (e.g., microalgal cells) are cultured, optionally in suspension and, when suspended, preferably in an aqueous liquid. The bioreactor can be used to culture cells through the various phases of their physiological cycle.

Alcohol-Forming Acyl-ACP Reductases

The fatty acid biosynthesis pathway is highly conserved in prokaryotes and in the chloroplasts of eukaryotic algae and higher plants. Fatty acid biosynthesis is initiated by the conversion of acetyl-CoA to malonyl-CoA, catalyzed by acetyl-CoA carboxylase (ACCase). Malonyl-CoA is then converted to malonyl-ACP, catalyzed by malonyl-CoA-ACP transacylase (FabD). Malonyl-ACP is converted to acyl-ACP in a series of reactions catalyzed by the enzyme complex fatty acid synthase (FAS). The fatty acid synthase complex initiates the elongation cycle by first condensing malonyl-ACP with acetyl-ACP, catalyzed by a beta-ketoacyl-ACP synthase III (e.g., FabH). The β-ketoacyl-ACP (3-ketoacyl-ACP) formed by the FabH reaction is reduced to a β-hydroxyacyl-ACP (3-hydroxyacyl-ACP) by 3-ketoacyl-ACP reductase (e.g. FabG). The β-hydroxyacyl-ACP is then acted on by a β-hydroxyacyl-ACP dehydratase (e.g. FabA, FabZ) to form trans-2-enoyl-ACP, which in turn is reduced by enoyl-ACP reductase (e.g. Fab I, Fab K, FabL) to form the 2 carbon-elongated acyl-ACP product. Subsequent cycles are initiated by a beta-ketoacyl-ACP synthase I or II (e.g., FabB or FabF) catalyzed condensation of malonyl-ACP with acyl-ACP. The cycles of condensation, reduction, dehydration, and reduction are repeated, with each cycle adding two carbons from malonyl-ACP, until the acyl chain is transferred to another molecule (e.g. glycerol 3-phosphate) by a transacylase, or cleaved from ACP by a thioesterase, such as FatA or FatB, in chloroplasts.

Unlike plant chloroplasts, cyanobacteria do not produce free fatty acids, and unlike $E.\ coli$ and other heterotrophic bacteria, cyanobacteria do not produce acyl-CoA. After fatty acid elongation, an acyl transferase can transfer an acyl chain covalently bound to acyl carrier protein to a glycerol backbone to produce membrane lipids.

To produce fatty acid derivatives such as fatty alcohols and fatty acid esters in cyanobacteria, it is typically necessary to introduce several enzymes to first produce acyl-CoA and to then convert the acyl-CoA to the desired end product (e.g., an alcohol, aldehyde, alkane, alkene, or wax ester). As illustrated in FIG. 6, a fatty acid thioesterase (e.g., acyl-ACP thioesterase, 3.1.2.20, an acyl-CoA thioesterase (e.g., EC 3.1.1.2), or a 4-hydroxybenzoyl thioesterase, (e.g., 3.1.2.23)) can be introduced to hydrolyze the acyl-ACP thioester, thus liberating free fatty acid. An acyl-CoA synthetase (e.g., 6.2.1.3) can be introduced to convert free fatty acids to acyl-CoA.

If fatty aldehydes and/or alkanes are the desired end product, an aldehyde-forming reductase (e.g., aldehyde-forming acyl-CoA reductase, 1.2.1.42 or 1.2.1.50; see also U.S. Pat. No. 6,143,538) may be introduced to reduce acyl-CoA to fatty aldehydes; additionally or alternatively, a carboxylic acid reductase (e.g., as disclosed in WO 2010/135624 or WO 2010/042664) may be introduced to reduce free fatty acids to fatty aldehydes. Further, a fatty alcohol oxidase (e.g., 1.1.3.20) or a fatty alcohol dehydrogenase (e.g., 1.1.1.164) may be introduced to convert fatty alcohols to fatty aldehydes. Fatty aldehydes may be processed further to produce alkanes with the introduction of a fatty aldehyde decarbonylase (e.g., 4.1.99.5).

If fatty alcohols, alkenes and/or wax esters are the desired end product, an alcohol-forming fatty acyl reductase (e.g., alcohol-forming acyl-CoA reductase, 1.2.1.50) may be introduced. Further, a fatty aldehyde reductase may be introduced to reduce fatty aldehydes to fatty alcohols. Fatty alcohols may be processed further to alkenes with the introduction of fatty alcohol dehydratase and/or with catalytic dehydration. Wax esters may be formed by introducing wax synthase to catalyze condensation of a fatty alcohol with a fatty acyl thioester.

Figure 7:
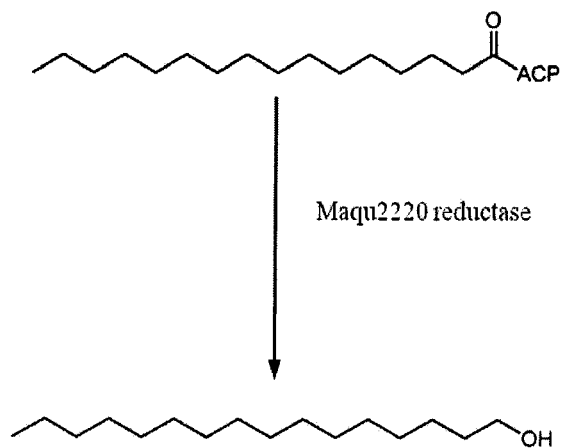
FIG. 7 is a schematic representation of a metabolic pathway for making fatty alcohols directly from acyl-ACP.

As embodied by the present invention, it has now been found that certain enzymes, e.g., Maqu_2220 acyl-ACP reductase and Hch_05075 acyl-ACP reductase, are able to convert acyl-ACP directly to fatty alcohols (FIG. 7). Such enzymes are referred to herein as "alcohol-forming acyl-ACP reductases". Maqu_2220 was previously characterized as an aldehyde reductase (see, e.g., Wahlen et al., $Appl.\ Environ.\ Microbiol.$ 75:2758-2764 (2009) and U.S. Patent Publication 2010/0203614). Here it is shown that the expression of Maqu_2220 or Hch_05075 in both an $E.\ coli$ fadD mutant strain that does not produce the FadD acyl-CoA synthetase, and in $Synechocystis$ sp. PCC 6803, a strain unable to naturally synthesize acyl-CoA or fatty alcohols, results in fatty alcohol production. Further, expression of either Maqu_2220 or Hch_05075 in $Synechocystis$ sp. PCC 6803 resulted in acyl-CoA-independent fatty alcohol production in the absence of expression of an exogenous acyl-ACP thioesterase, an exogenous acyl-CoA thioesterase, an exogenous acyl-CoA synthetase, and an exogenous aldehyde-forming acyl-ACP reductase.

In some embodiments, alcohol-forming acyl-ACP reductases used in the invention have a sequence identity of at least, e.g., 40%, 50%, 60%, 70%, 75%, 80%, 85%, 86%, 87%, 88%, 89%, 90%, 91%, 92%, 93%, 94%, 95%, 96%, 97%, 98%, 99% or 100% to a corresponding alcohol-forming acyl-ACP reductase from $Marinobacter\ aquaeolei$ (e.g., $M.\ aquaeolei$ VT8 Maqu_2220; SEQ ID NO: 2), $Hahella\ chejuensis$ (e.g., $H.\ chejuensis$ Hch_05075; SEQ ID NO: 4), $Marinobacter\ algicola$ (e.g., MDG893_11561; SEQ ID NO: 6), $Marinobacter\ adhaerens$ (e.g., HP15_810; SEQ ID NO: 8), or an $Oceanobacter$ species (e.g., RED65_09894; SEQ ID NO: 10), or a functional fragment thereof. For example, an alcohol-forming acyl-ACP reductase used in the invention can have a sequence identity of at least 90% to $M.\ aquaeolei$ VT8 Maqu_2220 (SEQ ID NO: 2) or a functional fragment thereof. Alternatively, an alcohol-forming acyl-ACP reductases used in the invention can have a sequence identity of at least 90% to $H.\ chejuensis$ Hch_05075 (SEQ ID NO: 4) or a functional fragment thereof. In yet further alternatives, an alcohol-forming acyl-ACP reductase used in the invention can have a sequence identity of at least 90% to MDG893_11561 (SEQ ID NO: 6) or a functional fragment thereof, HP15_810 (SEQ ID NO: 8) or a functional fragment thereof, or RED65_09894 (SEQ ID NO: 10) or a functional fragment thereof. Methods of demonstrating and measuring the activity of an alcohol-forming reductase protein are well known (for example, measuring rates/levels of fatty alcohol production using, e.g., gas chromatography-mass spectrometry, liquid chromatography-mass spectrometry, ion chromatography-mass spectrometry, pulsed amperometric detection, UV/VIS spectroscopy, etc., spectrophotometric assays to monitor substrate reduction rates, etc.).

In some embodiments, the alcohol-forming acyl-ACP reductase is encoded by an isolated nucleic acid molecule comprising a nucleic acid sequence having at least about 30%, 40%, 50%, 60%, 70%, 75%, 80%, 85%, 86%, 87%, 88%, 89%, 90%, 91%, 92%, 93%, 94%, 95%, 96%, 97%, 98%, 99% or 100% sequence identity to a corresponding nucleic acid sequence encoding an alcohol-forming acyl-ACP reductase from *Marinobacter aquaeolei* (e.g., *M. aquaeolei* VT8 Maqu_2220; SEQ ID NO: 1), *Hahella chejuensis* (e.g., *H. chejuensis* Hch_05075; SEQ ID NO: 3), *Marinobacter algicola* (e.g., MDG893_11561; SEQ ID NO: 5), *Marinobacter adhaerens* (e.g., HP15_810; SEQ ID NO: 7), or an *Oceanobacter* species (e.g., RED65_09894; SEQ ID NO: 9).

In some embodiments, the alcohol-forming acyl-ACP reductase used in the methods of the invention is a microbial acyl-ACP reductase and in some embodiments can be a prokaryotic acyl-ACP reductase. In some embodiments an alcohol-forming acyl-ACP reductase expressed in a microbial host has at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% sequence identity to an alcohol-forming acyl-ACP reductase from a marine bacterium, i.e., a bacterium that naturally occurs in a marine environment, or to a functional fragment thereof. In certain embodiments, the marine bacterium is a species of *Marinobacter*, e.g., *M. algicola*, *M. alkaliphilus*, *M. aquaeolei*, *M. adhaerens*, *M. arcticus*, *M. bryozoorum*, *M. daepoensis*, *M. excellens*, *M. flavimaris*, *M. guadonensis*, *M. hydrocarbonoclasticus*, *M. koreensis*, *M. lipolyticus*, *M. litoralis*, *M. lutaoensis*, *M. maritimus*, *M. sediminum*, *M. squalenivirans*, *M. vinifirmus*, *M.* sp. 1369, etc. In particular embodiments, the marine bacterium is *M. aquaeolei* strain VT8 or *M. hydrocarbonoclasticus*. In certain embodiments, the marine bacterium is e.g., *Meptuniibacter caesariensis* sp. strain MED92, *Reinekea* sp. strain MED297, *Marinomonas* sp. strain MED121, *Marinobacter* sp. strain ELB17 or unnamed gammaproteobacterium strain HTCC2207. In certain embodiments, the marine bacterium is of the order *Oceanospirillilales*, e.g., the family *Oceanospirillaceae*, e.g., the genus *Hahella*, e.g., *Hahella ganghwensis*, *Hahella antarctica*, or *Hahella chejuensis*, or the genus *Oceanobacter*, e.g., the species *Oceanobacter* sp. strain RED65, *Oceanobacter kriegii* or *Oceanobacter* sp. strain WH099.

In some embodiments, an alcohol-forming acyl-ACP reductase expressed by a recombinant microorganism as provided herein has at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% sequence identity to a corresponding alcohol-forming acyl-ACP reductase from an organism such as *Vitis vinifera* (GenBank Accession No. CA022305.1 or CA067776.1), *Desulfatibacillum alkenivorans* (GenBank Accession No. NZ_ABII01000018.1), *Stigmatella aurantiaca* (NZ_AAMD01000005.1), *Phytophthora ramorum* (GenBank AccessionNo.: AAQXO1OO1 105.1), *Simmondsia chinensis* (jojoba), *Acinetobacter calcoaceticus*, etc.

In some embodiments, an alcohol-forming acyl-ACP reductase produced by a recombinant microorganism has at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% sequence identity to FARJVIac (from marine actinobacterium strain PHSC20C1), FARJVC (JCVI_ORF_1096697648832, GenBank Accession No. EDD40059.1; from a marine metagenome), FAR_Fer (JCVI_SCAF_1101670217388; from a marine bacterium found at a depth of 12 m in an upwelling in the area of Fernandina Island, the Galapagos Islands, Ecuador), FAR Key (JCVI_SCAF_1097205266585, from a marine bacterium found at a depth of 1.7 m off the coast of Key West Fla.) and FAR_Gal (JCVI_SCAF_1101670289386, at a depth of 0.1 m at Isabella Island, Galapagos Islands, Ecuador).

In some embodiments, alcohol-forming acyl-ACP reductases may be identified using Hidden Markov Models ("HMMs") based on pattern similarity to a set of known alcohol-forming acyl-ACP reductase sequences (see, e.g., http://pfam.sanger.ac.uk/). For example, an acyl-ACP reductase that can be used in the methods provided herein may be identified as having, e.g., a pfam PF07993 "NAD binding 4" domain of between about 200 and 400 amino acids, and/or C-terminal to the PF07993 domain, a pfam PF03015 "sterile" domain of between about 50 and about 150 amino acids. In some embodiments, the bit score for matching of a reductase with the pfam model is greater than the gathering cutoff for the domain, or, e.g., greater than 20.1 for the match with the PF07993 domain and/or greater than 21.4 for the match with the PF03015 domain.

In some embodiments, a protein known or suspected of having FAR activity, e.g., acyl-CoA reductase activity, is found to additionally or alternatively have alcohol-forming acyl-ACP reductase activity. Proteins known or suspected of having FAR activity include, but are not limited to, Maqu_2220, Hch_05075, HP15_810, MDG893_11561 and RED65_09894, and can further include, for example, bfar from *Bombyx mmori*, jjfar from *Simmondsia chinensis*, an acyl-CoA reductase from *Titicum aestivum*, mfar1 from *Mus musculus*, mfar2 from *Mus musculus*, hfar from *H. sapiens*, FARXIII from *Ostrinia scapulalis*, MS2 from *Z. mays*, or MS2, FAR4_3, FAR6, CER4 from *Arabidopsis thaliana*, etc.

The above-described alcohol-forming acyl-ACP reductases and nucleic acids encoding them may be used in any of the methods of producing a fatty alcohol described herein.

Methods of Producing a Fatty Alcohol

The invention provides acyl-CoA-independent methods of producing a fatty alcohol in a recombinant host cell, e.g., any of the recombinant host cells described herein that express an alcohol-forming acyl-ACP reductase. In some embodiments, the recombinant host cell comprises any of the isolated nucleic acid molecules and/or vectors described herein. In various embodiments, the method comprises the steps of:

culturing a recombinant host cell in a suitable culture medium, wherein the recombinant host cell does not produce acyl-CoA, further wherein the recombinant host cell comprises a non-native nucleic acid sequence which produces an alcohol-forming acyl-ACP reductase upon expression in the host cell, and allowing expression of the nucleic acid sequence, wherein the expression results in the production of at least 0.5 mg of fatty alcohols per liter of culture in a seven day culture period.

The alcohol-forming acyl-ACP reductases produced by a recombinant microorganism in the methods of the present invention are able to use acyl-ACP as a substrate instead of, or in addition to, acyl-CoA. In some embodiments, the recombinant host cell does not endogenously produce acyl-CoA. For example, the recombinant host can be a cyanobacterial species that does not naturally produce acyl-CoA. In some embodiments, a species that does not naturally produce acyl-CoA that is used as a producing strain for use in the methods provided herein is not genetically engineered to produce acyl-CoA. In other embodiments, the recombinant host cell endogenously produces acyl-CoA but is engineered to eliminate acyl-CoA production. Additionally or alternatively, the recombinant host cell does not express, e.g., an acyl-ACP thioesterase, an acyl-CoA thioesterase and/or an acyl-CoA synthetase.

In some embodiments, the recombinant host cell does not produce an acyl-CoA synthetase. In some embodiments, the recombinant host cell does not include an exogenous gene encoding an acyl-CoA synthetase. In some embodiments, the host cell does not include an endogenous gene encoding an acyl-CoA synthetase. For example, based on analysis of genes from cyanobacterial species having sequenced genomes, it has been determined that these species lack acyl-CoA synthetase genes (Kaczmarzyk and Fulda (2010) *Plant Physiol.* 152: 1598-1610). In alternative embodiments the host cell may have an attenuated acyl-CoA synthetase gene, such that the enzyme is inactive, is not substantially produced, or is not produced.

Additionally, the recombinant host cell in some examples can be a cell that does not produce an acyl-ACP thioesterase or an acyl-CoA thioesterase. For example, the recombinant host cell can lack an exogenous gene encoding an acyl-ACP thioesterase or an exogenous gene encoding an acyl-CoA thioesterase. For example, the recombinant host cell can lack both an exogenous gene encoding an acyl-ACP thioesterase and an exogenous gene encoding an acyl-CoA thioesterase. The recombinant host cell can additionally be a cell that lacks an endogenous acyl-ACP thioesterase gene or an endogenous acyl-CoA thioesterase gene. The host microorganism can lack both an endogenous acyl-ACP thioesterase gene and an endogenous acyl-CoA thioesterase gene. For example, cyanobacterial genomes do not include genes encoding acyl-ACP thioesterases or acyl-CoA thioesterases. In alternative embodiments, the host cell may have an attenuated acyl-ACP thioesterase gene and/or an attenuated acyl-CoA thioesterase gene, such that one or both of the enzymes are produced at a reduced level, are not substantially produced, or are not produced.

The alcohol-forming acyl-ACP reductase produced by the host microorganism can be any disclosed herein, for example, any disclosed in the preceding or following sections. For example, the host microorganism can include a non-native nucleic acid molecule that encodes an acyl-ACP reductase from a microbial source, such as a bacterial, fungal, heterokont, cyanobacterial, or microalgal species. The acyl-ACP reductase produced by the recombinant microorganism can be a prokaryotic acyl-ACP reductase, i.e., the source of the gene or protein sequence is a prokaryotic species, e.g., a *gammaproteobacterium, Limnobacter,* or *Mycobacterium* species. In some embodiments, the acyl-ACP reductase expressed by the recombinant microorganism can be from a marine microorganism, such as, for example, a *Marinobacter, Alcanivorax, Hahella,* or *Oceanobacter* species.

In some embodiments, the non-native nucleic acid sequence encodes an alcohol-forming acyl-ACP reductase from a marine bacterium, i.e., a bacterium that naturally occurs in a marine environment. In some embodiments, the alcohol-forming acyl-ACP reductase encoded by a non-native nucleic acid sequence has at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% sequence identity to an alcohol-forming acyl-ACP reductase from *Marinobacter aquaeolei* (e.g., *M. aquaeolei* VT8 Maqu_2220; SEQ ID NO: 2), *Hahella chejuensis* (e.g., *H. chejuensis* Hch_05075; SEQ ID NO: 4), *Marinobacter algicola* (e.g., MDG893_11561; SEQ ID NO: 6), *Marinobacter adhaerens* (e.g., HP15810; SEQ ID NO: 8), or an *Oceanobacter* species (e.g., RED65_09894; SEQ ID NO: 10), or a functional fragment thereof. For example, the alcohol-forming acyl-ACP reductase can be encoded by a non-native nucleic acid sequence has at least about 85% sequence identity to Maqu_2220 (SEQ ID NO: 2), or at least about 90% sequence identity to Maqu_2220 (SEQ ID NO: 2). Alternatively, the alcohol-forming acyl-ACP reductase can be encoded by a non-native nucleic acid sequence has at least about 85% sequence identity to Hch_05075 (SEQ ID NO: 4), or at least about 90% sequence identity to Hch_05075 (SEQ ID NO: 4). In further alternatives, the alcohol-forming acyl-ACP reductase can be encoded by a non-native nucleic acid sequence has at least about 85% sequence identity to MDG893_11561 (SEQ ID NO: 6), HP15_810 (SEQ ID NO: 8), or RED65_09894 (SEQ ID NO: 10), or at least about 90% sequence identity to MDG893_11561 (SEQ ID NO: 6), HP15_810 (SEQ ID NO: 8), or RED65_09894 (SEQ ID NO: 10).

A recombinant host cell used in the methods of the invention may comprise any of the nucleic acid sequences encoding an alcohol-forming acyl-ACP reductase as described herein. The nucleic acid sequence encoding the alcohol-forming acyl-ACP reductase may be codon-optimized for expression in the recombinant host cell. In some embodiments, the nucleic acid sequence encoding the alcohol-forming acyl-ACP reductase is heterologous to the recombinant host cell. In certain embodiments, the nucleic acid sequence is integrated into a chromosome of the recombinant host cell. In certain embodiments, the nucleic acid sequence may be present on an episome in the recombinant host cell, which may or may not replicate within the host cell. In certain embodiments, the nucleic acid sequence is present in a vector in the recombinant host cell, and may optionally be operably linked to a promoter and/or enhancer (e.g., a heterologous promoter and/or enhancer), which in some embodiments may be regulatable. In certain embodiments, the promoter and/or enhancer are inducible, and the method may further comprise the step of inducing expression of the alcohol-forming acyl-ACP reductase.

In some embodiments, the conversion of acyl-ACP to fatty alcohol may occur via synthesis of a fatty aldehyde, wherein an aldehyde-forming acyl reductase (e.g., an aldehyde-forming acyl-ACP reductase) expressed in the host cell first reduces acyl-ACP to a fatty aldehyde. For example, the host cell can be engineered to overexpress a homologous, for example, an endogenous, aldehyde-forming acyl reductase (e.g., by inserting promoter and/or enhancer transcriptional control elements near the aldehyde-forming reductase gene) in addition to an alcohol-forming acyl-ACP reductase. Additionally or alternatively, the host cell may be engineered to express an exogenous aldehyde-forming acyl reductase.

In some embodiments, the recombinant host cell may comprise an exogenous gene encoding an aldehyde-forming acyl reductase, such as for example, a carboxylic acid reductase (see, for example, WO 2010/135624 and WO 2010/042664) or an aldehyde-forming acyl-ACP reductase such as but not limited to those disclosed in WO 2009/140696 and WO 2011/066137. For example, the recombinant host cell may comprise, in addition to a gene encoding an alcohol-forming acyl-ACP reductase, an aldehyde-forming acyl-ACP reductase that has at least 50%, 60%, 70%, 80%, 90% or 95% sequence identity to an aldehyde-forming reductase, e.g., as disclosed in WO 2009/140696 or WO 2011/066137, such as, for example, any of the reductases having the accession numbers AAM82647; AAM82647; BAD78241; ABA22149; BAB76983; ZP_03763674; ACL42791; ZP_01628095; ZP_01619574; YP_001865324; YP_721978; NP_682102; YP_001518341; YP_002371106; ZP_05027136; ZP_03273554; NP_442146; ZP_01728620; ZP_05039135; YP_001802846; NP_926091; YP_001660322; ZP_00516920; CAO90781; ZP_01085337; YP_001227841; ABD96327; NP_897828; YP_001224378; ABD96480; ZP_01123215; ABB92249; ZP_01079773; YP_377636; NP_874926; NP_895058; ABD96274; ABD96442; ZP_01469469; ZP_05045052; YP_001014416; YP_001010913; YP_381056;

YP_001550421; NP_892651; YP_001090783; ZP_01472595; YP_293055; ZP_05138243; YP_731192; YP_001483815; YP_001008982; YP_473896; YP_478638; or YP_397030. In some embodiments the recombinant host cell is a cyanobacterium, and the recombinant cyanobacterium includes, in addition to a non-native nucleic acid molecule encoding an alcohol-forming acyl-ACP reductase, an exogenous gene encoding an aldehyde-forming acyl-ACP reductase, where the aldehyde-forming acyl-ACP reductase can be from a cyanobacterial species, and may be from the same species as the host microorganism, or may be from a different cyanobacterial species.

In some embodiments, the recombinant host cell expresses a homologous fatty aldehyde-forming reductase, which may be, e.g., an aldehyde-forming acyl-ACP reductase. In certain embodiments, the recombinant host cell is engineered to overexpress an endogenous aldehyde-forming reductase, e.g., by engineering the recombinant host cell to comprise a heterologous promoter operably linked to the endogenous nucleic acid sequence encoding the aldehyde-forming reductase. The reductase can be, e.g., any aldehyde-forming acyl-ACP reductase endogenous to the host cell, and may be, for example, an aldehyde-forming acyl-ACP reductase having at least 50%, 60%, 70%, 80%, 90%, or 95% sequence identity to any of the reductases having the accession numbers AAM82647; AAM82647; BAD78241; ABA22149; BAB76983; ZP_03763674; ACL42791; ZP_01628095; ZP_01619574; YP_001865324; YP_721978; NP_682102; YP_001518341; YP_002371106; ZP_05027136; ZP_03273554; NP_442146; ZP_01728620; ZP_05039135; YP_001802846; NP_926091; YP_001660322; ZP_00516920; CAO90781; ZP_01085337; YP_001227841; ABD96327; NP_897828; YP_001224378; ABD96480; ZP_01123215; ABB92249; ZP_01079773; YP_377636; NP_874926; NP_895058; ABD96274; ABD96442; ZP_01469469; ZP_05045052; YP_001014416; YP_001010913; YP_381056; YP_001550421; NP_892651; YP_001090783; ZP_01472595; YP_293055; ZP_05138243; YP_731192; YP_001483815; YP_001008982; YP_473896; YP_478638; or YP_397030.

In certain embodiments, the heterologous promoter operably linked to the homologous (in particular embodiments, endogenous) aldehyde-forming acyl-ACP reductase is regulatable. In particular embodiments, the promoter is inducible, and the method further comprises the step of inducing expression of the homologous or endogenous aldehyde-forming reductase.

In certain embodiments, the recombinant host cell does not express an aldehyde-forming reductase (e.g., aldehyde-forming acyl-CoA reductase, aldehyde-forming acyl-ACP reductase or carboxylic acid reductase). In certain embodiments, the recombinant host cell does not express an aldehyde-forming acyl-CoA reductase or a carboxylic acid reductase. In particular embodiments, the recombinant host cell does not express a non-native, e.g., exogenous, aldehyde-forming reductase.

A suitable culture medium can be any appropriate to the host microorganism that includes nutrients sufficient for production of fatty alcohols during the culture period, and preferably but optionally, growth of the culture (i.e., increase in cell division and/or biomass of the culture). Preferably, the medium includes a suitable carbon source, such as, for heterotrophic growth, a carbohydrate (sugar, sugar-alcohol, organic acid, etc.). The growth media can further include one or more metals, vitamins, cofactors, amino acids, peptides, lipids, salts, buffering agents, and/or chelators. Media recipes for the growth of various species of microorganisms are available and can be optimized for growth of the culture or production of biomolecules. For photosynthetic growth, the culture medium can be a medium that does not include a substantial amount of a reduced carbon source, where the photosynthetic host microorganism uses inorganic carbon, such as, for example, carbon dioxide, carbonic acid, or a carbonate, bicarbonate, or hydrogen carbonate compound, as substantially the sole source of carbon for incorporation into products such as fatty alcohols.

The recombinant host cell may be any recombinant host cell described herein. Use of acyl-ACP as a substrate allows for the omission of certain steps required for the conversion of acyl-CoA to fatty alcohol. In some embodiments, the recombinant host cell does not include an endogenous gene encoding at least one of an acyl-CoA synthetase, an acyl-CoA dehydrogenase, an acyl-ACP thioesterase, or an acyl-CoA thioesterase. In some embodiments, the recombinant host cell does not include an endogenous gene encoding any of an acyl-CoA synthetase, an acyl-ACP thioesterase, and an acyl-CoA thioesterase. Advantageously, genes encoding the enzymes that catalyze these steps do not need to be engineered into a recombinant host cell that does not endogenously express these enzymes. In some embodiments, the recombinant host cell does not include an endogenous or exogenous gene encoding any of an acyl-CoA synthetase, acyl-ACP thioesterase, an acyl-CoA thioesterase, and an acyl-CoA dehydrogenase.

In some embodiments, the recombinant host cell is a recombinant photosynthetic microorganism.

In further embodiments, the method comprises the steps of:
culturing a recombinant photosynthetic microorganism in a suitable culture medium, wherein the recombinant photosynthetic microorganism comprises a non-native nucleic acid sequence which produces an alcohol-forming acyl-ACP reductase upon expression in the photosynthetic microorganism; and
allowing expression of the nucleic acid sequence, wherein the expression results in the production of at least 0.5 mg of fatty alcohols per liter of culture in a seven day culture period.

The recombinant photosynthetic microorganism may be cultured photoautotrophically or mixotrophically, where the recombinant photosynthetic microorganism is exposed to light for at least a portion of the culture period. In some embodiments, the recombinant microorganism is cultured phototrophically. In particular embodiments, the culture medium includes inorganic carbon as substantially the sole carbon source. For example, an inorganic carbon source such as $CO_2$, carbonic acid, or a carbonate compound can be substantially the sole source of carbon in the culture, providing the carbon for incorporation into biomolecules, including fatty alcohols.

In some embodiments, the host microorganism can be a photosynthetic microorganism such as a cyanobacterial strain that does not include an endogenous gene encoding an acyl-CoA synthetase, or in alternative embodiments the recombinant photosynthetic microorganism may have an attenuated acyl-CoA synthetase gene, or expression of the acyl-CoA synthetase gene may be downregulated by the use of antisense, ribozymes, or RNAi constructs. Additionally or alternatively, the recombinant host cell does not include an exogenous gene encoding an acyl-CoA synthetase.

In some embodiments, the recombinant photosynthetic microorganism does not produce an acyl-ACP thioesterase or an acyl-CoA thioesterase. For example, in some embodiments, the recombinant photosynthetic microorganism does not include an exogenous gene encoding an acyl-ACP thioesterase or an acyl-CoA thioesterase. Additionally, in some embodiments, the host cell can be, for example, a cyanobacterial species that does not include an endogenous gene encoding an acyl-ACP thioesterase or an acyl-CoA thioesterase, or in alternative embodiments the host cell may have an attenuated acyl-ACP thioesterase gene and/or an attenuated acyl-CoA thioesterase gene, or thioesterase gene expression may be inhibited by antisense, ribozymes, or RNAi constructs such that the enzymes are not produced.

The recombinant photosynthetic microorganism in some examples can be a recombinant cyanobacterium. In particular embodiments, the cyanobacterium is selected from a list including, but not limited to, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus* species. In some examples, the recombinant photosynthetic microorganism can be a *Synechococcus, Synechocystis,* or *Thermosynechococcus* species. Alternatively the recombinant photosynthetic microorganism can be a *Cyanobacterium, Cyanobium,* or *Cyanothece* species. In yet further alternatives, the recombinant photosynthetic microorganism can be a *Gloeobacter, Leptolyngbya,* or *Lyngbya* species.

In certain embodiments, the recombinant photosynthetic microorganism is a recombinant eukaryotic microalga. In particular embodiments, the eukaryotic microalga is selected from a list including, but not limited to *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox* species.

Because the alcohol-forming acyl-ACP reductases of the present invention use acyl-ACP as a substrate, increasing acyl-ACP concentration in the recombinant host cell may result in increased fatty alcohol production. In some embodiments, acyl-ACP production is upregulated in the recombinant host cell. In certain embodiments, the recombinant host cell expresses or produces at least one exogenous polypeptide that directly or indirectly increases acyl-ACP production, such as, for example, a beta-ketoacyl synthetase, an acetyl-CoA carboxylase, a malonyl-CoA:ACP transacylase, acyl carrier protein, or an acyl-ACP synthetase. In some embodiments, in which the host microorganism is a photosynthetic microorganism, carbon fixation is upregulated in the recombinant host cell. In certain embodiments, the recombinant host cell expresses or produces at least one exogenous polypeptide that increases carbon fixation, such as, for example, a ribulose 1,5-bisphosphate carboxylase polypeptide or a phycobiliprotein (e.g., phycocyanin). In certain embodiments, the recombinant host cell expresses or produces an exogenous gene encoding a transmembrane transporter or a component of a transmembrane transporter, including but not limited to those disclosed herein.

In some embodiments, the recombinant host cell is engineered to attenuate or eliminate the expression of one or more beta-oxidation pathway enzymes. In certain embodiments, the recombinant host cell is engineered to attenuate or eliminate expression of at least one of glycerol-3-phosphate dehydrogenase, acetaldehyde-CoA dehydrogenase, pyruvate dehydrogenase, and acetate kinase.

Mutations to attenuate or eliminate expression of known genes can be introduced either by recombinant or non-recombinant methods. The genes may be targeted specifically by disruption, deletion, replacement, or generation of antisense sequences, by use of micro RNAs or shRNA constructs, generation of ribozymes and/or other recombinant approaches known to the practitioner. Inactivation of the genes can additionally or alternatively be accomplished by random mutation techniques such as exposure to UV and/or chemical mutagens followed by screening of the cells for successful mutants. Additionally or alternatively, the proteins encoded by the genes can be inhibited by intracellular generation of appropriate antibodies, intracellular generation of peptide inhibitors, or the like, or some combination thereof.

In some embodiments, the methods of the invention produce at least 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/L of one or more fatty alcohols/culture over a culture period of 1, 2, 3, 4, 5, 6, 7, 8, 9, 10, 11, 12, 13, or 14 days. In certain embodiments, the recombinant host cell produces at least 1, 2, 5, or 10 mg/L of one or more fatty alcohols/culture over a period of 7 days, or an average of about 0.1, 0.2, 0.5, 1, or 1.5 mg/L of one or more fatty alcohols/culture per day over a culture period of from one to thirty days. In a particular embodiment, the methods of the invention produce an average of at least 0.5 mg/L of one or more fatty alcohols/culture over a seven day culture period. For example, the methods of the invention can provide between about 0.5 mg/L and about 10 g/L of one or more fatty alcohols/culture over a period of from about one to about 30 days, or can provide between about 1 mg/L and about 10 g/L over a period of from about one to about 30 days, such as from about three to about ten days. In some embodiments, the methods of the invention can provide between about 5 mg/L and about 10 g/L of one or more fatty alcohols/culture over a period of from about one to about 30 days, or can provide between about 5 mg/L and about 5 g/L, between about 5 mg/L and about 1 g/L, between about 10 mg/L and about 5 g/L, between about 10 mg/L and about 2 g/L, between about 10 mg/L and about 1 g/L or between about 10 mg/L and about 500 mg/L of one or more fatty alcohols/culture, over a period of from about one to about 30 days, such as from about three to about ten days. In some embodiments, the recombinant host cell expressing an alcohol-forming acyl-ACP reductase produces an increased level of one or more fatty alcohols relative to a control host cell not expressing the alcohol-forming acyl-ACP reductase.

In some embodiments, the amount of fatty alcohol produced by the recombinant host cell expressing an alcohol-forming acyl-ACP reductase is at least about 10%, 15%, 20%, 25%, 30%, 40%, 50%, 60%, 65%, 70%, 75%, 80%, 90%, 95%, 100%, 125%, 150%, 175%, 200%, 225%, 250%, 275%, 300%, 325%, 350%, 375%, 400%, 425%, 450%, 475%, 500%, 525%, 550%, 575%, 600%, 625%, 650%, 675%, 700%, 725%, 750%, 775%, 800%, 825%, 850%, 875%, 900%, 925%, 950%, 975%, or 1000% greater than the amount of fatty alcohol produced by a control host cell that does not express the alcohol-forming acyl-ACP reductase.

In some embodiments, the methods of the invention produce one or more C8-C24 fatty alcohol molecules. In certain embodiments, the fatty alcohols produced by the methods can include one or more C12-C18 fatty alcohol molecules. In certain embodiments, the fatty alcohols produced include, e.g., one or more of C6, C8, C10, C12, C14, C16, C18, C20, C22 or C24 fatty alcohol molecules, alone or in any combination. In some embodiments, at least about 80%, at least about 85%, at least about 90%, at least about 92%, at least about 95%, at least about 97% or at least about 99% by weight of the total fatty alcohols produced are C8 to C24 fatty alcohols. In some embodiments, at least about 80%, at least about 85%, at least about 90%, at least about 92%, at least about 95%, at least about 97% or at least about 99% by weight of the total fatty alcohols produced are C10 to C20 alcohols. In certain embodiments, at least about 80%, at least about 85%, at least about 90%, at least about 92%, at least about 95%, at least about 97% or at least about 99% by weight of the total fatty alcohols produced are C12 to C18 fatty alcohols.

In some embodiments, the recombinant host cell secretes at least a portion of the produced fatty alcohol into the growth media. In certain embodiments, the ratio of the amount of fatty alcohol produced to the amount of fatty alcohol secreted is less than about 10:1, 9:1, 8:1, 7:1, 6:1, 5:1, 4:1, 3:1, 2:1, 1.5:1, or can be about 1:1. The recombinant host cell may express a non-native gene that encodes a transmembrane transporter (e.g., an ATP-binding cassette, or ABC, transporter or an RND pump) to facilitate fatty alcohol secretion. In some embodiments, the transporter is encoded by at least one gene selected from a group including, but not limited to, *Arabidopsis* genes CER5, WBC11, AtMRPS, AmiS2 and AtPGP1 or fatty acid transporter (FATP) genes from *Saccharomyces, Drosophila*, mycobacterial species or mammalian species. In some embodiments, expression of a transporter protein increases the amount of a fatty alcohol or fatty alcohol derivative released from the recombinant host cell. In certain embodiments, expression of a transporter protein increases production of a fatty alcohol or fatty alcohol derivative by the recombinant host cell. In some embodiments, secretion of the fatty alcohol is regulatable. In certain embodiments, secretion of the fatty alcohol is inducible.

Secretion Systems

In further examples, the host microorganism can include, in addition to at least one non-native gene for producing a fatty acid or fatty acid derivative, a non-native gene that encodes a component of a prokaryotic transporter or secretion system. A genetically engineered microorganism that includes at least one non-native gene that encodes a component of a prokaryotic transporter or secretion system can include, for example, a non-native gene for producing a fatty acid or fatty acid derivative such as but not limited to a gene encoding an acetyl-CoA carboxylase, a malonyl type 1 fatty acid synthase, a type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, an alcohol forming acyl reductase, a wax synthase, an aldehyde decarbonylase, a fatty acid decarboxylase, a lipase, or an acyl-CoA synthetase. For example, the microorganism can be engineered to produce fatty acids, fatty alcohols, fatty aldehydes, wax esters, fatty acid esters, alkanes, or alkenes.

Nonlimiting examples of prokaryotic transporters include protein secretion systems and multidrug resistance transporters (efflux pumps), including multidrug resistance transporters that are members of the ATP-binding Cassette (ABC) transporter family, as well as secondary transporters of the Major Facilitator Superfamily (MFS), the Small Multidrug Resistance (SMR) family, the Multi Antimicrobial Extrusion (MATE) family, the putative and the Resistance-Nodulation-cell Division (RND) family.

For example, a recombinant microorganism as provided herein can include at least one non-native gene that encodes a polypeptide component of an RND transporter, such as a membrane fusion protein of an RND efflux transporter family, or an inner membrane permease protein of an RND efflux transporter family. In some examples, a recombinant microorganism is engineered to produce a free fatty acid, a fatty aldehyde, or a fatty alcohol, and includes a non-native gene encoding a membrane fusion protein of an RND efflux transporter family and a non-native gene encoding an inner membrane permease protein of an RND efflux transporter family, where the recombinant microorganism secretes at least a portion of the produced free fatty acid, fatty aldehyde, or fatty alcohol. In some embodiments, one or both genes encoding components of the RND efflux transporter are heterologous genes. Alternatively, one or both genes encoding components of the RND efflux transporter can be endogenous genes, and can be operably linked to a heterologous promoter to be overexpressed and/or inducibly expressed to facilitate secretion of the fatty acid, fatty aldehyde, fatty alcohol, or other fatty acid derivative produced by the recombinant microrgansim. In a particular example, the recombinant microorganism is a cyanobacterium engineered to include a non-native gene encoding an acyl-ACP thioesterase (see, for example, U.S. Patent Application publication 2009/0298143 and U.S. Patent Application publication 2011/020883, both incorporated herein by reference), an acyl-CoA thioesterase (see, for example WO 2010/075483, incorporated herein by reference), or a 4-HBT thioesterase (see, for example, U.S. Patent Application publication 2012/0164713, incorporated herein by reference).

In various examples, a recombinant microorganism can include a non-native gene encoding a polypeptide having at least 80%, at least 85%, at least 90%, at least 95%, at least 96%, at least 97%, at least 98%, or at least 99% to a membrane fusion protein of an RND efflux transporter family such as a membrane fusion protein of a *Pseudomonas* Mex RND transport system (e.g., a MexA, MexC, MexE, or MexX protein), or an ortholog of any thereof in another species, an *Escherichia coli* Acr transport system (e.g., AcrA protein), or an ortholog of any thereof in another species, a BpeA protein of *Burkholderia pseudomallei*, or an ortholog of any thereof in another species, etc. Additionally, a recombinant microorganism can include a non-native gene encoding an inner membrane permease protein of an RND efflux transporter family, such as a membrane permease protein of a *Pseudomonas aeruginosa* Mex RND transport system (e.g., a MexB, MexD, MexF, or MexY protein), or an ortholog of any thereof in another species, an *Escherichia coli* Acr transport system (e.g., AcrB protein), or an ortholog of any thereof in another species, a BpeB protein of *Burkholderia pseudomallei*, or an ortholog of any thereof in another species, etc.

In some examples, a recombinant microorganism includes a non-native gene encoding a polypeptide having at least 80%, at least 85%, at least 90%, at least 95%, at least 96%, at least 97%, at least 98%, or at least 99% to a membrane fusion protein of an RND efflux transporter and a non-native gene encoding a polypeptide having at least 80%, at least 85%, at least 90%, at least 95%, at least 96%, at least 97%, at least 98%, or at least 99% to a membrane permease protein of an RND efflux transporter, which optionally can be operably linked to the same heterologous promoter, for example, as an operon. Optionally, the recombinant microorganism can further include an additional non-native gene encoding a TolC protein. In particular examples, the recombinant microorganism is a prokaryotic microorganism, and can be, for example, a cyanobacterium that includes endogenous genes encoding RND efflux transporters, and the microorganism is engineered such that a regulatable promoter is inserted upstream of an operon that includes the gene encoding the membrane fusion protein and the gene encoding the membrane permease protein of an endogenous RND efflux transporter operon.

Alternatively, a recombinant microorganism as provided herein can include, in addition to a non-native gene encoding a protein that participates in the synthesis of a fatty acid or fatty acid derivative, a non-native gene encoding a component of a Type VI Secretion System (T6SS). For example, the recombinant microorganism can include a non-native gene encoding a VgrG protein of a T6SS, for example, a polypeptide having at least 80%, at least 85%, at least 90%, at least 95%, at least 96%, at least 97%, at least 98%, or at least 99% to at least 620, at least 650, or at least 680 amino acids of a VgrG protein of a *Vibrio, Pseudomonas, Burkholderia, Ersinia, Yersinia, Escherishia, Aeromonas, Shigella, Marinobacter, Photorhabdus, Mesorhizobium, Photobacteria, Xanthomonas, Ralstonia, Hahella, Geobacter, Salmonella*, or *Shewanella* species. VgrG proteins are believed to act as a puncturing device in a multiprotein assembly that mediate pathogenesis in certain bacterial species (Records (2011) MPMI 24: 751-757). Suprisingly, expression of the VgrG protein of *Pseudomonas fluorescens* in a microorganism engineered to produce free fatty acids or fatty alcohols resulted in secretion of the fatty acids or fatty acid derivatives produced by the microorganism. Most Vgr proteins include C-terminal domains that may interact with proteins of the pathogen's target cell. These domains may be dispensable for the secretion-mediating function, as apparent from Example 11, where the C-terminally truncated VgrG expressed from the library insert (FIG. 18) was able to effect secretion of fatty alcohols.

In some embodiments, the method further comprises the step of isolating the produced fatty alcohol. Fatty alcohols and other fatty acid derivatives can be recovered from the culture medium by recovery means known to those of ordinary skill in the art, such as by whole culture extraction, e.g., using appropriate (e.g., organic) solvents. Additionally or alternatively, particulate adsorbents can be employed. These may include, e.g., lipophilic particulates and/or ion exchange resins, depending on the design of the recovery method. The particulate absorbents may circulate in the separated medium and then undergo collection, and/or the medium may be passed over a fixed bed column, for example a chromatographic column, containing the particulates. The fatty alcohols and/or fatty alcohol derivatives can then be eluted from the particulate adsorbents, e.g. by the use of an appropriate solvent. In certain embodiments, the solvent may then be evaporated, followed by further processing of the isolated fatty alcohols and/or fatty alcohol derivatives to yield chemicals and/or fuels that can be used for a variety of purposes.

Isolation of the fatty alcohols and/or fatty alcohol derivatives may occur simultaneously with fatty alcohol production. In some embodiments, isolation of the fatty alcohol is continuous.

In some embodiments, recovery of fatty alcohols or fatty alcohol derivatives can be enhanced by homogenization of the host cells (via, e.g., heat, treatment with an acid or base, treatment with enzymes, osmotic shock, mechanical disruption, sonication, freeze-thaw, etc.). In some embodiments, material containing cells or cell fractions can be treated with proteases to degrade contaminating proteins. After digestion, the fatty alcohols and/or fatty alcohol derivatives may be purified from residual proteins, peptide fragments and amino acids, e.g., by centrifugation and/or filtration. The recovery method can be adapted to efficiently recover only the released fatty acids and/or fatty acid derivatives, only the fatty alcohols and/or fatty alcohol derivatives produced and stored within the cells, or both the stored and released fatty alcohols and/or fatty alcohol derivatives.

In methods that include culturing a recombinant microorganism as provided herein that expresses a transporter system or secretion system, secreted free fatty acids or fatty acid derivatives such as fatty alcohols can optionally be recovered from the culture medium by adding an organic solvent to the culture during at least a portion of the culturing period, or immediately after the culturing period. For example, a non-water miscible solvent that includes an alkane, alkene, or fatty alcohol, or any combination thereof, can be added to the culture at the end of the culture period, for example, during the final one, two, three, four, five or more days of culturing, or during the final one, one to four, four to eight, eight to twelve, twelve to sixteen, or sixteen to twenty-four hours of culturing. In some examples, incubation of the culture with the solvent does not substantially affect the productivity of the culture. In some examples, incubation of the culture with the solvent does not substantially affect the viability of the culture. In some examples, at least 50%, at least 60%, at least 70%, at least 80%, at least 90%, or greater than 90% of the microorganism cells survive treatment with the solvent.

An organic solvent that can be added during the culture period is not miscible with water, and has melting point less than about 25° C., and preferably has a melting point below about 30° C. Preferably the solvent is tolerated by the microorganism for a period of at least one hour, at least two hours, at least four hours, at least eight hours, at least twelve hours, at least sixteen hours, or for twenty-four hours or longer, such that the microorganism continues to produce a free fatty acid or a fatty acid derivative during the period the culture is incubated with the organic solvent. The solvent may comprise, for example an alkane, such as, for example, heptane, octane, nonane, decane, dodecane, or tetradecane. The solvent may additionally or alternatively comprise ean alkene. The solvent may further alternatively or in addition comprise a fatty alcohol, such as, for example, a C10 fatty alcohol, a C11 fatty alcohol, a C12 fatty alcohol, a C13 fatty alcohol, a C14 fatty alcohol, or a C16 fatty alcohol. For example, one or more fatty alcohols produced by a culture of a recombinant microorganism may be used to extract further fatty alcohols from the culture medium.

In some practices, a culture may be extracted multiple times with an organic solvent. The time period between removal of organic solvent added for a first solvent incubation period and the addition of organic solvent for the second incubation period can be brief, e.g., less than one hour, or can be for several hours or days. The culture may in some instances be allowed a period of growth and/or recovery when genes encoding polypeptides for producing free fatty acids or fatty acid derivatives and/or transporter components or secretion system components are not expressed, or the microorganism may continue to produce a free fatty acid or fatty acid derivative (such as a fatty alcohol) between extractions.

In some embodiments where fatty alcohols are produced, the methods of the invention can comprise a further step of converting the produced fatty alcohol(s) into one or more other fatty acid derivatives, e.g., alkanes, alkenes or wax esters. In certain embodiments, the methods further comprise the step of producing an alkene from the fatty alcohol product. In certain embodiments, the methods further comprise the step of esterifying at least part of the fatty alcohol product to a wax ester. The further step may be carried out in a recombinant host cell capable of, e.g., reducing or decarbonylating fatty alcohols to alkanes and/or alkenes or esterifying fatty alcohols to fatty esters. Additionally or alternatively, the further step may be carried out in a cell-free system (e.g., chemically). Any method known in the art may be used to convert the fatty alcohols to alkanes/alkenes or to esterify the fatty alcohol to a fatty ester. See, e.g., Smith, M B., *March's Advanced Organic Chemistry* (5$^{th}$ Ed.), Wiley: NY, 2001.

The invention also provides a fatty alcohol isolated according to the methods of the invention, an alkene produced by the methods of the invention and a wax ester produced by the methods of the invention. In certain embodiments, the fatty alcohols, alkenes, and/or wax esters described herein can be used as components of fuel compositions.

Methods of the invention as described herein may be carried out using a variety of nucleic acid molecules, vectors, polypeptides, host cells, and/or systems. The sections above and below provide additional details about these and other components that may be useful in practicing methods of the invention.

Nucleic Acid Molecules

The present invention provides nucleic acid molecules that encode alcohol-forming acyl-ACP reductases. The nucleic acid molecules described herein can be used in any of the methods of the invention, and may be included in any of the vectors or host cells of the invention. In some embodiments, a nucleic acid molecule of the invention is isolated and/or purified.

In some embodiments, the invention provides an isolated or recombinant nucleic acid molecule comprising a nucleic acid sequence that encodes an alcohol-forming acyl-ACP reductase that has at least about 40%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2, for example, at least about 90% or at least about 95% identity to the amino acid sequence of SEQ ID NO: 2, or to a functional fragment of the alcohol-forming acyl-ACP reductase of SEQ ID NO: 2. In some embodiments, the isolated or recombinant nucleic acid molecule can comprise a nucleotide sequence that encodes a polypeptide comprising the amino acid sequence of SEQ ID NO: 2. In some embodiments, the invention provides an isolated or recombinant nucleic acid molecule that comprises a nucleic acid sequence that encodes an alcohol-forming acyl-ACP reductase, where the nucleic acid sequence has at least about 30%, 40%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, for example, at least about 85% or at least about 90% identity to the nucleotide sequence of SEQ ID NO: 1, or to a fragment of the nucleotide sequence of SEQ ID NO: 1 that encodes a functional fragment of the alcohol-forming acyl-ACP reductase of SEQ ID NO: 2. In some embodiments, the invention provides an isolated or recombinant nucleic acid molecule that comprises a nucleic acid sequence that encodes an alcohol-forming acyl-ACP reductase wherein the isolated or recombinant nucleic acid molecule comprises the nucleotide sequence of SEQ ID NO: 1. Additionally to any of the above embodiments, in some embodiments, the isolated or recombinant nucleic acid molecule can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic microorganism.

In some embodiments, the invention provides an isolated or recombinant nucleic acid molecule comprising a nucleic acid sequence that encodes an alcohol-forming acyl-ACP reductase that has at least about 40%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 4, for example, at least about 90% or at least about 95% identity to the amino acid sequence of SEQ ID NO: 4, or to a functional fragment of the alcohol-forming acyl-ACP reductase of SEQ ID NO: 4. In some embodiments, the isolated or recombinant nucleic acid molecule can comprise a nucleotide sequence that encodes a polypeptide comprising the amino acid sequence of SEQ ID NO: 4. In some embodiments, the invention provides an isolated or recombinant nucleic acid molecule that comprises a nucleic acid sequence that encodes an alcohol-forming acyl-ACP reductase, where the nucleic acid sequence that has at least about 30%, 40%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 3, for example, at least about 85% or at least about 90% identity to the nucleotide sequence of SEQ ID NO: 3, or to a fragment of the nucleotide sequence of SEQ ID NO: 3 that encodes a functional fragment of the alcohol-forming acyl-ACP reductase of SEQ ID NO: 4. In some embodiments, the invention provides an isolated or recombinant nucleic acid molecule that comprises a nucleic acid sequence that encodes an alcohol-forming acyl-ACP reductase wherein the isolated or recombinant nucleic acid molecules comprises the nucleotide sequence of SEQ ID NO: 3. Additionally to any of the above embodiments, in some embodiments, the isolated or recombinant nucleic acid molecule can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic microorganism.

In some embodiments, the invention provides an isolated or recombinant nucleic acid molecule comprising a nucleic acid sequence that encodes an alcohol-forming acyl-ACP reductase that has at least about 40%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 6, 8, or 10, for example, at least about 90% or at least about 95% identity to the amino acid sequence of SEQ ID NO: 6, 8, or 10, or to a functional fragment of the alcohol-forming acyl-ACP reductase of SEQ ID NO: 6, 8, or 10. In some embodiments, the isolated or recombinant nucleic acid molecule can comprise a nucleotide sequence that encodes a polypeptide comprising the amino acid sequence of SEQ ID NO: 6, 8, or 10. In some embodiments, the invention provides an isolated or recombinant nucleic acid molecule that comprises an nucleic acid sequence that encodes an alcohol-forming acyl-ACP reductase, where the nucleic acid sequence has at least about 30%, 40%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 5, 7, or 9, for example, at least about 85% or at least about 90% identity to the nucleotide sequence of SEQ ID NO: 5, 7, or 9, or to a fragment of the nucleotide sequence of SEQ ID NO: 5, 7, or 9 that encodes a functional fragment of the polypeptide of SEQ ID NO: 6, 8, or 10 having alcohol-forming acyl-ACP reductase activity. In some embodiments, the invention provides an isolated or recombinant nucleic acid molecule that comprises a nucleic acid sequence that encodes an alcohol-forming acyl-ACP reductase wherein the isolated or recombinant nucleic acid molecules comprises the nucleotide sequence of SEQ ID NO: 5, 7, or 9. Additionally to any of the above embodiments, in some embodiments, the isolated or recombinant nucleic acid molecule can further comprise an additional nucleic acid sequence of at least about 50, 60, 70, 80, 90, 100, 150, 200, 250, 300, 350, 400, 450, 500, 550, 600, 700, 800, 900, 1000, or 1500 nucleotides from a photosynthetic microorganism.

For optimal expression of a recombinant protein, in certain instances it may be beneficial to employ coding sequences that produce mRNA with codons preferentially used by the host cell to be transformed ("codon optimization"). Thus, for enhanced expression of transgenes, the codon usage of the transgene can be matched with the specific codon bias of the organism in which the transgene is desired to be expressed. Methods of recoding genes for expression in microalgae are described in, e.g., U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some embodiments, only a portion of the codons of a particular open reading frame is changed to reflect a preferred codon usage of a host microorganism. In certain embodiments, one or more codons are changed to codons that are not necessarily the most preferred codon of the host microorganism encoding a particular amino acid. Additional information for codon optimization is available, e.g. at the codon usage database of GenBank. The coding sequences may be codon optimized for optimal production of a desired product in the host organism selected for expression. In certain embodiments, the nucleic acid sequence encoding an alcohol-forming acyl-ACP reductase is codon optimized for expression in a photosynthetic microorganism, e.g., a cyanobacterium or a eukaryotic microalga.

In some embodiments, expression in a photosynthetic microorganism of an isolated or recombinant nucleic acid molecule encoding a polypeptide comprising an amino acid sequence having at least about 40%, 50%, 60%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2, 4, 6, 8, or 10, or to a functional fragment of the polypeptide, results in higher production level, e.g., at least 50% higher, of a fatty alcohol by the photosynthetic microorganism than the production level in a control photosynthetic microorganism cultured under the same conditions and substantially identical to the photosynthetic microorganism expressing the isolated or recombinant nucleic acid molecule in all respects, with the exception that the control microorganism does not express the isolated or recombinant nucleic acid molecule.

In some embodiments, the invention encompasses deletion mutants of an alcohol-forming acyl-ACP reductase where a nucleic acid molecule encodes a reductase protein in which one or more amino acids have been deleted from the protein.

In one embodiment, the polypeptide is 512, 511, 510, 509, 508, 507, 506, 505, 504 or 503 residues or less and has an amino acid sequence at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% identical to the corresponding amino acid sequence of SEQ ID NO: 2. In another embodiment, the polypeptide is 504, 503, 502, 501, 500, 499, 498, 497, 496 or 495 residues or less and has an amino acid sequence at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% identical to the corresponding amino acid sequence of SEQ ID NO: 4. In another embodiment, the polypeptide is 511, 510, 509, 508, 507, 506, 505, 504, 503 or 502 residues or less and has an amino acid sequence at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% identical to the corresponding amino acid sequence of SEQ ID NO: 6. In another embodiment, the polypeptide is 511, 510, 509, 508, 507, 506, 505, 504, 503 or 502 residues or less and has an amino acid sequence at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% identical to the corresponding amino acid sequence of SEQ ID NO: 8. In another embodiment, the polypeptide is 513, 512, 511, 510, 509, 508, 507, 506, 505 or 504 residues or less and has an amino acid sequence at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% identical to the corresponding amino acid sequence of SEQ ID NO: 10. In other embodiments, the polypeptide lacks at least 1, 2, 3, 4, 5, 6, 7, 8, 9 or 10 amino acids from the N- and/or C-terminus and has an amino acid sequence at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% identical to the corresponding amino acid sequence of SEQ ID NO: 2, 4, 6, 8 or 10.

The invention also provides an isolated or recombinant nucleic acid molecule comprising a nucleic acid sequence encoding an amino acid sequence having at least about 40%, 50%, 60%, 70%, 75%, 80%, 85%, 86%, 87%, 88%, 89%, 90%, 91%, 92%, 93%, 94%, 95%, 96%, 97%, 98%, 99% or 100% sequence identity with a fragment comprising a consecutive sequence of at least about 20, 50, 75, 100, 125, 150, 175, 200, 225, 250, 275, 300, 325, 350, 375, 400, 425, 450, 475 or 500 amino acid residues from SEQ ID NO: 2, 4, 6, 8 or 10. Such fragments and fragment variants may be useful as probes and primers. In certain embodiments, such probes and primers may selectively hybridize to the nucleic acid molecule encoding the polypeptides described herein. In certain embodiments, the fragments encode polypeptides that retain at least about 10, 20, 30, 40, 50, 60, 70, 80, 90 or 100% of the alcohol-forming acyl-ACP reductase activity of the full-length protein when expressed in a recombinant host cell. In particular embodiments, the fragments are functional fragments.

Further, the invention provides variants of the amino acid sequence of SEQ ID NO: 2, 4, 6, 8, or 10 or fragments thereof. Variants may be naturally occurring, and/or non-naturally-occurring, such as those induced by various mutagens and mutagenic processes. In some embodiments, at least one amino acid residue has been inserted N- and/or C-terminal to, and/or within, the reference sequence. In some embodiments, at least one amino acid residue has been deleted N- and/or C-terminal to, and/or within, the reference sequence. In some embodiments, variants may be sequences containing predetermined mutations by, e.g. homologous recombination or site-directed or PCR mutagenesis; corresponding proteins of other species; alleles or other naturally occurring variants; and/or derivatives wherein the protein has been covalently modified by chemical, enzymatic or other appropriate means with a moiety other than a naturally occurring amino acid.

A substitution, insertion or deletion may adversely affect the protein when the altered sequence substantially inhibits a biological function associated with the protein. In certain embodiments, a variant of an alcohol-forming acyl-ACP reductase may have activity that is reduced by not more than about 1%, 2%, 3%, 4%, 5%, 6%, 7%, 8%, 9%, 10%, 15%, 20%, 30%, 40%, 50%, 60%, 70%, 80% or 90% in comparison to the activity of the reductase from which the variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)). In some embodiments, the amount of fatty alcohol produced by a host cell expressing the alcohol-forming acyl-ACP reductase variant is not less than about 99%, 98%, 97%, 96%, 95%, 94%, 93%, 92%, 91%, 90%, 85%, 80% or 75% of the amount of fatty alcohol produced by a host cell expressing the reductase from which the variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)).

The invention also provides fragments and variants of an alcohol-forming acyl-ACP reductase that have increased activity in comparison to the reference polypeptide. In certain embodiments, the fragment or variant may have activity that is increased by at least about 5%, 10%, 20%, 30%, 40%, 50%, 60%, 70%, 80%, 90%, 100%, 200%, 300%, 400%, 500%, 600%, 700%, 800%, 900% or 1000% in comparison to the activity of the alcohol-forming acyl-ACP reductase from which the variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)). In certain embodiments, the amount of fatty alcohols produced by a host cell expressing the fragment or variant is at least about 5%, 10%, 20%, 30%, 40%, 50%, 60%, 70%, 80%, 90%, 100%, 200%, 300%, 400%, 500%, 600%, 700%, 800%, 900% or 1000% of the amount of fatty alcohol produced by a host cell expressing the alcohol-forming reductase from which the fragment or variant is derived (e.g., Maqu_2220 (SEQ ID NO: 2), Hch_05075 (SEQ ID NO: 4), MDG893_11561 (SEQ ID NO: 6), HP15_810 (SEQ ID NO: 8), or RED65_09894 (SEQ ID NO: 10)).

Nucleic acid molecules encoding components of prokaryotic transporters, e.g., prokaryotic efflux pumps and prokaryotic protein secretion systems are also provided, such as but not limited to nucleic acid molecules that encode a component of a secondary multidrug resistance transporter, such as, for example, a component of a Major Facilitator Superfamily (MFS) transporter, a component of a Small Multidrug Resistance (SMR) transporter, a component of a Resistance-cell Division (RND) transporter, a component of a Multi Antimicrobial Extrusion (MATE) transporter, and a component of a Putative E Transporter (PET) transporter. For example, a nucleic acid molecule that encodes a component of a Small Multidrug Resistance (SMR) transporter can encode a component of a Small Multidrug Resistance (SMR) transporter, a component of a Resistance-cell Division (RND) transporter, such as, but not limited to, an inner membrane permease, a membrane fusion protein, or an outer membrane factor. A large number of such secondary efflux transporters are known. A nucleic acid molecule as provided herein encodes a polypeptide having at least 80%, at least 85%, at least 90%, at least 95%, at least 96%, at least 97%, at least 98%, at least 99% or 100% identity to the amino acid sequence of a known component of an SMR or RND transporter, and can encode a polypeptide that can have, for example, at least 80%, at least 85%, at least 90%, at least 95%, at least 96%, at least 97%, at least 98%, at least 99% or 100% to a component of an RND transporter, such as but not limited to a Mex or Acr transporter. For example, A nucleic acid molecule as provided herein encodes a polypeptide having at least 80%, at least 85%, at least 90%, at least 95%, at least 96%, at least 97%, at least 98%, at least 99% or 100% identity to SEQ ID NO:19, SEQ ID NO:20; SEQ ID NO:21 SEQ ID NO:27, SEQ ID NO:29; or SEQ ID NO:35 (a TolC-type outer membrane factor component of an RND transporter of *Synechocystis*). Any of these nucleic acids can be used in any of the microorganisms or methods provided herein.

Nucleic acid molecules that encode a component of a prokaryotic protein secretion system, such as a Type VI secretion system, are also provided herein. For example, provided herein are nucleic acid molecules that encode polypeptides having at least 80%, at least 85%, at least 90%, at least 95%, at least 96%, at least 97%, at least 98%, at least 99% or 100% identity to the amino acid sequence of a known Vsgr polypeptide of a prokaryotic Type VI secretion system. For example, provided herein are nucleic acid molecules that encode polypeptides having at least 80%, at least 85%, at least 90%, at least 95%, at least 96%, at least 97%, at least 98%, at least 99% or 100% identity to SEQ ID NO:37, SEQ ID NO:39, or SEQ ID NO:40. Any of the foregoing nucleic acids can be used in any of the microorganisms or methods provided herein.

The invention also provides variants of the nucleotide sequences of the invention. In some embodiments, the nucleotide sequence variants encode fragments or variants of the polypeptides as described herein. In some embodiments, the nucleotide sequence variants are naturally-occurring. In other embodiments, the nucleotide sequence variants are non-naturally-occurring, such as those induced by various mutagens and mutagenic processes. In certain embodiments, the nucleotide sequence variants are a combination of naturally- and non-naturally-occurring. A given nucleic acid sequence may be modified, for example, according to standard mutagenesis or artificial evolution or domain swapping methods to produce modified sequences. Accelerated evolution methods are described, e.g. by Stemmer (1994) *Nature* 370, 389-391, and Stemmer (1994) *Proc. Natl. Acad. Sci. USA* 91, 10747-10751. Chemical or enzymatic alteration of expressed nucleic acids and polypeptides can be performed by standard methods. For example, a sequence can be modified by addition of phosphate groups, methyl groups, lipids, sugars, peptides or organic or inorganic compounds, by the inclusion of modified nucleotides or amino acids, or the like.

In some embodiments, the nucleic acid molecules of the invention encode fusion proteins that comprise an alcohol-forming acyl-ACP reductase. For example, the nucleic acids of the invention may comprise polynucleotide sequences that encode glutathione-S-transferase (GST) or a portion thereof, thioredoxin or a portion thereof, maltose binding protein or a portion thereof, poly-histidine (e.g. $His_6$), poly-HN, poly-lysine, a hemagglutinin tag sequence, HSV-Tag and/or at least a portion of HIV-Tat fused to the alcohol-forming acyl-ACP reductase sequence.

In some embodiments, the nucleic acid molecules of the invention comprise additional non-coding sequences such as non-coding 3' and 5' sequences (including, e.g., regulatory sequences).

The invention also provides nucleic acid molecules that hybridize under high stringency hybridization conditions, such as selective hybridization conditions, to the nucleotide sequences described herein. Hybridization probes include synthetic oligonucleotides which bind in a base-specific manner to a complementary strand of nucleic acid. Suitable probes include polypeptide nucleic acids, as described in Nielsen (1991) *Science*, 254, 1497-1500. In some embodiments, nucleic acid molecules of the invention can be detected and/or isolated by specific hybridization, e.g., under high stringency conditions.

Vectors

The invention also provides a vector (e.g., an expression vector) comprising an isolated nucleic acid molecule encoding an alcohol-forming acyl-ACP reductase. In some embodiments, the vector comprises one or more sequences that promote expression of the alcohol-forming acyl-ACP reductase. For example, the nucleic acid sequence encoding the alcohol-forming acyl-ACP reductase may be operably linked to a promoter, e.g., in an "expression cassette." In some embodiments, the promoter is regulatable, e.g., inducible.

In other embodiments where the vector does not contain a promoter in operable linkage with the nucleic acid sequence encoding the alcohol-forming acyl-ACP reductase, the nucleic acid sequence can be transformed into the cells such that it becomes operably linked to an endogenous promoter by, e.g., homologous recombination, site specific integration and/or vector integration. In some embodiments, the endogenous promoter is regulatable, e.g., inducible.

A promoter operably linked to a nucleic acid sequence encoding an alcohol-forming acyl-ACP reductase of the invention may be a heterologous promoter. In some embodiments, the promoter may be a regulatable promoter, e.g., an inducible promoter, i.e., a promoter that mediates transcription of an operably linked gene in response to a particular stimulus. Such promoters may be advantageous, e.g., to minimize any deleterious effects on the growth of the host cell and/or to maximize production of the fatty alcohol. An inducible promoter can be responsive to, e.g., light or dark or high or low temperature, and/or can be responsive to specific compounds. The inducible promoter may be, for example, an ara promoter, a lac promoter, a tet promoter (e.g. U.S. Pat. No. 5,851,796), a trp promoter, or a hybrid promoter that includes one or more portions of a tet, trp, or lac promoter. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

In some embodiments, a nucleic acid sequence encoding an alcohol-forming acyl-ACP reductase is operably linked to a promoter that functions in prokaryotes, such as cyanobacteria, including, but not limited to, the lac, tac and trc promoters, as well as derivatives such as but not limited to the trcE and trcY promoters that are inducible by the addition of isopropyl β-D-1-thiogalactopyranoside (IPTG), promoters that are naturally associated with transposon- or bacterial chromosome-borne antibiotic resistance genes (e.g. neomycin phosphotransferase, chloramphenicol acetyltransferase, spectinomycin adenyltransferase, etc., or combinations thereof), promoters associated with various heterologous bacterial and native cyanobacterial genes, promoters from viruses and phages, synthetic promoters or combinations thereof. In certain embodiments, the promoters are isolated from cyanobacteria, e.g., secA (secretion; controlled by the redox state of the cell), rbc (Rubisco operon), psaAB (PS I reaction center proteins; light regulated), NtcA or glnA promoter and psbA (DI protein of PSII; light-inducible). In some embodiments, the promoters are regulated by nitrogen compounds, such as, for example, nar, ntc, nir or nrt promoters. In some embodiments, the promoters are regulated by phosphate (e.g., pho or pst promoters) or nickel (e.g., nrs promoter). Promoters for use in cyanobacteria can also be modified from naturally-occurring promoters, and include combinations of naturally-occurring promoters, including, but not limited to, the promoters disclosed herein. In some embodiments, the promoter(s) are selected from prokaryotic promoters from a range of species, including eubacterial and cyanobacterial species, such as, for example, an araC or pBAD promoter, a rha promoter, a Pm promoter, a xylS promoter, a nir promoter, a nar promoter, a pho promoter, a tet promoter, a cys promoter, a metallothionien promoter, an ftf promoter, a gln promoter, a heat shock promoter, a cold-inducible promoter or a viral promoter. The foregoing promoters are exemplary and are not limiting.

A wide variety of transcriptional terminators can be used in vector construction. Examples of possible terminators can include, but are not limited to, psbA, psaAB, rbc, secA, T7 coat protein, rrnB, and the like, and combinations thereof.

In certain embodiments, the vector comprising the nucleic acid sequence encoding an alcohol-forming acyl-ACP reductase is designed for transformation into cyanobacteria. In a particular embodiment, the vector permits homologous recombination of the alcohol-forming acyl-ACP reductase sequence with the cyanobacterial genome.

In some embodiments, the vector is an integration vector that includes one or more sequences that promote integration of a gene of interest or gene expression cassette into the genome of the host cell. For example, an integration vector used to transform a host cell can include at least one sequence of at least about 50, at least 100, at least 200, at least 300, at least 400, at least 500, at least 600, at least 700, at least 800, at least 900, at least 1000, at least 1200, or at least 1500 nucleotides with homology to a sequence in the genome of the host cell to allow integration of the gene or gene expression cassette into the genome of the host cell via homologous recombination. In some examples, the gene or gene expression cassette is flanked by sequences homologous to a region of the host chromosome to promote integration of the gene of interest into the host chromosome. Additionally or alternatively, an integration vector can include one or more sequences that promote site-specific recombination or random integration such as, but not limited to, sequences recognized by recombinases, integrases or transposases. In some embodiments, the integration vector can further include a gene encoding a recombinase, integrase or transposase. In certain embodiments, the integration vector is designed to promote integration of an alcohol-forming acyl-ACP reductase gene into cyanobacteria. In particular embodiments, the vector promotes integration at the RS1 site or the RS2 site in cyanobacteria (e.g., in *Synechocystis* sp. PCC 6803).

Transformation vectors can additionally or alternatively include a selectable marker, such as but not limited to a drug resistance gene, an herbicide resistance gene, a metabolic enzyme and/or factor required for survival of the host (for example, an auxotrophic marker), or the like, or a combination thereof. Transformed cells can optionally be selected based upon the ability to grow in the presence of the antibiotic and/or other selectable marker under conditions in which cells lacking the resistance cassette or auxotrophic marker could not grow. Additionally or alternatively, a non-selectable marker may be present on a vector, such as a gene encoding a fluorescent protein or an enzyme that generates a detectable reaction product.

Vectors can be introduced into host cells (e.g., any of the host cells described herein) via conventional transformation and/or transfection techniques. Cyanobacteria, for example, can be transformed by any suitable methods, including, e.g., natural DNA uptake (Zang (2007) *J. Microbiol.* 45, 241-245), conjugation, transduction, glass bead transformation (Feng (2009) *Mol. Biol. Rep.* 36, 1433-9), silicon carbide whisker transformation (Dunahay (1997) *Methods Mol. Biol.* 62, 503-9), biolistics (Kroth (2007) *Methods Mol. Biol.* 390, 257-267), electroporation (Ludwig (2008) *Appl. Microbiol. Biotechnol.* 78, 729-35), laser-mediated transformation (WO2009/140701), incubation with DNA in the presence of or after pre-treatment with any of poly(amidoamine) dendrimers (Pasupathy (2008) *Biotechnol. J.* 3, 1078-82), polyethylene glycol (Ohnuma (2008) *Plant Cell Physiol.* 49, 117-120), cationic lipids (Muradawa (2008) *J. Biosci. Bioeng.* 105, 77-80), dextran, calcium phosphate and/or calcium chloride (Mendez-Alvarez (1994) *J. Bacteriol.* 176, 7395-7397), optionally after treatment of the cells with cell wall-degrading enzymes (Perrone (1998) *Mol. Biol. Cell* 9, 3351-3365), or the like, or combinations thereof. *Agrobacterium*-mediated transformation can additionally or alternatively be performed on algal cells, for example after removing or wounding the algal cell wall (Kumar (2004) *Plant Sci.* 166, 731-738).

The above-described vectors may be used in any of the methods for producing a fatty alcohol as described herein.

Recombinant Host Cells

The invention also provides a recombinant host cell comprising a non-native and/or recombinant nucleic acid molecule that encodes an alcohol-forming acyl-ACP reductase. The recombinant host cell may comprise, e.g., any of the isolated or recombinant nucleic acid molecules or vectors described herein. In some embodiments, the nucleic acid sequence encoding the alcohol-forming acyl-ACP reductase is non-native to the recombinant host cell.

In some embodiments, the recombinant host cell is a yeast cell (e.g., *Y. lipolytica* or *S. cerevisiae*), a fungal cell, a filamentous fungal cell, an algal cell or a bacterial cell (e.g., *E. coli*). Oleaginous yeasts, including but not limited to *Aspergillus niger, Yarrowia lypolytica, Cryptococcus curvatus, Cryptococcus terricolus, Candida* species, *Lipomyces starkeyi, Lipomyces lipofer, Endomycopsis vernalis, Rhodotorula glutinis,* and *Rhodotorula gracilis* can also be microorganisms and host cells for use in the invention. Other fungi, including but not limited to species of *Aspergillus, Trichoderma, Neurospora, Fusarium, Humicola, Rhizomucor, Kluyveromyces, Pichia, Mucor, Myceliophtora, Penicillium, Phanerochaete, Chrysosporium, Saccharomyces,* and *Schizosaccharomyces,* are also encompassed as microorganisms and host cells for use with the invention. Heterokonts including but not limited to *Labyrinthulomycete* species (e.g., *Thraustichytrium, Ulkenia,* and *Schizochytrium* species) can also be microorganisms and host cells for use in the invention.

Alternatively, the recombinant microorganism or host cell is a bacterium, such as, but not limited to, an *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Shewanella, Stenotrophomonas, Streptomyces, Streptococcus, Vibrio,* or *Zymomonas* species.

In some embodiments, the recombinant host cell is any prokaryotic microorganism, including without limitation, a eubacterium, archaebacterium, green nonsulfur bacterium, purple nonsulfur bacterium or cyanobacterium. In some embodiments, the recombinant host cell is a photosynthetic microorganism.

In certain embodiments, the photosynthetic microorganism is a cyanobacterium. A number of cyanobacterial species are known and have been manipulated using molecular biological techniques, including the unicellular cyanobacteria *Synechocystis* sp. PCC6803 and *Synechococcus* elongates PCC7942, whose genomes have been completely sequenced. In some embodiments, the cyanobacterium is selected from, e.g., *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus* species. For example, the recombinant photosynthetic microorganism can be a *Synechococcus, Synechocystis,* or *Thermosynechococcus* species. Alternatively, the recombinant photosynthetic microorganism can be a *Cyanobium, Cyanothece,* or *Cyanobacterium* species, or further alternatively, the recombinant photosynthetic microorganism can be a *Gloeobacter, Lyngbya* or *Leptolyngba* species.

In some embodiments, the cyanobacterial strain is *Synechocystis* sp. PCC 6803. In some embodiments, the non-native/recombinant nucleic acid sequence that encodes the alcohol-forming acyl-ACP reductase is integrated into the host genome at the RS1 or RS2 site. In certain embodiments, the photosynthetic microorganism is a eukaryotic microalga, and in some embodiments is of a genus selected from, e.g., *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox* species.

In some embodiments, the recombinant host cell is a photosynthetic microorganism that includes an exogenous nucleic acid molecule encoding an alcohol-forming acyl-ACP reductase with at least about 40%, 50%, 60%, 70%, 75%, 80%, 85%, 86%, 87%, 88%, 89%, 90%, 91%, 92%, 93%, 94%, 95%, 96%, 97%, 98%, or 99% sequence identity to a polypeptide comprising the amino acid sequence of SEQ ID NO: 2, 4, 6, 8, or 10, or to a functional fragment of the polypeptide. In certain embodiments, the recombinant host cell expresses an alcohol-forming acyl-ACP reductase that comprises or consists essentially of the polypeptide of SEQ ID NO: 2, 4, 6, 8, or 10. In certain embodiments, the nucleic acid sequence is derived from a marine bacterium, e.g., a *Marinobacter* or *Hahella* species. In some embodiments, the recombinant host cell is a photosynthetic microorganism that comprises a nucleic acid sequence encoding an alcohol-forming acyl-ACP reductase with at least about 30%, 40%, 50%, 60%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, 3, 5, 7, or 9, or to a fragment of the nucleotide sequence that encodes a functional fragment of the alcohol-forming acyl-ACP reductase. In certain embodiments, the nucleic acid sequence encoding the alcohol-forming acyl-ACP reductase comprises the nucleotide sequence of SEQ ID NO: 1, 3, 5, 7, or 9. In some embodiments, the recombinant host cell comprises a vector comprising the nucleic acid sequence encoding the alcohol-forming acyl-ACP reductase operably linked to a promoter. In certain embodiments, the promoter is regulatable. In particular embodiments, the promoter is inducible. In some embodiments, the recombinant host cell is a photosynthetic host cell, e.g., a photosynthetic microorganism.

In some embodiments, the recombinant host cell is not engineered to produce or overproduce acyl-CoA. For example, in some embodiments, the host microorganism does not include an exogenous nucleic acid molecule encoding an acyl-CoA synthetase. In some embodiments, the recombinant host cell is engineered to eliminate endogenous expression of acyl-CoA synthetase. For example, if the recombinant host cell is *E. coli*, the host cell may be engineered to eliminate expression of the fadD and/or fadK acyl-CoA synthetase genes. In some embodiments, the recombinant host cell does not endogenously produce acyl-CoA, and is not genetically engineered to produce acyl-CoA. In other embodiments, the recombinant host cell endogenously produces acyl-CoA but is engineered to eliminate acyl-CoA production. In still other embodiments, the recombinant host cell endogenously produces acyl-CoA and generates a fatty alcohol via both acyl-CoA-dependent and acyl-CoA-independent pathways.

In certain embodiments, the recombinant host cell does not express, e.g., an acyl-ACP thioesterase, an acyl-CoA thioesterase, or an acyl-CoA synthetase. In certain embodiments, the recombinant host cell does not include an endogenous gene encoding e.g., an acyl-ACP thioesterase, an acyl-CoA thioesterase, or an acyl-CoA synthetase. For example, the host cell may be a cyanobacterial species that does not include an endogenous gene encoding an acyl-ACP thioesterase, an acyl-CoA thioesterase or an acyl-CoA synthetase. Additionally or alternatively, the recombinant host cell may be a cell that does not express an aldehyde-forming reductase (e.g., acyl-CoA reductase, aldehyde-forming acyl-ACP reductase or carboxylic acid reductase). In particular embodiments, the recombinant host cell does not express a non-native, e.g., heterologous, aldehyde-forming reductase.

In some embodiments, the recombinant host cell comprises one or more exogenous nucleic acid sequences encoding more than one alcohol-forming acyl-ACP reductase.

In certain embodiments, the recombinant host cell expressing an alcohol-forming acyl-ACP reductase expresses at least one additional recombinant or exogenous gene, or overexpresses an additional endogenous gene, that functions in the fatty alcohol biosynthesis pathway. The alcohol-forming acyl-ACP reductase and the additional gene may be encoded by separate nucleic acid molecules or by the same nucleic acid molecule. Where the two genes are encoded by the same nucleic acid molecule (e.g., on the same expression vector), the expression of each gene may optionally be independently regulated by a same or a different promoter and/or enhancer. In certain embodiments, the additional gene may increase the rate and/or level of fatty alcohol production. Additionally and/or alternatively, the additional gene may, e.g., increase the concentration of fatty alcohol precursors such as acyl-ACP, decrease the amount of acyl-ACP or fatty alcohol conversion to other products (such as, for example, other fatty acid derivatives or fatty alcohol breakdown products) or lower fatty alcohol toxicity to the cell. In certain embodiments, the polypeptide encoded by the additional gene is selected from, e.g., one or more enzymes of the fatty acid synthase complex (e.g., a beta-ketoacyl-ACP synthase, a 3-ketoacyl-ACP reductase, a β-hydroxyacyl-ACP dehydratase, an enoyl-ACP reductase, etc.), an acetyl-CoA carboxylase, a malonyl-CoA:ACP transacylase, an acyl carrier protein or an acyl-ACP synthetase. Additionally or alternatively, the recombinant host cell expressing an alcohol-forming acyl-ACP reductase can express a ribulose 1,5-bisphosphate carboxylase or a phycobiliprotein (e.g., phycocyanin).

The above-described recombinant host cells may be used in any of the methods of producing a fatty alcohol as described herein.

Systems

The invention also provides an acyl-CoA-independent system for producing a fatty alcohol from an inorganic carbon source, wherein the system includes a recombinant photosynthetic host cell (e.g., a recombinant photosynthetic microorganism) that includes a nucleic acid sequence encoding an alcohol-forming acyl-ACP reductase and is cultured in a medium that does not include a reduced carbon source. In some embodiments, the recombinant host cell does not produce acyl-CoA. The recombinant host cell may be, e.g., any of the recombinant host cells described herein, and may comprise any of the nucleic acid molecules and/or vectors described herein. The recombinant photosynthetic microorganism is exposed to light for at least a portion of the production period.

When cultured phototrophically, the host cell can advantageously use light as an energy source. An "inorganic" or non-reduced carbon source can be used for synthesis of biomolecules by the host cell. Typically an inorganic carbon source can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by host cells. In some embodiments, inorganic carbon is substantially the only carbon source present in the culture medium. In these embodiments, if an organic (reduced) carbon source or compound is present in the culture medium of a host cell grown phototrophically, it generally cannot be taken up and/or metabolized by the cell for energy or as a carbon source for the synthesis of biomolecules, and/or is not present in an amount sufficient to provide sustainable energy for the growth of the cell culture or production of organic molecules.

Microorganisms that can be useful in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of lipid and/or hydrocarbon constituents can vary. In some cases, certain strains of microorganisms may be unable to grow in a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of host cell types. For example, various fresh water and salt water media are well known in the art, e.g., those described in Barsanti (2005) Algae: Anatomy, Biochemistry & Biotechnology, CRC Press for media and methods for culturing algae.

The culture methods can include inducing expression of a particular gene described herein for the production of fatty alcohols (e.g., an alcohol-forming acyl-ACP reductase gene), and/or for regulating metabolic pathways in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the promoter operably linked to the gene of interest.

In some embodiments of the present invention, the recombinant host cells can be cultured in a bioreactor. Bioreactors can offer many advantages for use in heterotrophic growth and propagation methods. To produce biomass for use in food, microorganisms are preferably fermented in large quantities in liquid, such as, e.g., in suspension cultures. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen and/or nitrogen, to be contacted with (e.g. bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Cells can additionally or alternatively be cultured in a bioreactor equipped with a natural or artificial light source (a "photobioreactor"), and/or can have one or more walls that is transparent enough to light, including sunlight, to enable, facilitate and/or maintain acceptable microorganism growth. For production of fatty alcohols, photosynthetic microorganisms can additionally or alternatively be cultured in shake flasks, test tubes, vials, microtiter dishes, petri dishes, or the like, or combinations thereof.

Genetically engineered photosynthetic microorganisms may also be grown in, e.g., ponds, canals, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, etc., or combinations thereof, can be supplied to the culture. When supplying flue gas and/or other sources of inorganic carbon that may contain CO in addition to $CO_2$, it may be necessary to pre-treat such sources such that the CO level introduced into the (photo)bioreactor does not constitute a dangerous and/or lethal dose vis-à-vis the growth and/or survival of the microorganisms.

In some embodiments, the fatty alcohol produced by a system of the invention is secreted into the culture medium by the recombinant host cell. Additionally or alternatively, the fatty alcohol may be extracted from the recombinant host cell. In some embodiments, the fatty alcohol is isolated using a method described herein.

In some embodiments, the systems of the invention result in production of at least 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/L of fatty alcohol/culture over a culture period of 1, 2, 3, 4, 5, 6, 7, 8, 9, 10, 11, 12, 13, or 14 days by culturing the recombinant microorganisms described herein. In some embodiments, the fatty alcohols are further processed in the system to other fatty acid derivatives, such as fatty aldehydes, wax esters, alkenes and/or alkanes.

Systems of the invention as described herein may use a variety of nucleic acid molecules, vectors, polypeptides and/or host cells. In some embodiments, the systems use one or more nucleic acid molecules, vectors, polypeptides and/or host cells described herein. Further, the systems may be used to perform any of the methods for producing a fatty alcohol as described herein.

Additionally or alternatively, the present invention can include one or more of the following embodiments:

Embodiment 1

A method of producing one or more fatty alcohols, comprising the steps of: culturing a recombinant microorganism in a suitable culture medium, wherein the recombinant microorganism does not produce acyl-CoA and does not express an exogenous acyl-ACP thioesterase, wherein the recombinant microorganism comprises a non-native nucleic acid sequence which produces an alcohol-forming acyl-ACP reductase upon expression in the recombinant microorganism; and allowing expression of said non-native nucleic acid sequence, wherein said expression results in the production of at least 0.5 mg/L fatty alcohols/culture in a seven day culture period.

Embodiment 2

The method of embodiment 1, wherein the recombinant microorganism is a photosynthetic microorganism, optionally wherein the photosynthetic microorganism is cultured either mixotrophically or phototrophically, wherein the culture is exposed to light for at least a portion of the culture period.

Embodiment 3

The method of embodiment 2, wherein the photosynthetic microorganism is cultured phototrophically, wherein inorganic carbon is substantially the sole source of carbon in the medium, optionally wherein the inorganic carbon source is $CO_2$, carbonic acid, a carbonate, or a bicarbonate.

Embodiment 4

A recombinant photosynthetic microorganism that comprises a non-native nucleic acid molecule encoding an alcohol-forming acyl-ACP reductase, wherein the recombinant microorganism produces at least 0.5 mg/L fatty alcohols/culture in a seven day culture period, wherein the recombinant photosynthetic microorganism does not produce an acyl-CoA synthetase and one or both of an acyl-ACP thioesterase and an acyl-CoA thioesterase.

Embodiment 5

The method or microorganism of any of the previous embodiments wherein any of the following are satisfied: a)

the alcohol-forming acyl-ACP reductase is a microbial alcohol-forming acyl-ACP reductase, b) the alcohol-forming acyl-ACP reductase is a prokaryotic alcohol-forming acyl-ACP reductase, c) the alcohol-forming acyl-ACP reductase is an alcohol-forming acyl-ACP reductase of a marine microorganism, d) the alcohol-forming acyl-ACP reductase is an alcohol-forming acyl-ACP reductase of a marine bacterium, e) the alcohol-forming acyl-ACP reductase is an alcohol-forming acyl-ACP reductase of the order *Oceanospirillilales*, f) the alcohol-forming acyl-ACP reductase is an alcohol-forming acyl-ACP reductase of a gammaproteobacterium, g) the alcohol-forming acyl-ACP reductase is an alcohol-forming acyl-ACP reductase of a *Marinobacter, Alcanivorax, Ocenaobacter*, or *Hahella* species, h) the alcohol-forming acyl-ACP reductase is an alcohol-forming acyl-ACP reductase having at least at least 40%, at least 50%, at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% to SEQ ID NO: 2. SEQ ID NO: 4, SEQ ID NO: 6, SEQ ID NO: 8, or SEQ ID NO: 10; and i) the alcohol-forming acyl-ACP reductase is a promiscuous alcohol-forming fatty acyl reductase.

Embodiment 6

The method or microorganism of any of embodiments 1-5, wherein the recombinant microorganism does not produce an acyl-CoA synthetase, further wherein one or more of the following are satisfied: 1) the microorganism does not include an endogenous gene encoding an acyl-CoA synthetase, 2) the microorganism includes one or more attenuated genes encoding an acyl-CoA synthetase, and 3) the microorganism does not include an exogenous gene encoding an acyl-CoA synthetase.

Embodiment 7

The method or microorganism of any of embodiments 1-6, wherein the recombinant microorganism does not produce one or both of an acyl-ACP thioesterase and an acyl-CoA thioesterase, further wherein one or more of the following are satisfied: 1) the microorganism does not include an endogenous gene encoding an acyl-CoA thioesterase and/or does not include an endogenous gene encoding an acyl-ACP thioesterase, 2) the microorganism includes an attenuated gene encoding an acyl-CoA thioesterase and/or an attenuated gene encoding an acyl-ACP thioesterase, and 3) the microorganism does not include an exogenous gene encoding an acyl-ACP thioesterase and/or an exogenous gene encoding an acyl-CoA thioesterase.

Embodiment 8

The method or microorganism of any of embodiments 1-7, wherein the non-native nucleic acid sequence encoding the alcohol-forming acyl-ACP reductase is operably linked to a heterologous promoter, wherein the promoter may be from the same species or a different species with respect to the recombinant microorganism.

Embodiment 9

The method or microorganism of any of embodiments 1-8, wherein the non-native nucleic acid sequence comprises a nucleic acid sequence encoding the alcohol-forming acyl-ACP reductase integrated into the genome of the recombinant microorganism such that the acyl-ACP reductase-encoding sequence is operably linked to a promoter endogenous to and within the genome of the recombinant microorganism.

Embodiment 10

The method or microorganism of embodiment 8 or 9, wherein the promoter is regulatable, optionally wherein the promoter is inducible.

Embodiment 11

The method or microorganism of any of the previous embodiments wherein any of the following are satisfied: a) the recombinant microorganism is a cyanobacterium; b) the recombinant microorganism is of an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus* species; c) the recombinant microorganism is a eukaryotic microalga; d) the microorganism is of an *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, or *Volvox* species.

Embodiment 12

The method of any of the previous embodiments, wherein the recombinant microorganism produces at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg of one or more fatty alcohols per liter of culture over a culture period of 1, 2, 3, 4, 5, 6, 7, 8, 9, 10, 11, 12, 13, or 14 days or between about 0.5 mg/L and about 10 g/L, between about 1 mg/L and about 10 g/L, between about 5 mg/L and about 10 g/L, between about 5 mg/L and about 5 g/L, between about 5 mg/L and about 1 g/L, between about 10 mg/L and about 5 g/L, between about 10 mg/L and about 2 g/L, between about 10 mg/L and about 1 g/L or between about 10 mg/L and about 500 mg/L of one or more fatty alcohols/culture, over a period of from about one to about 30 days, optionally from about three to about ten days.

Embodiment 13

The method or microorganism of any of embodiments 1-12, wherein the recombinant microorganism does not express a heterologous fatty aldehyde-forming reductase, optionally wherein the recombinant microorganism expresses a homologous fatty aldehyde-forming reductase, optionally wherein the homologous fatty aldehyde-forming reductase is operably linked to a heterologous promoter optionally wherein said promoter is regulatable, optionally wherein said promoter is inducible.

Embodiment 14

The method or microorganism of any of embodiments 1-12, wherein the recombinant microorganism further comprises an exogenous or endogenous gene encoding a fatty aldehyde-forming reductase, optionally wherein said exogenous or endogenous gene encoding a fatty aldehyde-forming reductase is operably linked to a heterologous promoter, optionally wherein said promoter is regulatable, optionally wherein said promoter is inducible.

Embodiment 15

The method or microorganism of any of the previous embodiments, wherein the recombinant microorganism overexpresses or overproduces at least one endogenous polypeptide selected from: a beta-ketoacyl synthetase; an acetyl-CoA carboxylase; a malonyl-CoA:ACP transacylase; an acyl-ACP synthetase; ribulose 1,5-bisphosphate carboxylase; a phycobiliprotein; acyl carrier protein; and a transmembrane transporter; and/or wherein the recombinant photosynthetic microorganism has attenuated or eliminated expression of at least one gene encoding an enzyme selected from glycerol-3-phosphate dehydrogenase, acetaldehyde-CoA dehydrogenase, pyruvate dehydrogenase and acetate kinase.

Embodiment 16

A method of producing a fatty acid derivative, comprising: culturing a recombinant photosynthetic microorganism that comprises at least one non-native nucleic acid molecule encoding a polypeptide that participates in the synthesis of a fatty acid or a fatty acid derivative and at least one non-native nucleic acid molecule encoding a component of a prokaryotic multidrug resistance transporter or secretion system, or a variant thereof, under conditions in which the non-native genes are expressed; wherein the recombinant photosynthetic microorganism produces a greater amount of a free fatty acid, a fatty alcohol, a fatty aldehyde, or a fatty acid ester than the amount produced by a control photosynthetic microorganism substantially identical to the recombinant photosynthetic microorganism except that the control photosynthetic microorganism does not express a non-native gene encoding a component of a prokaryotic efflux transporter or prokaryotic secretion system; and recovering at least one free fatty acid or fatty acid derivative from the culture medium.

Embodiment 17

A method according to embodiment 16, wherein the recombinant photosynthetic microorganism secretes a greater amount of a free fatty acid, a fatty alcohol, a fatty aldehyde, or a fatty acid ester than the amount secreted by a control photosynthetic microorganism substantially identical to the recombinant photosynthetic microorganism except that the control photosynthetic microorganism does not express a non-native gene encoding a component of a prokaryotic efflux transporter or secretion system or a variant thereof.

Embodiment 18

A method according to embodiment 16 or 17, wherein the prokaryotic multidrug resistance transporter or secretion system is a secondary multidrug resistance transporter, for example a resistance-nodulation-division (RND) efflux transporter, a PET efflux transporter, a small drug resistance (SMR) efflux transporter, or a multi-antimicrobial extrusion (MATE) transporter, for example, an Acr, Mex, or Far efflux transporter, optionally wherein the transporter has at least 80%, at least 85%, at least 90%, at least 95%, at least 96%, at least 97%, at least 98%, or at least 99% identity to SEQ ID NO:19, SEQ ID NO:20, SEQ ID NO:21, SEQ ID NO:27, SEQ ID NO:29, or SEQ ID NO:35.

Embodiment 19

A method according to Embodiment 18, wherein the recombinant photosynthetic microorganism comprises at least one non-native gene encoding three or fewer components, two or fewer components, or a single component of a prokaryotic efflux transporter or secretion system, and/or wherein the recombinant photosynthetic microorganism comprises one or more non-native genes encoding one or more of a membrane fusion protein (MFP), an inner membrane permease protein of a transporter system (IMP) (e.g., an inner membrane permease protein of an RND efflux transporter, or an outer membrane factor (OMF).

Embodiment 20

A method according to embodiment 16 or 17, wherein the prokaryotic multidrug resistance transporter or secretion system is a prokaryotic protein secretion system, for example, a Type VI secretion system (T6SS) of a species of *Acidovorax, Agrobacterium, Burholderia, Erwinia, Psuedomonas, Xanthomonas, Ralstonia, Lysobacter, Azoarcus, Bradyrhizobium, Mesorhizobium, Vibrio,* or *Serratia.*

Embodiment 21

A method according to embodiment 20, wherein the component of a prokaryotic secretion system is a VgrG protein, or a functional variant thereof, including variants having at least 80%, at least 85%, at least 90%, at least 95%, at least 96%, at least 97%, at least 98%, or at least 99% to at least 620, at least 650, or at least 680 amino acids of a VgrG protein of a *Vibrio, Pseudomonas, Burkholderia, Ersinia, Yersinia, Escherishia, Aeromonas, shigella, Marinobacter, Photorhabdus, Mesorhizobium, Photobacteria, Xanthomonas, Ralstonia, Hahella, Geobacter, Salmonella,* or *Shewanella* species, for example, a VgrG protein, or a functional variant thereof, including variants having at least 80%, at least 85%, at least 90%, at least 95%, at least 96%, at least 97%, at least 98%, or at least 99% to at least 620, at least 650, or at least 680 amino acids of SEQ ID NO:37, SEQ ID NO:39, or SEQ ID NO:40.

Embodiment 22

A method according to any of embodiments 16-21, wherein the recombinant microorganism is a photosynthetic microorganism, for example, a microalga or cyanobacterium, optionally wherein cuthreing is under photoautotrophic conditions, for examples using inorganic carbon as substantially the sole source of carbon.

Embodiment 23

A method according to any previous embodiments, further comprising recovering the free fatty acid or fatty acid derivative, optionally wherein recovering the free fatty acid or fatty acid derivative comprises adding an organic solvent to the culture for at least a portion of the culture period, and recovering the solvent to recover the fatty acid derivative, preferably wherein the organic solvent can comprise an alkane, for example, heptane, octane, nonane, decane, dodecane, or tetradecane, and/or a fatty alcohol, for example, octanol, decanol, dodecanol, or tetradecanol.

Embodiment 24

A recombinant microorganism that comprises that comprises at least one non-native nucleic acid molecule encoding a polypeptide that participates in the synthesis of a fatty acid or a fatty acid derivative and at least one non-native nucleic acid molecule encoding a component of a prokaryotic multidrug resistance transporter or secretion system, or a variant thereof; wherein the recombinant photosynthetic microorganism produces and/or secretes a greater amount of a free fatty acid, a fatty alcohol, a fatty aldehyde, or a fatty acid ester than the amount produced by a control photosynthetic microorganism substantially identical to the recombinant microorganism except that the control microorganism does not express a non-native gene encoding a component of a prokaryotic secretion system,

Embodiment 25

The recombinant microorganism of embodiment 24, comprising at least one non-native nucleic acid molecule encoding a component of a prokaryotic multidrug resistance transporter, wherein the prokaryotic multidrug resistance transporter is a secondary multidrug resistance transporter, optionally an SMR transporter or an RND transporter, further optionally wherein at least one component is a membrane fusion protein (MFP), an inner membrane permease protein of a transporter system (IMP) (e.g., an inner membrane permease protein of an RND efflux transporter, or an outer membrane factor (OMF), further optionally wherein at least one component of a secondary multidrug resistance transporter has at least 80%, at least 85%, at least 90%, at least 95%, at least 96%, at least 97%, at least 98%, or at least 99% identity to SEQ ID NO:19, SEQ ID NO:20, SEQ ID NO:21, SEQ ID NO:27, SEQ ID NO:29, or SEQ ID NO:35.

Embodiment 26

The recombinant microorganism of embodiment 24, comprising at least one non-native nucleic acid molecule encoding a component of a prokaryotic protein secretion system, wherein the prokaryotic protein secretion system is a Type VI secretion system (T6SS) of a species of *Acidovorax, Agrobacterium, Burholderia, Erwinia, Psuedomonas, Xanthomonas, Ralstonia, Lysobacter, Azoarcus, Bradyrhizobium, Mesorhizobium, Vibrio,* or *Serratia,* preferably wherein the component of a prokaryotic secretion system is a VgrG protein, or a functional variant thereof, including variants having at least 80%, at least 85%, at least 90%, at least 95%, at least 96%, at least 97%, at least 98%, or at least 99% to at least 620, at least 650, or at least 680 amino acids of a VgrG protein of a *Vibrio, Pseudomonas, Burkholderia, Ersinia, Yersinia, Escherishia, Aeromonas, shigella, Marinobacter, Photorhabdus, Mesorhizobium, Photobacteria, Xanthomonas, Ralstonia, Hahella, Geobacter, Salmonella,* or *Shewanella* species, for example, a functional variant thereof, having at least 80%, at least 85%, at least 90%, at least 95%, at least 96%, at least 97%, at least 98%, or at least 99% to at least 620, at least 650, or at least 680 amino acids of SEQ ID NO:37, SEQ ID NO:39, or SEQ ID NO:40.

Embodiment 26

The recombinant microorganism of any method or microorganism of any of embodiments 16-25, wherein the recombinant microorganism is a photosynthetic microorganism, further wherein optionally any of the following are satisfied: a) the recombinant microorganism is a cyanobacterium; b) the recombinant microorganism is of an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus* species; c) the recombinant microorganism is a eukaryotic microalga; d) the microorganism is of an *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* or *Volvox* species.

In order that this invention may be better understood, the following examples are set forth. These examples are for purposes of illustration only and are not to be construed as limiting the scope of the invention in any manner.

EXAMPLES

Example 1

Expression of Alcohol-Forming Reductase Genes in *E. Coli*

The Maqu_2220 gene (SEQ ID NO: 1) and the Hch_05075 gene (SEQ ID NO: 3) were synthesized by DNA 2.0 in the pJexpress401 vector, which contains the IPTG-inducible T5 promoter (Lanzer and Bujard (1988) Proc. Natl. Acad Sci 85: 8973-8977). *E. coli* K27, a strain that does not produce the *E. coli* acyl-CoA synthetase due to a FadD88 mutation (Cronan (1997) *J. Bacteriol.* 179: 1819-1823), was transformed with the vectors containing the reductase genes. Isolates having the reductase gene constructs were grown overnight in 5 mL tubes in 3 mL of Luria Bertani (LB) media with 50 µg/ml kanamycin, on a shaker at 250 rpm, at 30° C. 1 mL of the overnight culture was inoculated into a 50 mL flask with 10 mL of LB media with 50 µg/ml kanamycin and grown to mid-log growth phase (optical density of 0.6) prior to induction with IPTG. IPTG was added to the mid-log grown culture to a final concentration of 1 mM and the cultures were incubated overnight to a final optical density of 1.8. Optical density was measured at the start and end of the induction period. All 10 mL of the cell culture was centrifuged and resuspended in 0.6 mL water and was transferred to 4 mL GC-vials for GC-fatty alcohol analysis.

Example 2

Analysis of Fatty Acid Samples from *E. Coli*

Fatty alcohols were analyzed by gas chromatography/mass spectroscopy (GC/MS). To a 4 mL glass vial containing concentrated culture, 0.5 mL glass beads, 100 µL 5 M NaCl and 50 µL 50% $H_2SO_4$ were added. The vials were capped and bead-beat for 5 minutes at 1,000 cycles/sec. 2 mL hexane was added, and the vials were again bead-beat for 5 minutes at 1,000 cycles/sec. The vials were then vortexed for 30 minutes at 1,000 rpm, centrifuged at 2,500 rpm for 5 minutes, and then 0.5 mL of the upper organic layer was added to a GC vial. 50 µL of internal standard (1-pentadecanol in $CH_2Cl_2$) was also added to the GC vial, for a final I.S. concentration of 100 µg/mL. The vials were vortexed and analyzed by GC/MS in SIM mode. The GC run conditions were as follows: 1.4 mL/min $H_2$ with an oven temperature of 100° C. for 0.5 min, then ramped at 20° C./min to 270° C. and held for 1 min. The solvent delay was set at 4.3 min. A 0.5 µL injection was made on an inlet set at 280° C. utilizing a 3:1 split and containing a deactivated single gooseneck liner w/glass wool. The GC column was an Agilent HP-5MS, 30 m×0.25 mm×0.25 um. The mass spectrometer scan range was set for m/z of 35-275, the SIM ions monitored were 55.0 and 41.0, and a 10 ms dwell time was used. Analytes were quantified via a 5-point calibration curve from 2-200 µg/mL.

Figure 8:
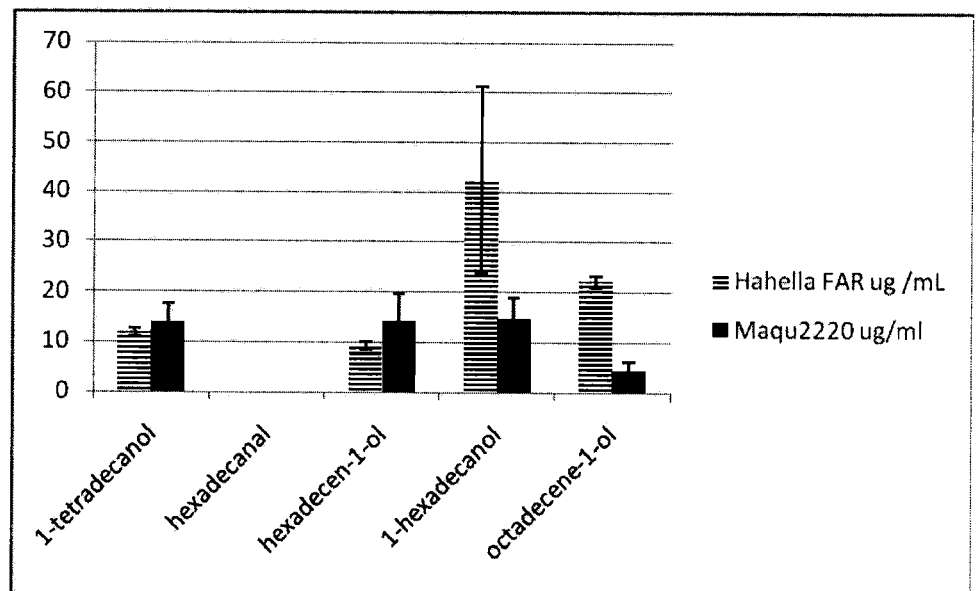
FIG. 8 shows a graph demonstrating the amounts of fatty alcohol of different chain lengths produced in *E. coli* FadD mutant K27 cells expressing the Maqu_2220 (Maqu2220) or Hch_05075 (Hahella FAR) acyl-ACP reductase.

Both Maqu_2220 and Hch_05075 expression in the FadD mutant K27 strain resulted in fatty alcohol production, indicating that both reductases are able to use acyl-ACP as a substrate. The amount of fatty alcohols of different chain lengths produced by *E. coli* K27 cells expressing either Maqu_2220 or Hch_05075 is shown in FIG. 8. Expression of either reductase resulted in production of predominantly C16 fatty alcohols, with expression of the Maqu_2220 reductase resulting in proportionately more C14 fatty alcohol than expression of the Hch_05075 reductase. In *E. coli* K27, expression of Hch_05075 resulted in a greater overall amount of fatty alcohol production by the host cells than expression of Maqu_2220; Hch_05075-transformed *E. coli* K27 cells produced about 80 µg/mL of total fatty alcohol, while Maqu_2220-transformed *E. coli* K27 cells produced approximately 50 µg/mL of total fatty alcohol.

Example 3

Constructs for Expression of Alcohol-Forming Acyl-ACP Reductases in *Synechocystis* sp. PCC 6803

Figure 9:
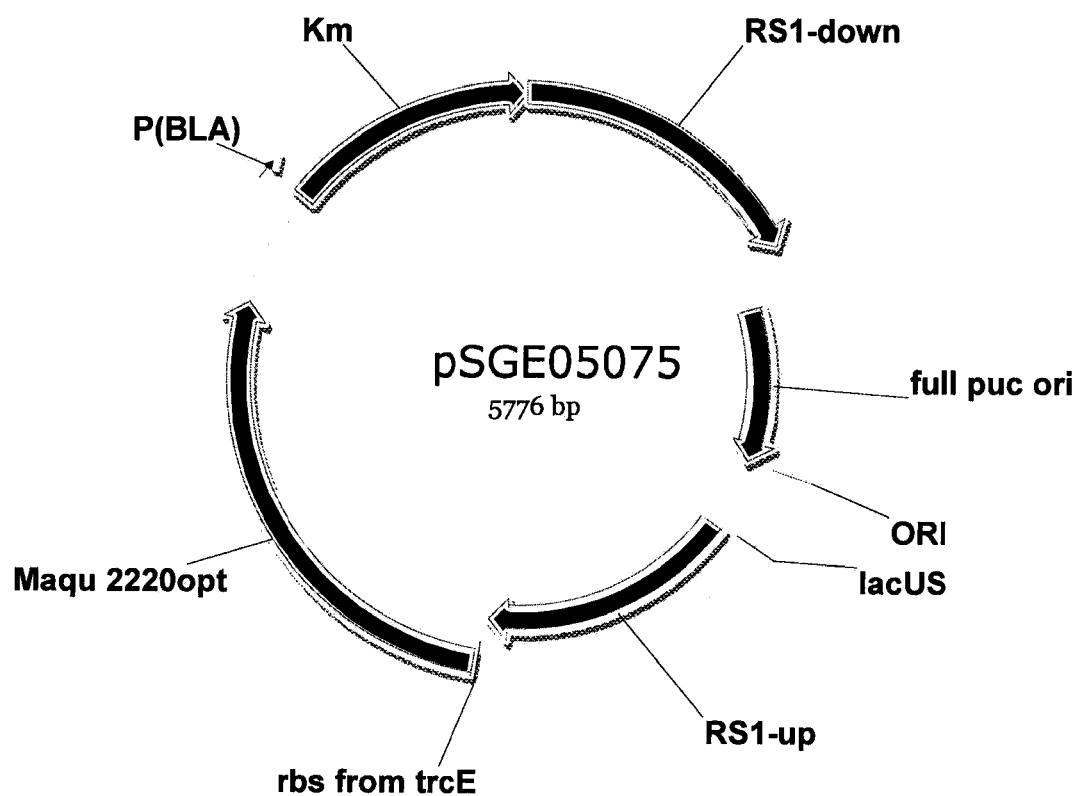
FIG. 9 shows a plasmid map (pSGE05057) of an integration vector built with the codon-optimized Maqu_2220 acyl-ACP reductase gene. RS1-down and RS1-up refer to sequences from the *Synechocystis* sp. PCC 6803 genome that serve as integration sites.

Nucleic acid molecules having a codon optimized Maqu_2220 sequence (SEQ ID NO: 11); a sequence of a *Marinobacter aquaeolei* gene encoding a reductase known to use acyl-CoA as a substrate, Maqu_2507 (SEQ ID NO: 12); or the wild-type Hch_05075 gene sequence (SEQ ID NO: 3) were chemically synthesized by DNA 2.0 (Menlo Park, Calif.). The Maqu_2220 gene (wild-type (SEQ ID NO: 1) and codon-optimized (SEQ ID NO: 11) versions), the Maqu_2507 reductase gene (SEQ ID NO: 12) and the Hch_05075 gene (SEQ ID NO: 3) were individually cloned into the pSGE05141 "RS1" integration vector (FIG. 9). The genes were cloned without the addition of a promoter between "RS1-up" (SEQ ID NO: 14) and "RS1-down" (SEQ ID NO: 15) *Synechocystis* genomic DNA sequences. The RS1 landing region of the *Synechocystis* genome, spanning sequences 2298515 to 2300500 (genome sequence Accession number AP012205.1; GI:339272262) and used for homologous recombination, includes the slr0338 gene of the oxidoreductase family (NAD-binding Rossman fold; NCBI protein accession number BAA10046; gi:1001423) and is proximal to slr0168 (hypothetical open reading frame; NCBI protein accession number BAA10047; gi:1001424). The "RS1-up" sequence includes approximately 830 nucleotides of sequence upstream of the slr0338 gene, as well as approximately 158 nucleotides of the 5' end of the slr0338 gene. Cloning of a gene downstream of this sequence (as depicted in FIG. 9) may allow gene expression sequences from the "RS1-up" genomic sequence to mediate transcription of the reductase transgene.

To introduce the Maqu_2220 wild-type and codon-optimized genes, the Maqu_2507 gene, and the *H. chejuensis* Hch_05075 gene into cyanobacteria, *Synechocystis* sp. PCC 6803 cells were cultured in BG-11 media to an OD (730 nm) of about 0.7-0.9. About 10 mL of the culture was spun down at approximately 2000 g for 15 minutes, then the cell pellet was resuspended in 1 mL fresh BG-11 media. An aliquot of 300 µL of cells was transformed with about 100 ng of integration vector. The cells were incubated under lights (80 µE) for about 6 hours, then spread onto Minipore filters and placed on top of BG-11 agar plates containing no antibiotics. The plates were incubated at about 30° C. under about 80 µE of light for about 24 hours. The filters were then transferred onto fresh BG-11 1.5% agar plates with 20 µg/mL kanamycin and cultured for 7 days. Colonies of *Synechocystis* sp. PCC 6803 were picked and patched onto new agar plates.

TABLE 1

| ATCC 616 Medium BG-11 for Cyanobacteria | |
|---|---|
| $NaNO_3$ | 1.5 g |
| $K_2HPO_4$ | 0.04 g |
| $MgSO_4 * 7H_2O$ | 0.075 g |
| $CaCl_2 * 2H_2O$ | 0.036 g |
| Citric acid | 6.0 mg |
| Ferric ammonium citrate | 6.0 mg |
| EDTA | 1.0 mg |
| $Na_2CO_3$ | 0.02 g |

TABLE 1-continued

ATCC 616 Medium BG-11 for Cyanobacteria

| Trace Metal Mix A5# | 1.0 ml |
|---|---|
| Agar (if needed) | (up to) 10.0 g |
| Distilled water | 1.0 L |

Trace Metal Mix A5
$H_3BO_3$ 2.86 g
$MnCl_2 * 4H_2O$ 1.81 g
$ZnSO_4 * 7H_2O$ 0.22 g
$Na_2MoO_4 * 2H_2O$ 0.39 g
$CuSO_4 * 5H_2O$ 0.080 g
$Co(NO_3)_2 * 6H_2O$ 49.4 mg
Distilled water to 1.0 L

Example 4

Fatty Alcohol Production by *Synechocystis* Sp. PCC 6803 Strains Expressing Alcohol-Forming Acyl-ACP reductases Cultures of *Synechocystis* sp. PCC 6803 transformed with the Maqu_2220 wild type gene, the Maqu_2220 codon-optimized gene, or the Maqu_2507 gene were grown for testing fatty alcohol production. Three different colony patches for each clone were inoculated into 20 mL glass scintillation vials containing 10 mL of BG-11 liquid media with 50 µg/ml kanamycin. Cultures were covered with filter floss tape. BG-11 medium, which does not include a substantial amount of a reduced carbon source, supports photoautotrophic growth of *Synechocystis*. The scintillation vials were incubated at about 30° C. with about 5% ambient $CO_2$ and continuously shaken at about 200 rpm under about 70 µE of light for 7 days. 5 mL of each culture were then spun down at approximately 5000 rpm and resuspended in 0.4 mL of water, then extracted by a hexane/sulfuric acid solvent system to extract neutral lipids.

Example 5

Gas Chromatography of *Synechocystis* Sp. PCC 6803 Expressing an Alcohol-Forming Acyl-ACP reductase

*Synechocystis* sp. PCC 6803 strains grown as described above were analyzed by gas chromatography for fatty alcohol production.

Figure 10:
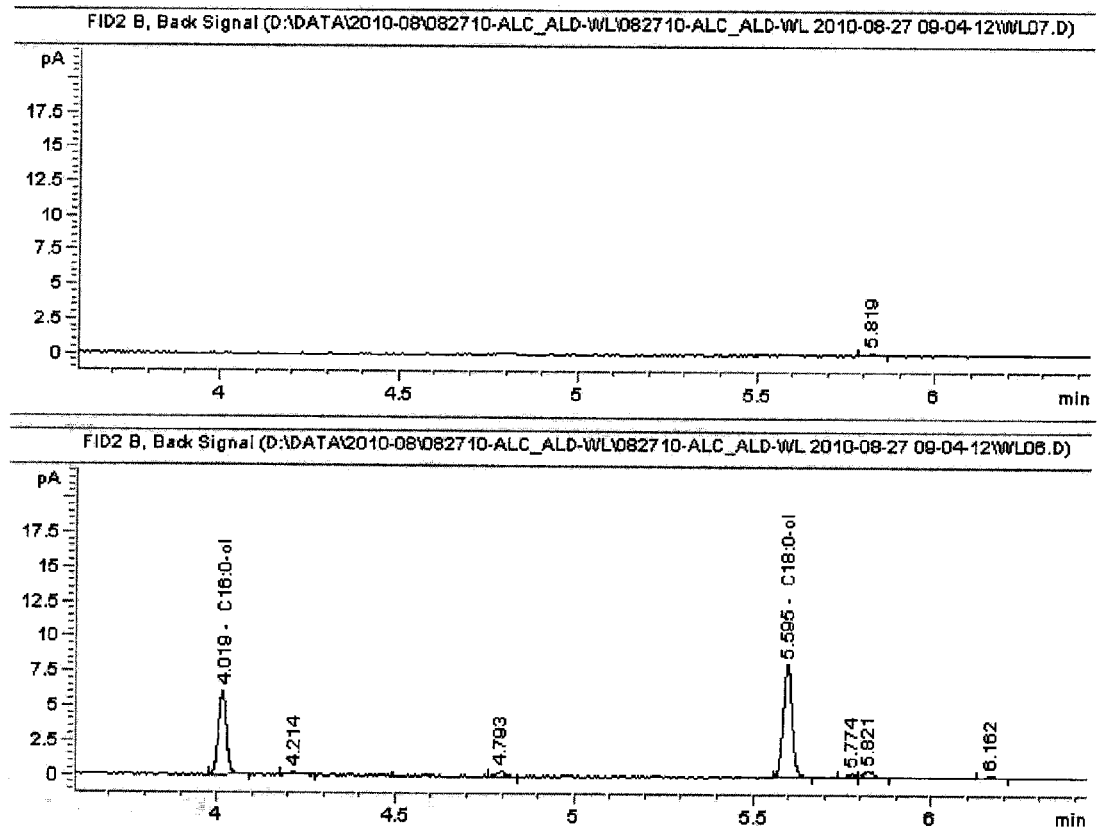
FIG. 10 A) shows a gas chromatography chromatogram of *Synechocystis* sp. PCC 6803 grown phototrophically and expressing a codon-optimized gene encoding a Maqu_2507 acyl-CoA reductase (SEQ ID NO: 12). B) shows a gas chromatography chromatogram of *Synechocystis* sp. PCC 6803 grown phototrophically and expressing a gene encoding the Maqu_2220 acyl-ACP reductase (SEQ ID NO: 11). Lipid products are marked vertically for each peak.

A seed dispenser and a 2.0 mL centrifuge tube were used to add 0.5 mL of 212-300 µm acid-washed glass beads to the samples. Subsequently 50 µL of 50% $H_2SO_4$ and 100 µL of 5 M NaCl were added. Samples were placed in the 2010 model SPEX GenoGrinder and bead beat for 5 min at 1000 rpm in order to lyse the cells. After bead beating, 2 mL of hexanes were added, the vials were capped, and bead-beating was repeated for 5 min at 1000 rpm. The samples were then vortexed on a multi-tube vortexer for 30 min at 1000 rpm and then 30 sec at 2500 rpm. Next the samples were centrifuged for 4 min at 2000 rpm. 0.5 mL of the hexanes (upper) layer were transferred to a 2.0 mL GC vial and 50 tit of internal standard (1 mg/mL 1-Pentadecanol in $CH_2Cl_2$) were added for a final concentration of internal standards of 100 µg/mL. The vials were then vortexed and analyzed by GC/MS-SCAN/SIM. The GC run conditions were as follows: 1.4 mL/min H2 with an oven temperature of 100° C. for 0.5 min, then ramped at 20° C./min to 270° C. and held for 1 min. The solvent delay was set at 4.3 min. A 1 µL injection was made on an inlet set at 280° C. utilizing a 3:1 split and containing a deactivated single gooseneck liner w/glass wool. The GC column was an Agilent HP-5MS, 30 m×0.25 mm×0.25 µm. The mass spectrometer scan range was set for m/z of 35-275, the SIM ions monitored were 55.0 and 41.0, and a 10 ms dwell time was used. Analytes were quantified via a 5-point calibration curve from 2-200 µg/mL. FIG. 10 shows a GC trace of *Synechocystis* transformed with the Maqu_2507 acyl-CoA reductase gene, showing no fatty alcohol peaks, above a GC trace of the extract of one of the isolates having the codon-optimized Maqu_2220 gene, which shows peaks for C16 and C18 fatty alcohols.

Figure 11:
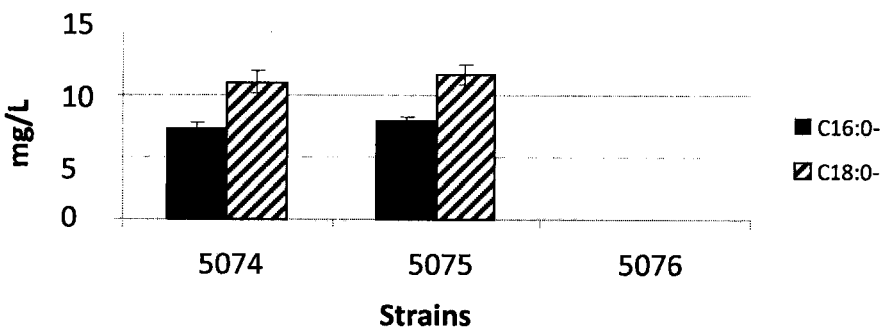
FIG. 11 shows a graph demonstrating the amounts of fatty alcohol (C16:0 and C18:0-ol) produced in *Synechocystis* sp. PCC 6803 expressing wild-type (5074) or 6803 codon-optimized (5075) genes encoding Maqu_2220 acyl-ACP reductases, compared to *Synechocystis* sp. PCC 6803 expressing a gene encoding Maqu_2507 (5076), an acyl-CoA reductase that uses acyl-CoA as a substrate. No fatty aldehyde was detected in any of the samples.

FIG. 11 shows that expression of both wild-type (5074 isolates) and codon-optimized Maqu_2220 (5075 isolates) in *Synechocystis*, which lacks acyl-CoA, resulted in the production of C16 and C18 alcohols. By contrast, expression of Maqu_2507 (5076 isolates) did not result in any detectable alcohol production, demonstrating that the Maqu_2507 reductase (SEQ ID NO: 13) did not produce detectable levels of fatty alcohols in a 7 day culture of *Synechocystis*, a species that does not produce acyl-CoA.

Example 6

Fatty Alcohol Production in *Synechocystis* Sp. PCC 6803 Strains Expressing an Alcohol-Forming Acyl-ACP Reductase

*Synechocystis* sp. PCC 6803 cells comprising the Hch_05075 gene were grown in 25 mL of BG-11 media in 125 mL glass flasks, shaking under about 80 µE of light in the presence of 1% $CO_2$, for ten days. The entire culture was spun down and resuspended in 0.4 mL of water and then extracted by a hexane/sulfuric acid solvent system to extract neutral lipids. As a control, the *Synechocystis* sp. PCC 6803 strain lacking a reductase gene construct was cultured and extracted by the same method.

Figure 12:
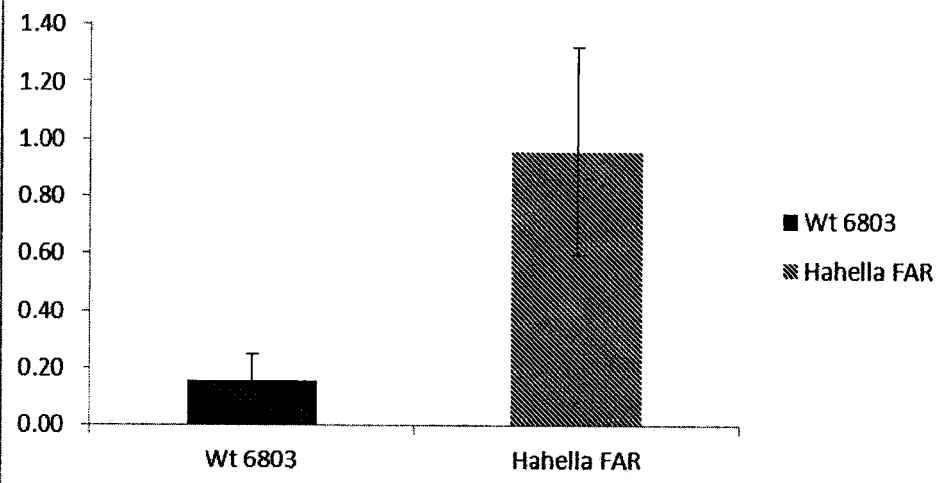
FIG. 12 shows a graph demonstrating total fatty alcohol produced in *Synechocystis* sp. PCC 6803 expressing no heterologous acyl-ACP reductase ("Wt 6803"), or expressing Hch_05075 ("Hahella FAR").

FIG. 12 demonstrates the production of fatty alcohol by *Synechocystis* sp. PCC 6803 carrying the Hch_05075 reductase gene (SEQ ID NO: 3), with negligible production of fatty alcohol detected in the non-transformed host strain.

Example 7

Cloning and Expression of the "Mex" RND Efflux System in *Synechocystis*

Figure 13:
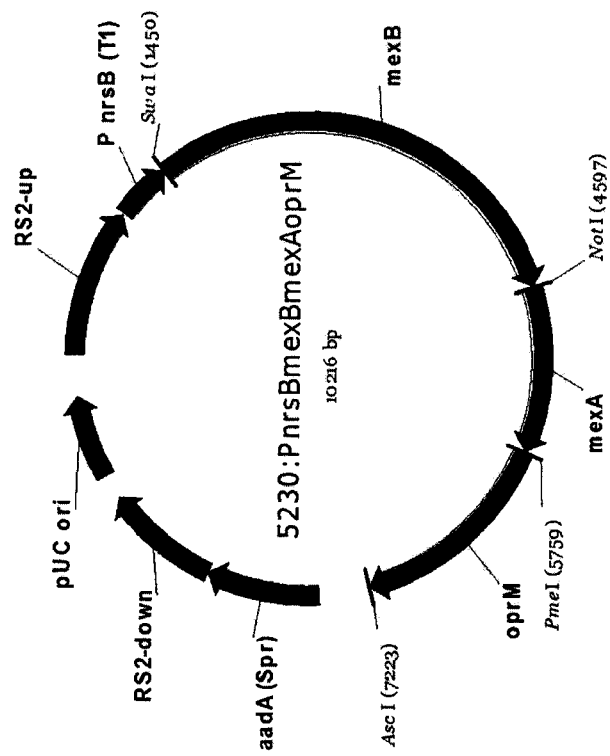
FIG. 13 is a schematic of a construct for integration into the cyanobacterial genome that includes the *Psuedomonas* mexBAorpM operon linked to a cyanobacterial nrsB (nickel-regulated) promoter.

A construct that included genes encoding the mexB, mexA, and oprM proteins (SEQ ID NO:19; SEQ ID NO:20; and SEQ ID NO:21, respectively) of *Pseudomonas aeruginosa* in a tandem arrangement (SEQ ID NO:18) was synthesized by DNA 2.0 (Burlingame, Calif.). The three gene transcriptional unit was operably linked to a *Synechocystis* nrsB promoter sequence (SEQ ID NO:22) amplified from *Synechocystis* PCC 6803 genomic DNA in a vector that included a pUC origin of replication for *E. coli*. The "5230" vector (FIG. 13) also included the aadA spectinomycin resistance gene and "RS2 up" (SEQ ID NO:16) and "RS2 down" (SEQ ID NO:17) sequences flanking the Pnrs-mexBAoprM operon and aadA selectable marker to mediate integration of the PnrsB-mexBmexAoprM operon and selectable marker into the genome.

Figure 14:
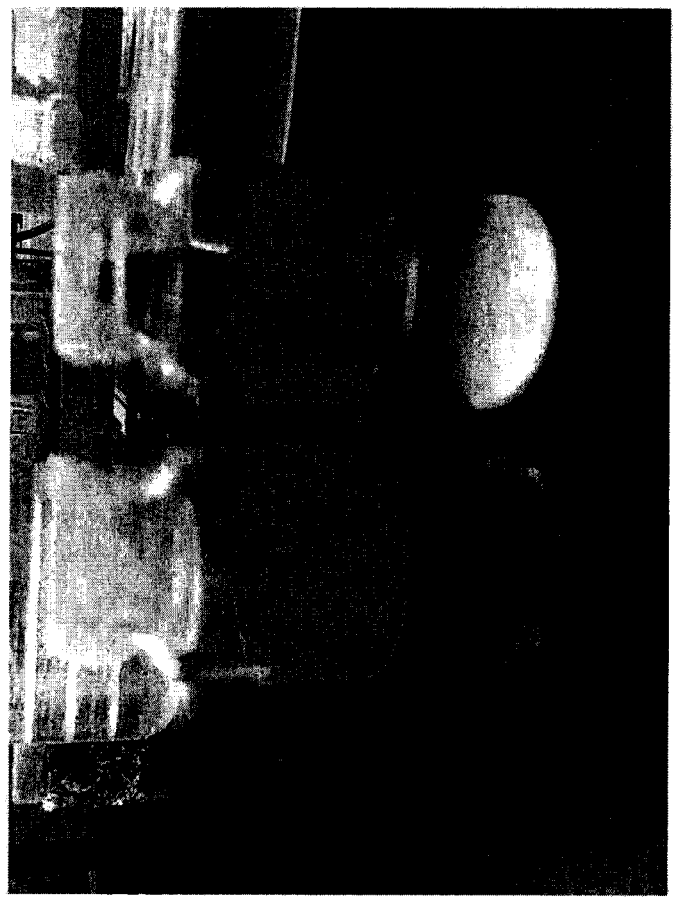
FIG. 14 is a picture of cyanobacterial cultures grown in the presence of 0.0325% terpinen-4-ol. The culture on the left expressed the *Psuedomonas* mexBAorpM genes and was green in color, while the culture on the right, which did not include the *Psuedomonas* mexBAorpM operon, was completely clear.

The mex operon-containing 5230 vector (FIG. 13) was transformed into *Synechocystis* PCC 6803 cells essentially as provided in Example 3. To test the functionality of the mex-BAoprM efflux system in *Synechocystis*, transformed cells were grown in BG-11 media that included 100 µg/mL spectinomycin for maintaining selection for the integration construct and 25 µM nickel chloride to induce expression of the mexA-mexB-orpM operon, as well as 0.0325% terpinen-4-ol, an antiseptic compound that an active mex efflux system can provide resistance to (Papadopoulos et al. (2008) *Appl Environ Microbiol* 74: 1932-1935). As a control, *Synechocystis* PCC 6803 cells transformed with an "empty vector" that included the aadA selectable marker and RS2 integration sequences, but did not include the Pnrs-mexBAoprM operon, were also grown in BG-11 media that included 100 µg/mL specitinomycin, 25 µM nickel chloride, and 0.0325% terpinen-4-ol. FIG. 14 shows a dramatic difference in the culture in the vial on the left, which was visibly green and can be seen as dark in the figure, containing cells expressing the mex efflux system, in which the cells were able to tolerate the antiseptic, versus the clear culture in the vial on the right, which was inoculated with cells not expressing the mex efflux components, in which the cells were clearly unable to survive the presence of the compound.

Example 8

Co-Expression of the "Mex" RND Efflux System and an Acyl-ACP Thioesterase in *Synechocystis*

The mex operon-containing 5230 vector (FIG. 13) was transformed into *Synechocystis* PCC 6803 cells that carried the N-terminally truncated Cc1FatB1 thioesterase gene (SEQ ID NO:23) operably linked to the IPTG-regulatable TrcY promoter (SEQ ID NO:25) integrated into the *Synechocystis* RS2 integration site (see, for example, US Patent Application publication US 2012/0184003, incorporated by reference herein). Transformation of *Synechocystis* PCC 6803 was performed essentially as provided in Example 3 and transformants were screened by PCR with gene-specific primers to confirm the presence of the transgenes.

Starter cultures of *Synechocystis* transformed with both the mexB-mexA-oprM operon (SEQ ID NO:18) operably linked to the nrsB promoter (SEQ ID NO:22) and the Cc1FatB1 thioesterase gene (SEQ ID NO:23) operably linked to the TrcY promoter (SEQ ID NO:25), as well as cultures of a *Synechocystis* control strain that included just the TrcY-regulated Cc1FatB1 thioesterase gene were used to inoculate 10 mL cultures at an O.D. of 0.6 (730 nm). The cyanobacterial cells were grown in selective BG11 media (Table 1) containing 50 µg/ml kanamycin for selection of the construct that included Cc1FatB1 thioesterase gene and 100 µg/ml specitinomycin for selection of the vector insertion including the mexBAorpM operon. The 10 mL cultures were grown in 20 mL scintillation vials. After one day of culturing, IPTG was added to a final concentration of 1 mM to induce expression of the Cc1FatB1 thioesterase gene and nickel chloride was added to the cultures to a final concentration of 25 µM to induce expression of the mexBAorpM operon (25 µM nickel chloride was also added to the control cultures that did not include the mexBAorpM operon). The cultures were grown for an additional five days, shaking at 150 rpm at 30° C. with constant illumination (40 µEinsteins m$^{-2}$ sec$^{-1}$). On the final day of culturing, 1 mL of dodecane was added to the approximately 9 mL cultures.

At the end of the culture period, the dodecane layer at the top of the culture vial was pipeted into a fresh vial for fatty acid determination. The remaining culture was spun down and the supernatant was removed to determine the fatty acid content of the aqueous media. Free fatty acids were analyzed by gas chromatography (GC) with flame ionization detection (GC-FID).

An internal standard (I.S.) set that included the free fatty acids C9:0, C13:0, and C17:0, each at a concentration of 600 µg/ml, in hexane, were added to the dodecane samples such that the final concentration of each I.S. was 50 µg/ml relative to sample volume. The fatty acids for making the I.S. set were purchased from Fluka or Nu-Chek Prep, Inc. C8:0 and C10:0 fatty acids were calibrated with C9:0 I.S.; C12:0 and C14:0 fatty acids used the C13:0 I.S.; and the remaining C16:0 through C18:2 cis9,12 fatty acids used the C17:0 I.S. Post I.S. addition, the cultures were vortexed on a multi-tube vortexer at 2,500 rpm for 30 min. The dodecane extracts were sampled by a Gerstel MPS2L Autosampler.

The remaining approximately 9 mL culture for each sample was centrifuged for 5 min at maximum speed. The supernatant was collected in a fresh flask to which 15 mL of methylene chloride was added and the mixture was vortexed. The mixture was then allowed to separate and the organic bottom layer was collected and put into a 20 mL scintillation vial. The organic layers from the culture supernatants were concentrated by flushing with nitrogen, and once dried 1 mL of methylene chloride was added to each sample, after which the samples were vortexed and then added to a 1 mL GC vial. Internal standards as provided above were added to a final concentration of 50 µg/ml of each standard relative to sample volume, the cultures were vortexed on a multi-tube vortexer at 2,500 rpm for 30 min, and the aqueous media extracts resuspended in methylene chloride were sampled by a Gerstel MPS2L Autosampler.

Fatty acid samples were analyzed on an Agilent model 7890A gas chromatograph equipped with an FID (flame ionization detector) that included a J&W Scientific DB-FFAP capillary column (10 m length, 0.10 mm internal diameter, 0.10 µm film thickness). The GC oven was programmed as follows: 120° C. for 0.1 min., then heated at 40° C./min. to 240° C. (hold 3 minutes). The injector temperature was kept at 250° C., and a 40:1 split 1.0 µl injection was used. Hydrogen was used as a carrier gas at a flow rate of 0.5999 ml/min. The FID was set to 320° C. The analytes were identified by comparison of retention times to individually injected standards. The calibration range for the analytes was 2.5 µg/ml to 200 µg/ml for C8:0-C16:1 fatty acids and 0.625 µg/ml to 50 µg/ml for C18:0-C18:2 fatty acids. The limit of quantitation for each analyte was the lowest concentration listed in the calibration range except C18:0, C18:1 cis9 (1.25 ug/mL) and C18:2 cis9,12 (2.5 ug/mL). Spiking and recovery experiments into whole cell culture showed that the extraction method recovered consistently within a range of 85%-115% for each analyte in this sample batch run except C16:1 cis9 (74%), C18:1 cis9 (63%), and C18:2 cis9,12 (64%).

Figure 15:
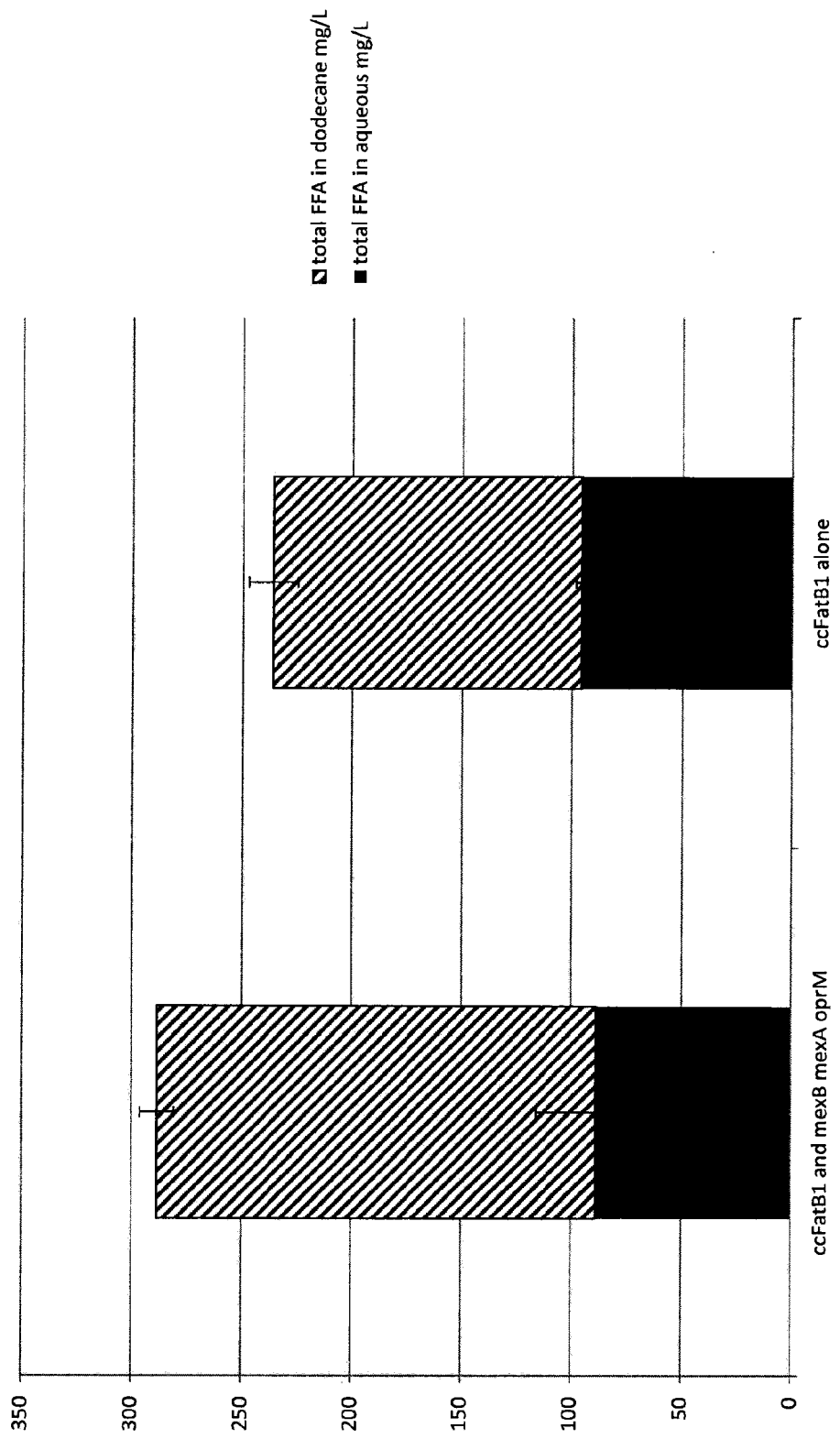
FIG. 15 shows a graph demonstrating increased secretion of fatty acids by a *Synechocystis* PCC 6803 strain that expresses the mexB-mexA-oprM genes as well as a heterologous acyl-ACP thioesterase. The striped portion of the bars represents free fatty acids captured in a dodecane layer, and the solid portion of the bars represents the free fatty acids that were recovered from the aqueous media. The bars are the average of three culture samples, the amounts are calculated to refer to culture volume.

FIG. 15 shows the results of expressing the mex/orp secretion system on the production of fatty acids by a *Synechocystis* strain that also expresses a heterologous thioesterase. Expression of the mexBmexAorp genes in *Synechocystis* strains that also expressed an acyl-ACP thioesterase gene resulted in a higher level of free fatty acids being produced than in control cells that expressed the thioesterase gene but lacked an exogenous secretion system. The figure also indicates that the majority of the secreted fatty acids go into an organic layer when dodecane is provided in the media. This suggests that secreted fatty acids and fatty acid derivatives that are secreted can be recovered by adding organic solvents to the culture that can be present during at least a portion of the production period using methods that do not require cell harvesting or lysis.

Example 9

Overexpression of an Endogenous RND Efflux System in *Synechocystis*

Transcriptomics of *Synechocystis* PCC 6803 expressing the heterologous acyl-ACP thioesterase gene Cc1FatB1 (SEQ ID NO:23) and producing free fatty acids revealed that an endogenous efflux system was overexpressed with respect to control cells that did not express an exogenous acyl-ACP thioesterase. The overexpressed genes, denoted as sll0141 and sll0142 (genome.kazusa.or.jp/cyanobase/Synechocystis) occur in a tandem arrangement in an operon in the *Synechocystis* genome. 5110141 was found to recruit to TIGR-FAM 01730 "efflux transporter, RND family, MFP subunit" (jcvi.org/cgi-bin/tigrfams/HmmReportPage.cgi?acc=TIGRO1730) and sll0142 was found to recruit to Pfam PF00873 "AcrB/AcrD/AcrF family" (http://pfam.sanger.ac.uk/family/PF00873). These proteins are thus classified under the RND superfamily according to the transporter classification database (www.tcdb.org/search/result.php?tc=2.A.6). We refer to the encoded proteins as RND-MFP 175 ("RND efflux transporter family, membrane fusion protein 175") and RND-IMP 174 ("RND efflux transporter family, inner membrane permease 174"), respectively.

Figure 16:
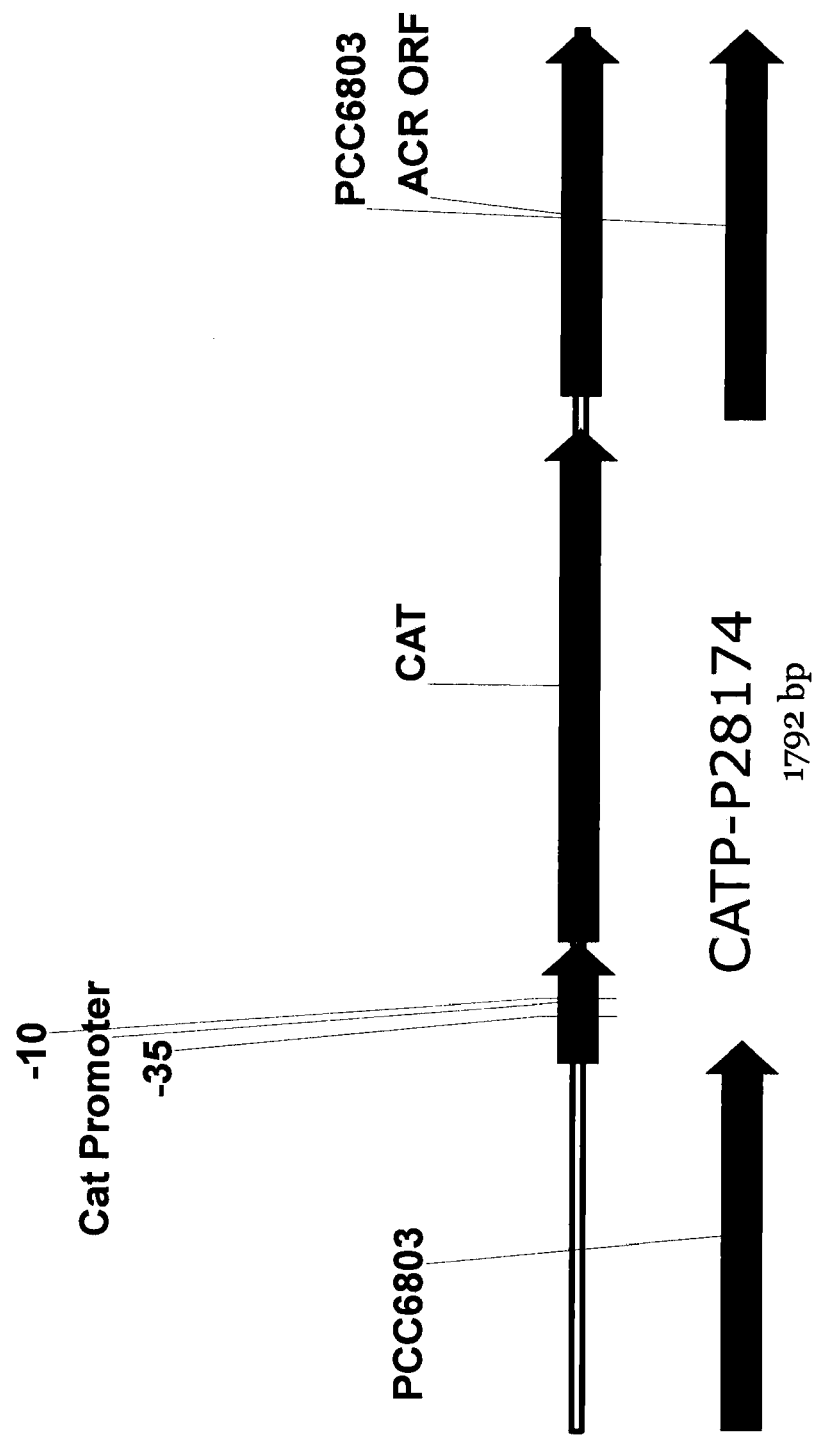
FIG. 16 is a schematic of a construct for integration into the *Synechocystis* genome for overexpressing the endogenous RND-IMP-174 gene (s1101452), encoding an inner membrane permease component of an RND transporter.

To determine the effects of forced overexpression of a component of this cyanobacterial efflux system, we generated a construct (SEQ ID NO:30) that includes a constitutive chloramphenicol acetyltransferase ("CAT") promoter (SEQ ID NO:31) driving a chloramphenicol acetyl transferase gene (SEQ ID NO:32) flanked (upstream of the CAT promoter) by sequences that occur upstream of the native *Synechocystis* RND-IMP 174 gene (sll0142). These upstream flanking sequences (SEQ ID NO:33) include a portion of the open reading frame of the upstream RND-MFP 175 gene (sll0141). The construct also includes, downstream of the CAT promoter—CAT gene cassette, sequences of the *Synechocystis* genome that include nucleotides upstream of the RND-IMP 174 gene plus nucleotide sequences encoding the first amino acids of the RND-IMP 174 protein (SEQ ID NO:34). A schematic of the integration construct for the chloramphenicol promoter and gene flanked by genomic "PCC6803" sequences for integration into the *Synechocystis* PCC 6803 genome is provided in FIG. 16. Thus, the construct is designed to insert the CAT cassette between the RND-MFP 175 (sll0141; SEQ ID NO:26) and RND-IMP 174 (sll0142; SEQ ID NO:28) genes, to drive expression of the downstream RND-IMP 174 gene with the CAT promoter.

The construct was transformed into *Synechocystis* strain ("158") that included the Cc1FatB1 acyl-ACP thioesterase gene (SEQ ID NO:23) plus a kanamycin resistance gene integrated into the RS1 site of the genome, as well as *Synechocystis* strain ("160") that included an oil palm acyl-ACP thioesterase gene plus a kanamycin resistance gene integrated into the RS1 site of the genome, essentially according to Example 3. *Synechocystis* strains engineered to overexpress a component of the endogenous RND efflux system (RND-IMP 174; SEQ ID NO:29) in addition to either the Cc1FatB1 acyl-ACP thioesterase or the Oil Palm acyl-ACP thioesterase, and control strains including the integrated inducible Cc1FatB1 gene or oil palm acyl-ACP thioesterase gene but not engineered to overexpress the endogenous RND transporter component, were cultured to determine whether overexpression of a component of the endogenous RND efflux system resulted in higher free fatty acid production levels.

Starter cultures of *Synechocystis* transformed with both the CAT cassette integrated to regulate the endogenous RETF-IMP 174 transporter gene (SEQ ID NO:28) and the heterologous Cc1FatB1 thioesterase gene (SEQ ID NO:23) operably linked to the TrcY promoter (SEQ ID NO:25), as well as cultures of a *Synechocystis* control strain that included just the TrcY-regulated Cc thioesterase gene were used to inoculate 10 mL cultures at an O.D. of 0.6 (730 nm). Additional cultures of *Synechocystis* transformed with both the CAT cassette construct (SEQ ID NO:30) integrated to regulate the endogenous RETF-IMP 174 transporter gene (SEQ ID NO:28) and the heterologous oil palm thioesterase gene operably linked to the TrcY promoter, as well as cultures of a *Synechocystis* control strain that included just the TrcY-regulated oil palm thioesterase gene were used to inoculate additional 10 mL cultures at an O.D. of 0.6 (730 nm). The cyanobacterial cells were grown in selective BG11 media (Table 1; containing 20 µg/ml kanamycin for selection of the construct that included Cc1FatB1 thioesterase gene, and 20 µg/ml chloramphenicol for selection of the vector insertion including the CAT promoter. IPTG was added to a final concentration of 1 mM at the beginning of the culturing period to induce expression of the thioesterase gene, and all cultures also included 20 µg/ml kanamycin to select for the Cc1FatB1 gene. The cultures were grown in 20 mL scintillation vials for 6 days, shaking at (150 rpm) at 30° C. with constant illumination (40 µEinsteins m$^{-2}$ sec$^{-1}$). Free fatty acids were analyzed by gas chromatography (GC) with flame ionization detection (GC-FID).

1 mL aliquots of cultures in 4 mL vials capped with PTFE (polytetrafluoroethylene)-lined caps (National Scientific) were submitted to Analytical for analysis. Eighty four microliters of an internal standard (I.S.) set that included the free fatty acids C9:0, C13:0, and C17:0, each at a concentration of 600 µg/ml, in hexane, were added to the culture sample, followed by 83 microliters of 50% $H_2SO_4$, 167 microliters of 5 M NaCl, and 1.4 milliliters of hexane. The final concentration of each I.S. was 50 µg/ml relative to the sample volume. The fatty acids for making the I.S. set were purchased from Fluka or Nu-Chek Prep, Inc. C8:0 and C10:0 fatty acids were calibrated w/C9:0 I.S.; C12:0 and C14:0 fatty acids used the C13:0 I.S.; and the remaining C16:0 through C18:2 cis9,12 fatty acids used the C17:0 I.S. Post reagent and I.S. addition, the cultures were vortexed on a multi-tube vortexer at 2,500 rpm for 30 min. The vials were finally centrifuged for 3 min. at 2500 rpm to provide good separation between organic and aqueous phases. The hexane layers were sampled by a Gerstel MPS2L Autosampler.

Fatty acid samples were analyzed on an Agilent model 7890A gas chromatograph equipped with an FID (flame ionization detector) that included a J&W Scientific DB-FFAP capillary column (10 m length, 0.10 mm internal diameter, 0.10 µm film thickness). The GC oven was programmed as follows: 120° C. for 0.1 min., then heated at 40° C./min. to 240° C. (hold 3 minutes). The injector temperature was kept at 250° C., and a 40:1 split 1.0 µl injection was used. Hydrogen was used as a carrier gas at a flow rate of 0.5999 ml/min. The FID was set to 320 C. The analytes were identified by comparison of retention times to individually injected standards. The calibration range for the analytes was 2.5 µg/ml to 200 µg/ml for C8:0-C16:1 fatty acids and 0.625 µg/ml to 50 µg/ml for C18:0-C18:2 fatty acids. The limit of quantitation for each analyte was the lowest concentration listed in the calibration range except C18:0, C18:1 cis9 (1.25 ug/mL) and C18:2 cis9,12 (2.5 ug/mL). Spiking and recovery experiments into whole cell culture showed that the extraction method recovered consistently within a range of 85%-115% for each analyte in this sample batch run except C16:1 cis9 (74%), C18:1 cis9 (63%), and C18:2 cis9,12 (64%).

Figure 17:
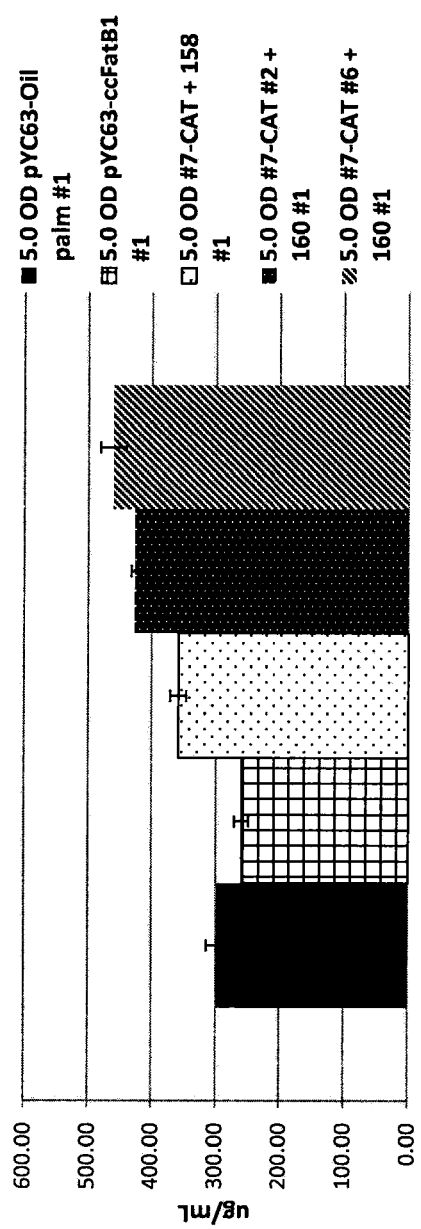
FIG. 17 is a graph depicting production of free fatty acids by cyanobacteria expressing an exogenous acyl-ACP thioesterase gene and overexpressing the RND-IMP-174 gene (s1101452), encoding an inner membrane permease component of an RND transporter (three rightmost bars, labeled "CAT"), versus controls expressing only a thioesterase gene (two leftmost bars).

FIG. 17 shows the results of overexpressing the cyanobacterial and RETF-IMP 174 transporter gene on the production of fatty acids by a *Synechocystis* strain that also expresses a heterologous thioesterase. Overexpression of the RETF-IMP 174 transporter gene in *Synechocystis* strains that also expressed an acyl-ACP thioesterase gene resulted in a higher level of free fatty acids being produced than in control cells that expressed the thioesterase gene but lacked an exogenous secretion system, most likely due to their removal from the cell by the RND pump.

Example 11

Figure 18:
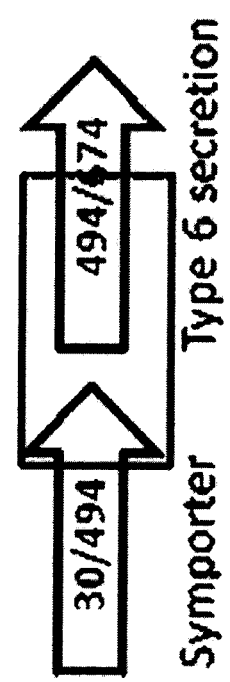
FIG. 18 is a schematic of the insert in a clone of a *Pseudomonas* strain library that includes a portion of an open reading frame for a VsrG protein of a Type VI Secretion System.

Discovery of a *Pseudomonas* Secretion Component that Affects Fatty Acid and Fatty Acid Derivative Secretion In an effort to discover genes that could effect secretion of fatty alcohols, *E. coli* Top 10 chemically competent cells (Life Technologies, Carlsbad, Calif.; genotype F-mcrA Δ(mrr-hsdRMS-mcrBC) Φ80 lacZΔM15 ΔlacX74 recA1 araD139 Δ(ara leu) 7697 galU galK rpsL (StrR) endA1 nupG) were co-transformed with 1) a construct that included the Maqu 2220 reductase gene (SEQ ID NO:1) under the control of the constitutive T5 promoter (Lanzer and Bruyard (1988) *Proc. Natl. Acad Sci USA* 85: 8973-8977) in the pac plasmid that includes a selectable marker for chloramphenicol resistance and 2) a multi-strain bacterial library generated cloning isolated genome fragments of 489 independently grown *Pseudomonas* or *Pseudomonas*-related bacterial strains in a puK vector that includes a kanamycin resistance gene (see US 2012/0184003, incorporated herein by reference). The co-transformation was plated on agar plates that included both kanamycin (50 μg/mL) and chloramphenicol (20 μg/mL) to select for the presence of both the Maqu 2220 gene and a library insert plasmid. Colonies were plated on plates containing and Nile Red, a dye that fluoresces on binding neutral lipids. One of the clones exhibiting a high level of fluorescence was selected for further analysis. Sequencing of the library insert of this clone revealed that the cloned fragment encoded a portion of the Type VI Secretion System operon of *Pseudomonas fluorescens* (FIG. 18). The insert (SEQ ID NO:36), encoded the C-terminal most amino acids of a symporter gene and the major portion of a Type VI Secretion System (T6SS) (SEQ ID NO:37) component known as VgrG protein.

To determine whether the library fragment allowed for greater fatty alcohol secretion, triplicate cultures of this *E. coli* clone as well as triplicate cultures of a control strain that included the Maqu 2220 reductase gene construct were grown in 5 mL cultures in LB medium containing 50 μg/mL kanamycin and 20 ug/mL chloramphenicol to which 1 mL of dodecane was added at 30° C. with shaking. The bacterial cultures were grown in capped glass vials to an OD of 1.8.

At the end of the culture period, the dodecane layer was removed from the culture and submitted for neutral lipid analysis by GC. 0.5 mL of the dodecane layer was transferred to a 2.0 mL GC vial and 50 μL of internal standard (1 mg/mL 1-Pentadecanol in $CH_2Cl_2$) were added for a final concentration of internal standards of 100 mg/mL. The vials were then vortexed and analyzed by GC/MS-SCAN/SIM. The GC run conditions were as follows: 1.4 mL/min H2 with an oven temperature of 100° C. for 0.5 min, then ramped at 20° C./min to 270° C. and held for 1 min. The solvent delay was set at 4.3 min. A 1 μL injection was made on an inlet set at 280° C. utilizing a 3:1 split and containing a deactivated single gooseneck liner w/glass wool. The GC column was an Agilent HP-5MS, 30 m×0.25 mm×0.25 μm. The mass spectrometer scan range was set for m/z of 35-275, the SIM ions monitored were 55.0 and 41.0, and a 10 ms dwell time was used. Analytes were quantified via a 5-point calibration curve from 2-200 μg/mL.

Figure 19:
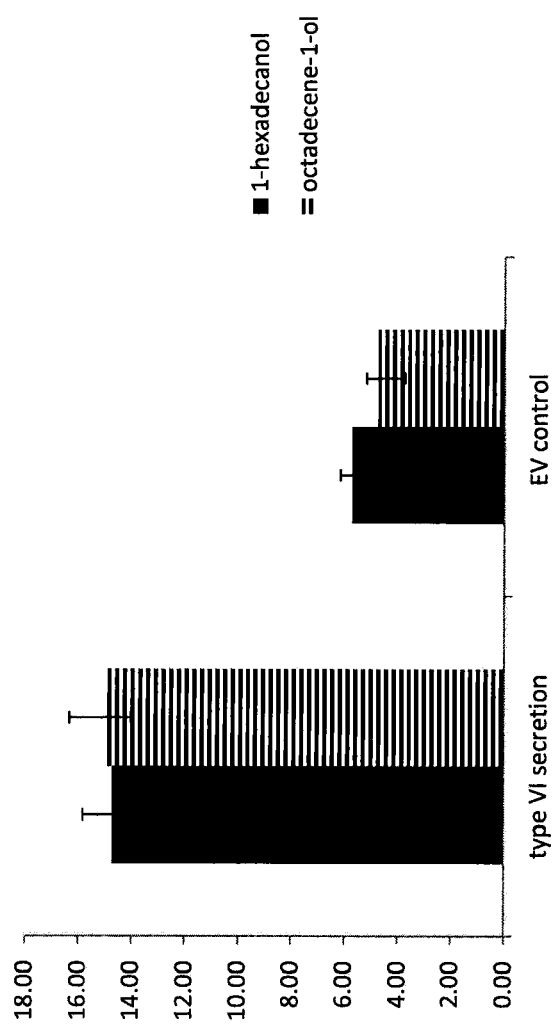
FIG. 19 is a graph showing the amount of C16 and C18 fatty alcohols secreted by the Maqu 2220-expressing *E. coli* strains that either lacked ("EV control") or contained ("Type VI secretion") the library insert depicted in FIG. 18.

The results of chemical analysis of the dodecane layer of the cultures demonstrated that expression of the genomic fragment that included the Type VI secretion system partial ORF in a strain expressing the Maqu 2220 alcohol-forming acyl-ACP reductase led to a substantial increase in the secretion of fatty alcohol when compared with a control strain expressing the Maqu 2220 reductase but lacking the genomic fragment that included the T6SS VgrG partial ORF. FIG. 19 provides a graph showing the amount of C16 and C18 fatty alcohols secreted by the Maqu 2220-expressing *E. coli* strains that either lacked or contained the T6SS genomic fragment including the truncated VgrG ORF.

Sequencing of the genomic fragment that led to higher levels of secreted fatty alcohols revealed an incomplete open reading frame (ORF) that encoded the major portion of the *Pseudomonas fluorescens* VgrG protein, a component of a Type VI Secretion System (T6SS) (Filloux et al. (2008) *Microbiology* 154: 1570-1583). This was surprising because T6SSs are associated with protein secretion, particularly in pathogenic bacteria, and even more surprising as the VgrG component is believed to be transported through the channel created by other components of the T6SS to reside at the external-most portion of the transport system, where it is believed to be responsible for puncturing the membranes of target cells, and, according to models, inserting into the cytoplasm of target cells. The C-terminal portion of the VgrG protein, not present in the genomic fragment expressed in the bacterial cells in the functional screen, is believed to interact with cytoplasmic components of the target cell.

Example 13

Figure 20:
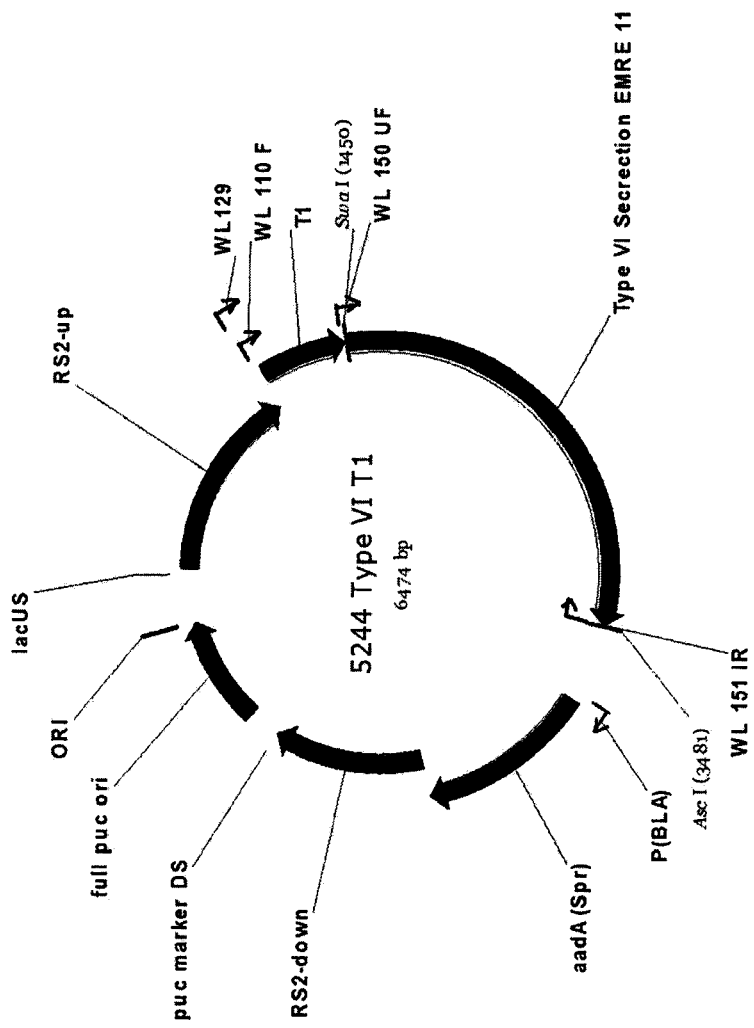
FIG. 20 is a schematic of the *Synechocystis* integration vector that the nrsB promoter operably linked to the PfVgrG gene.

Co-Expression of the PfVgrG Gene in *Synechocystis* Expressing a Non-Native Reductase Gene The full-length sequence of the *Pseudomonas fluorescens* VgrG protein (SEQ ID NO:38) was retrieved from a public database and used to synthesize a full-length gene encoding the VsgG polypeptide of SEQ ID NO:39. The PfVgrG gene was cloned in a *Synechocystis* integration vector that included RS2 up (SEQ ID NO:16) and RS2 down (SEQ ID NO:17) sequences for genome integration flanking the nrsB promoter operably linked to the PfVgrG gene, as well as an aadA gene for conferring spectinomycin resistance (FIG. 20). The construct was used to transform *Synechocystis* that included the Hch_05075 gene (SEQ ID NO:3) integrated into the RS1 site of the genome, along with a gene conferring kanamycin resistance (see Example 3). The VrgG gene was operably linked in the expression construct to the nickel-inducible nrsB promoter (SEQ ID NO:22).

The *Synechocystis* strain carrying the integrated Hch_05075 alcohol-forming acyl-ACP reductase gene (SEQ ID NO:3) was transformed with the PfVgrG gene (SEQ ID NO:38) also under the control of the nickel-inducible nrsB promoter (SEQ ID NO:22) as described in Example 3, above, except that after the 24 hour recovery period transformants were selected with chloramphenicol (20 μg/mL) and kanamycin (20 μg/mL). The presence of the Hch_05075 and Pf VgrG transgenes in selected transformants was confirmed by PCR.

To determine the effect of expression of the PfVgrG gene on fatty alcohol secretion, the strain containing the Hch_05075 gene (SEQ ID NO:3) and the nickel-inducible PfVgr gene (SEQ ID NO:38) were grown in triplicate 10 mL cultures in BG-11 media containing 25 uM nickel chloride in 20 mL glass scintillation vials. As a control, additional triplicate cultures of the strain containing the Hch_05075 gene (SEQ ID NO:3) and the nickel-inducible Pf VgrG gene (SEQ ID NO:38) were grown in 20 mL glass scintillation vials using 10 mL of BG-11 media that did not include nickel. The culture conditions were as provided in Example 4, except that 2 mLs of dodecane was overlayed on the top of the cultures for the last day (day 6-7) of the culture period. After seven days in culture, the dodecane layer was removed and submitted for chemical analysis.

To determine the amount of fatty alcohol secreted by the strains and recovered in the docecane layer, 0.5 mL of the dodecane layer was transferred to a 2.0 mL GC vial and 50 µL of internal standard (1 mg/mL 1-Pentadecanol in $CH_2Cl_2$) were added for a final concentration of internal standards of 100 µg/mL. The vials were then vortexed and analyzed by GC/MS-SCAN/SIM. The GC run conditions were as follows: 1.4 mL/min H2 with an oven temperature of 100° C. for 0.5 min, then ramped at 20° C./min to 270° C. and held for 1 min. The solvent delay was set at 4.3 min. A 1 µL injection was made on an inlet set at 280° C. utilizing a 3:1 split and containing a deactivated single gooseneck liner w/glass wool. The GC column was an Agilent HP-5MS, 30 m×0.25 mm×0.25 µm. The mass spectrometer scan range was set for m/z of 35-275, the SIM ions monitored were 55.0 and 41.0, and a 10 ms dwell time was used. Analytes were quantified via a 5-point calibration curve from 2-200 µg/mL.

The results of chemical analysis of the dodecane layer of the cultures shows that expression of the PfVgrG gene (SEQ ID NO:38) in *Synechocystis* that included a Hch_05075 acyl reductase gene led to a detectable secretion of fatty alcohol (FIG. 21) when compared with a control strain that also included the acyl reductase gene but did not express the Pf VgrG protein, which had undetectable levels of fatty alcohol in the dodecane layer.

Example 14

PfVgGr Expression for Fatty Acid Secretion in *Synechocystis*

The *Synechocystis* integration construct provided in Example 13 that included the PfVgrG gene (SEQ ID NO:38) operably linked to the nrsB promoter (SEQ ID NO:22) and the aadA gene was used to transform *Synechocystis* PCC 6803 that included the N-terminally truncated Cc1FatB1 gene (SEQ ID NO:23) operably linked to the IPTG-inducible TrcY promoter (SEQ ID NO:25) and integrated into the RS1 site of the genome, along with a gene conferring kanamycin resistance.

The *Synechocystis* strain carrying the integrated Cc1FatB1 gene (SEQ ID NO:23) was transformed with the Pf VgrG gene (SEQ ID NO:38) under the control of the nickel-inducible nrsB promoter (SEQ ID NO:22) as described in Example 3, above, except that after the 24 hour recovery period transformants were selected with chloramphenicol (20 µg/mL) and kanamycin (20 µg/mL). The presence of the Cc1FatB1 and Pf VgrG transgenes in selected transformants was confirmed by PCR.

To determine the effect of expression of the PfVgrG gene on fatty acid secretion, the strain containing the IPTG-inducible Cc1FatB1 gene (SEQ ID NO:23) and the nickel-inducible PfVgrG gene (SEQ ID NO:38) was grown in triplicate 10 mL cultures in BG-11 media in 20 mL glass scintillation vials. IPTG was added to a final concentration of 1 mM and nickel chloride was added to a final concentration of 25 uM for the last day of culturing (day 6-7). As a control, additional triplicate cultures of the strain containing the Cc1FatB1 gene (SEQ ID NO:23) and the nickel-inducible Pf VgrG gene (SEQ ID NO:38) were grown in 20 mL glass scintillation vials using 10 mL of BG-11 media that included IPTG but did not include nickel. The culture conditions were as provided in Example 4, except that 2 mLs of dodecane was overlayed on the top of the cultures at the outset of the culture period. After seven days in culture, the dodecane layer was removed and submitted for chemical analysis. Fatty acids were analyzed by gas chromatography as provided in Example 11.

Figure 22:
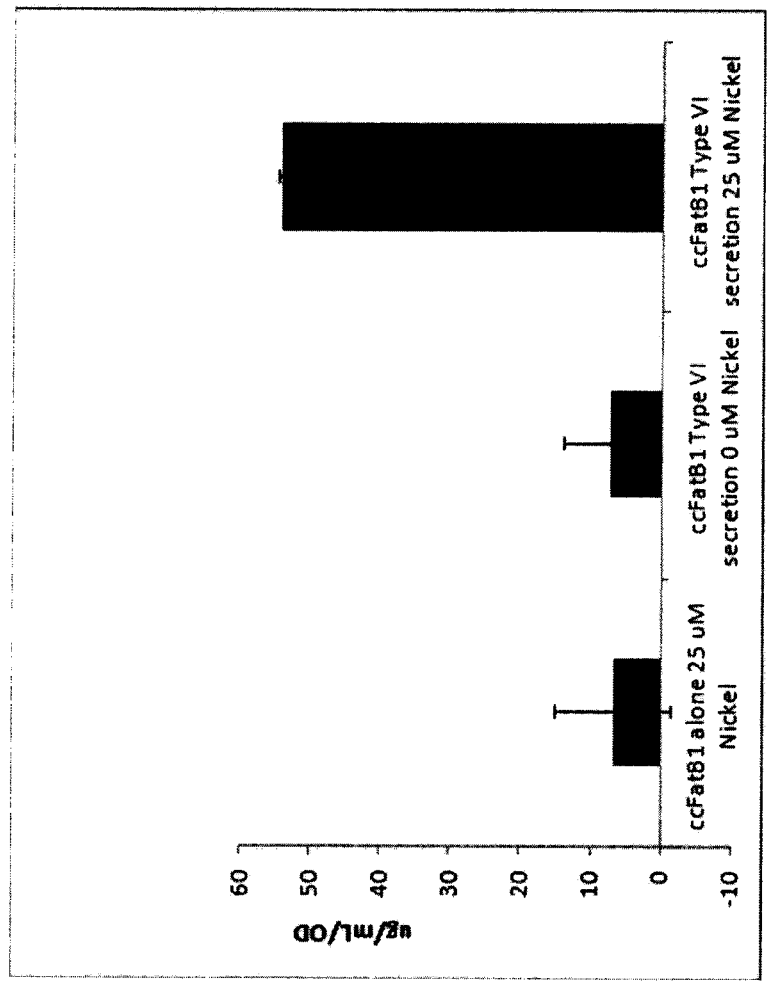
FIG. 22 is a graph showing the amount of fatty acids recovered from the dodecane layer of *Synechocystis* cultures containing cells expressing of the PfVgrG gene in addition to the Cc1FatB1 acyl-ACP thioesterase gene (right bar) as compared with *Synechocystis* cultures containing cells containing acyl-ACP thioesterase gene but not include the PfVgrG gene (left bar) and *Synechocystis* cultures containing cells containing acyl-ACP thioesterase gene but not induced to express the PfVgrG gene (middle bar).

The results of chemical analysis of the dodecane layer of the cultures shows that expression of the Pf VgrG gene in *Synechocystis* that expressed a thioesterase gene led to secretion of at least five-fold the amount of fatty acid secreted by a strain that did not express the PfVgrG gene (FIG. 22).

The invention claimed is:

1. A method of producing a fatty acid or fatty acid derivative, comprising:
providing a recombinant prokaryotic microorganism that comprises:
at least one non-native gene encoding a polypeptide that participates in the synthesis of a fatty acid or a fatty acid derivative; and
at least one non-native gene encoding a VgrG protein of a Type VI secretion system (T6SS) of a *Pseudomonas* or *Vibrio* species, or a C-terminally truncated VgrG protein comprising at least 620 amino acids of a VgrG protein of a T6SS of a *Pseudomonas* or *Vibrio* species; and
culturing the recombinant prokaryotic microorganism for a period of time in a suitable culture medium;
wherein the recombinant prokaryotic microorganism secretes a greater amount of a free fatty acid or fatty acid derivative than the amount produced by a control prokaryotic microorganism substantially identical to the recombinant prokaryotic microorganism except that the control prokaryotic microorganism does not express a non-native gene encoding a VgrG protein of a T6SS of a *Pseudomonas* or *Vibrio* species or a C-terminally truncated VgrG protein comprising at least 620 amino acids of a VgrG protein of a T6SS of a *Pseudomonas* or *Vibrio* species.

2. The method of claim 1, wherein the VgrG protein is a VgrG protein of a *Psuedomonas* or *Vibrio* species.

3. The method of claim 2, wherein the VgrG protein is a VgrG protein of a T6SS of a *Pseudomonas* species.

4. The method of claim 1, wherein the fatty acid or fatty acid derivative is a free fatty acid.

5. The method of claim 1, wherein the fatty acid or fatty acid derivative is a fatty acid derivative.

6. The method of claim 5, wherein the fatty acid derivative is selected from the group consisting of a fatty aldehyde, a fatty alcohol, a fatty acid ester, a wax ester, an alkane, and an alkene.

7. The method of claim 6, wherein the fatty acid derivative is a fatty aldehyde or fatty alcohol.

8. The method of claim 7, wherein the fatty acid derivative is a fatty alcohol.

9. The method of claim 1, further comprising recovering the fatty acid or fatty acid derivative from the culture.

10. The method of claim 9, wherein said recovering comprises adding an organic solvent to the culture medium, allowing the culture to incubate for an additional period of time, and removing the organic solvent to recover the fatty acid or fatty acid derivative.

11. The method of claim 10, wherein the organic solvent comprises an alkane, an alkene, or a fatty alcohol.

12. The method of claim 10, wherein the culture is viable after removal of the organic solvent, further wherein the recombinant microorganism is cultured further after removal of the organic solvent.

13. The method of claim 10, wherein culturing of the recombinant microorganism for a period of time, addition of an organic solvent to the culture medium for an additional period of time, and removing the organic solvent to recover a free fatty acid or fatty acid product is performed two or more times.

14. The method of claim 1, wherein the polypeptide that participates in the production of a fatty acid or a fatty acid derivative is an acyl-ACP thioesterase, an acyl-CoA thioesterase, an acyl-CoA synthetase, an acyl-CoA reductase, an acyl-ACP reductase, a decarbonylase, a decarboxylase, or a wax synthase.

15. The method of claim 1, wherein the prokaryotic microorganism is a cyanobacterium.

16. The method of claim 15, wherein said culture conditions are photoautotrophic.

17. The method of claim 1, wherein the recombinant prokaryotic microorganism comprises at least one non-native gene encoding a C-terminally truncated VgrG protein comprising at least 620 amino acids of a VgrG protein of a T6SS of a *Pseudomonas* or *Vibrio* species.

18. The method of claim 1, wherein the prokaryotic microorganism is a bacterial species selected from the group consisting of an *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Shewanella, Stenotrophomonas, Streptomyces, Streptococcus, Vibrio,* and *Zymomonas* species.

19. The method of claim 18, wherein the prokaryotic microorganism is *Escherichia coli*.

20. A method of producing a fatty acid or fatty acid derivative, comprising:
providing a recombinant prokaryotic microorganism that comprises:
a non-native gene encoding a polypeptide that participates in the synthesis of a fatty acid or a fatty acid derivative; and a non-native gene encoding a polypeptide comprising an amino acid sequence having at least 95% identity to a VgrG protein sequence selected from the group consisting of SEQ ID NO:37, SEQ ID NO:39, and SEQ ID NO:40; and
culturing the recombinant prokaryotic microorganism for a period of time in a suitable culture medium;
wherein the recombinant prokaryotic microorganism secretes a greater amount of a free fatty acid or fatty acid derivative than the amount produced by a control prokaryotic microorganism substantially identical to the recombinant prokaryotic microorganism except that the control prokaryotic microorganism does not express a non-native gene encoding a polypeptide comprising an amino acid sequence having at least 95% identity to a sequence selected from the group consisting of SEQ ID NO:37, SEQ ID NO:39, and SEQ ID NO:40.

21. The method of claim 20, wherein the non-native gene encodes a polypeptide comprising an amino acid sequence having at least 95% identity to SEQ ID NO:37 or SEQ ID NO:39.

22. The method of claim 20, wherein the prokaryotic microorganism is a bacterium.

23. The method of claim 22, wherein the prokaryotic microorganism is a bacterial species selected from the group consisting of an *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Shewanella, Stenotrophomonas, Streptomyces, Streptococcus, Vibrio,* and *Zymomonas* species.

24. The method of claim 20, wherein the prokaryotic microorganism is a cyanobacterium.

25. The method of claim 24, wherein said culture conditions are photoautotrophic.

26. The method of claim 20, wherein the non-native gene encodes a polypeptide comprising an amino acid sequence having at least 95% identity to a sequence selected from the group consisting of SEQ ID NO:37, SEQ ID NO:39, and SEQ ID NO:40.

27. The method of claim 20, wherein the fatty acid derivative is selected from the group consisting of a fatty aldehyde, a fatty alcohol, a fatty acid ester, a wax ester, an alkane, and an alkene.

28. The method of claim 27, wherein the fatty acid derivative is a fatty aldehyde or fatty alcohol.

29. The method of claim 20, further comprising recovering the fatty acid or fatty acid derivative from the culture.

30. The method of claim 29, wherein said recovering comprises adding an organic solvent to the culture medium, allowing the culture to incubate for an additional period of time, and removing the organic solvent to recover the fatty acid or fatty acid derivative.

\* \* \* \* \*

SEQUENCE LISTING

<160> NUMBER OF SEQ ID NOS: 40

<210> SEQ ID NO 1
<211> LENGTH: 1542
<212> TYPE: DNA
<213> ORGANISM: Marinobacter aquaeoli VT8
<220> FEATURE:
<221> NAME/KEY: misc_feature
<223> OTHER INFORMATION: "Maqu_2220" reductase

<400> SEQUENCE: 1
atggcaatac agcaggtaca tcacgctgac acttcatcat caaaggtgct cggacagctc        60
cgtggcaagc gggttctgat caccggtacc actggctttc tgggcaaggt ggtcctcgaa       120
aggctgattc gggcggtgcc tgatatcggc gcaatttacc tgctgatccg gggcaataaa       180
cggcatccgg atgctcgttc ccgtttcctg gaagaaattg ccacctcctc ggtgtttgac       240
cgtcttcgcg aggccgattc agaggggatt gacgcctttc tggaagagcg cattcactgc       300
gtgaccggtg aggtgaccga gcgggtttc gggatagggc aggaagacta tcgcaaactc       360

```
gccaccgaac tggatgcggt gatcaactcc gctgcaagcg tgaatttccg tgaagagctc      420
gacaaggcgc tggccatcaa caccctgtgc cttcggaata ttgccggcat ggtggatttg      480
aatccgaagc ttgcggtcct gcaggtctcc acctgctatg tcaatggcat gaactcgggg      540
caggtaaccg aatcggtgat caagccggca ggcgaggccg tgccgcgttc cccggacggc      600
ttctatgaga tagaagagct tgttcgcctg cttcaggata aaattgaaga cgttcaggcc      660
cgttattccg gcaaagtgct ggagaggaag ctggtggacc tggggattcg ggaagccaac      720
cgctatggct ggagcgatac ctacaccttt accaagtggc tgggcgaaca gttgctgatg      780
aaggcgttaa cgggcgcac gctgaccatt ctgcgtcctt cgattatcga agtgccctg       840 gaggaaccag cgcccggctg gattgagggg gtgaaggtgg cagatgccat catcctggct      900
tacgcacggg aaaaagtcac cctcttcccg ggcaaacgct ccgtatcat cgatgtgatt      960 ccagtggacc tggtggccaa ctccatcatc ctttccctgg cggaagctct tggagaaccc     1020
ggtcgacgtc gcatctatca atgttgcagc ggggcggca atccaatctc cctgggtgag     1080
ttcatcgatc atctcatggc ggaatcaaaa gccaattacg ctgcctacga tcacctgttc     1140
taccggcagc ccagcaagcc gtttctggcg gttaaccggg cgctgtttga tttggtgatc     1200
agtggtgttc gcttaccgct ctccctgacg gaccgtgtgc tcaaattact gggaaattcc     1260
cgggacctga aatgctcag gaatctggat accaccagt cgctggcaac catttttggt     1320
ttctacaccg cgccggatta tatcttccgg aacgatgagc tgatggcgct ggcgaaccgg     1380
atgggtgagg tcgataaagg gctgttcccg gtggatgccc gcctgattga ctgggagctc     1440
tacctgcgca agattcacct ggccgggctc aatcgctatg ccctgaaaga acgaaaggtg     1500
tacagtctga aaaccgcgcg ccagcgcaaa aaagctgcct ga                         1542
```

<210> SEQ ID NO 2
<211> LENGTH: 513
<212> TYPE: PRT
<213> ORGANISM: Marinobacter aquaeoli VT8
<220> FEATURE:
<221> NAME/KEY: MISC_FEATURE
<223> OTHER INFORMATION: "Maqu_2220" reductase

<400> SEQUENCE: 2

```
Met Ala Ile Gln Gln Val His His Ala Asp Thr Ser Ser Ser Lys Val
 1               5                  10                  15

Leu Gly Gln Leu Arg Gly Lys Arg Val Leu Ile Thr Gly Thr Thr Gly
                20                  25                  30

Phe Leu Gly Lys Val Val Leu Glu Arg Leu Ile Arg Ala Val Pro Asp
            35                  40                  45

Ile Gly Ala Ile Tyr Leu Leu Ile Arg Gly Asn Lys Arg His Pro Asp
        50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95

Arg Ile His Cys Val Thr Gly Glu Val Thr Glu Ala Gly Phe Gly Ile
            100                 105                 110

Gly Gln Glu Asp Tyr Arg Lys Leu Ala Thr Glu Leu Asp Ala Val Ile
        115                 120                 125

Asn Ser Ala Ala Ser Val Asn Phe Arg Glu Glu Leu Asp Lys Ala Leu
    130                 135                 140
```

```
Ala Ile Asn Thr Leu Cys Leu Arg Asn Ile Ala Gly Met Val Asp Leu
145                 150                 155                 160

Asn Pro Lys Leu Ala Val Leu Gln Val Ser Thr Cys Tyr Val Asn Gly
            165                 170                 175

Met Asn Ser Gly Gln Val Thr Glu Ser Val Ile Lys Pro Ala Gly Glu
        180                 185                 190

Ala Val Pro Arg Ser Pro Asp Gly Phe Tyr Glu Ile Glu Glu Leu Val
    195                 200                 205

Arg Leu Leu Gln Asp Lys Ile Glu Asp Val Gln Ala Arg Tyr Ser Gly
210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
            260                 265                 270

Pro Ser Ile Ile Glu Ser Ala Leu Glu Glu Pro Ala Pro Gly Trp Ile
        275                 280                 285

Glu Gly Val Lys Val Ala Asp Ala Ile Ile Leu Ala Tyr Ala Arg Glu
    290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Leu Ser Leu Ala Glu Ala
                325                 330                 335

Leu Gly Glu Pro Gly Arg Arg Arg Ile Tyr Gln Cys Cys Ser Gly Gly
                340                 345                 350

Gly Asn Pro Ile Ser Leu Gly Glu Phe Ile Asp His Leu Met Ala Glu
            355                 360                 365

Ser Lys Ala Asn Tyr Ala Ala Tyr Asp His Leu Phe Tyr Arg Gln Pro
        370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
                405                 410                 415

Leu Gly Asn Ser Arg Asp Leu Lys Met Leu Arg Asn Leu Asp Thr Thr
            420                 425                 430

Gln Ser Leu Ala Thr Ile Phe Gly Phe Tyr Thr Ala Pro Asp Tyr Ile
        435                 440                 445

Phe Arg Asn Asp Glu Leu Met Ala Leu Ala Asn Arg Met Gly Glu Val
450                 455                 460

Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
                485                 490                 495

Glu Arg Lys Val Tyr Ser Leu Lys Thr Ala Arg Gln Arg Lys Lys Ala
            500                 505                 510

Ala
```

<210> SEQ ID NO 3
<211> LENGTH: 1518
<212> TYPE: DNA
<213> ORGANISM: Hahella chejuensis
<220> FEATURE:
<221> NAME/KEY: misc_feature
<223> OTHER INFORMATION: "Hch_05075" reductase

<400> SEQUENCE: 3

```
atgaagcaat cacttacgtt aactgctttt gctaataaga atgtactgat tacggggacg      60
acgggattcg tcggcaaggt ggtactggag aagctgctgc gcagcgtgcc gacaattggg     120
aagatttatt tgctgatacg gggtaattca agaaccctac agcgcgaaa gcggttccag      180
aatgagatcg cgacctcatc tatttttcgat actctcaagg catcgcaggg aagtcgtttc    240
gaggagttgt gcgaaacccg catccactgc gtgaccggag aggtgacgga gcctctgttt     300
ggcctgtcgg agaaggactt taccgacctg ccgcagata tcgacgttat tatcaattca      360
gccgccagcg tcaatttccg cgaagcgctg atcaggctc tcaccatcaa taccctgtgc      420
cttaaaaata tcattgaact gtcgcggcgc gcggcggact gccctgtcgt gcaggtatcc     480
acctgctacg tcaacggctt caatcaggga gtgatgaag aggaaatcgt cagcccggcg      540
ggagaacgca ttgagcgttc agaacgcggc tactatgaag ttgagccgct gattgcgcgt     600
ttgctgcagg atgtagagca agtgtccgcc gctgcggcgg atgatcatag cagggaaaag    660
gatcttatcg acctgggtat caagaagcc aataagtatg ttggaacga tacctatacc      720
ttcactaaat ggatgggcga gcagttgctg atgaaggagc tgtatggcaa aaccctgacc    780
atcctgcgac cttccattgt tgaaagtacg ctgctgggac cggcgccggg ctggattgag    840
ggggtgaaag tggcggatgc gatcatcctc gcttacgcca gagaaaaggt gtctttgttt    900
cccggcaaga agaatgcggt cattgatatc attccggcgg acctggtggc caacagcatc    960
atcctgagcg ccacggaagc gctgctggat tccggcgccc atcgcatcta ccagtgttgc   1020
agcagcgagg ttaatccaat caggattcgg gaagtcattg gcatgtgca gcaagaggcg   1080
gagcacaatt atcagacgca cgacaaactg ttctaccgca agccgaagaa gcccttgta   1140
atgattcccg cgccgtgtt tcacgcgttg atggcgatca gtttccacat gctgaaatgg   1200
agttcccgtc tgcagagctt gtttggccgt aaggcttccg ggcgcaagct gagcaacatg   1260
gaaactacga tgaaactgtc caaggtgttt tccttctata cctctcccag ctataccttc   1320
agcaaccgcc gtctgcagga gctatccacc cgtcttgggg aatatgacca gagcgaattc   1380
cccgtgaatg cgggtatgta tgactgggcg cactacttgc gggaagttca cgtggcgggt   1440
ctgaacaagt acgcgctgcg gccgaaagtg gtgaagatga acccgcctgc agcaaaacct   1500
cgcagccgcg ctgcgtaa                                                  1518
```

<210> SEQ ID NO 4
<211> LENGTH: 505
<212> TYPE: PRT
<213> ORGANISM: Hahella chejuensis
<220> FEATURE:
<221> NAME/KEY: MISC_FEATURE
<223> OTHER INFORMATION: "Hch_05075" reductase

<400> SEQUENCE: 4

```
Met Lys Gln Ser Leu Thr Leu Thr Ala Phe Ala Asn Lys Asn Val Leu
1               5                   10                  15

Ile Thr Gly Thr Thr Gly Phe Val Gly Lys Val Val Leu Glu Lys Leu
            20                  25                  30

Leu Arg Ser Val Pro Thr Ile Gly Lys Ile Tyr Leu Leu Ile Arg Gly
        35                  40                  45

Asn Ser Lys Asn Pro Thr Ala Arg Lys Arg Phe Gln Asn Glu Ile Ala
    50                  55                  60

Thr Ser Ser Ile Phe Asp Thr Leu Lys Ala Ser Gln Gly Ser Arg Phe
```

```
            65                  70                  75                  80
Glu Glu Leu Cys Glu Thr Arg Ile His Cys Val Thr Gly Glu Val Thr
                    85                  90                  95

Glu Pro Leu Phe Gly Leu Ser Glu Lys Asp Phe Thr Asp Leu Ala Ala
                100                 105                 110

Asp Ile Asp Val Ile Ile Asn Ser Ala Ala Ser Val Asn Phe Arg Glu
                115                 120                 125

Ala Leu Asp Gln Ala Leu Thr Ile Asn Thr Leu Cys Leu Lys Asn Ile
            130                 135                 140

Ile Glu Leu Ser Arg Arg Ala Ala Asp Cys Pro Val Gln Val Ser
145                 150                 155                 160

Thr Cys Tyr Val Asn Gly Phe Asn Gln Gly Val Met Glu Glu Ile
                165                 170                 175

Val Ser Pro Ala Gly Glu Arg Ile Glu Arg Ser Glu Arg Gly Tyr Tyr
                180                 185                 190

Glu Val Glu Pro Leu Ile Ala Arg Leu Leu Gln Asp Val Glu Gln Val
                195                 200                 205

Ser Ala Ala Ala Asp Asp His Ser Arg Glu Lys Asp Leu Ile Asp
    210                 215                 220

Leu Gly Ile Lys Glu Ala Asn Lys Tyr Gly Trp Asn Asp Thr Tyr Thr
225                 230                 235                 240

Phe Thr Lys Trp Met Gly Glu Gln Leu Leu Met Lys Glu Leu Tyr Gly
                245                 250                 255

Lys Thr Leu Thr Ile Leu Arg Pro Ser Ile Val Glu Ser Thr Leu Leu
                260                 265                 270

Gly Pro Ala Pro Gly Trp Ile Glu Gly Val Lys Val Ala Asp Ala Ile
            275                 280                 285

Ile Leu Ala Tyr Ala Arg Glu Lys Val Ser Leu Phe Pro Gly Lys Lys
            290                 295                 300

Asn Ala Val Ile Asp Ile Ile Pro Ala Asp Leu Val Ala Asn Ser Ile
305                 310                 315                 320

Ile Leu Ser Ala Thr Glu Ala Leu Leu Asp Ser Gly Ala His Arg Ile
                325                 330                 335

Tyr Gln Cys Cys Ser Ser Glu Val Asn Pro Ile Arg Ile Arg Glu Val
                340                 345                 350

Ile Gly His Val Gln Gln Glu Ala Glu His Asn Tyr Gln Thr His Asp
            355                 360                 365

Lys Leu Phe Tyr Arg Lys Pro Lys Lys Pro Phe Val Met Ile Pro Gly
            370                 375                 380

Ala Val Phe His Ala Leu Met Ala Ile Ser Phe His Met Leu Lys Trp
385                 390                 395                 400

Ser Ser Arg Leu Gln Ser Leu Phe Gly Lys Ala Ser Gly Arg Lys
                405                 410                 415

Leu Ser Asn Met Glu Thr Thr Met Lys Leu Ser Lys Val Phe Ser Phe
                420                 425                 430

Tyr Thr Ser Pro Ser Tyr Thr Phe Ser Asn Arg Arg Leu Gln Glu Leu
            435                 440                 445

Ser Thr Arg Leu Gly Glu Tyr Asp Gln Ser Glu Phe Pro Val Asn Ala
            450                 455                 460

Gly Met Tyr Asp Trp Ala His Tyr Leu Arg Glu Val His Val Ala Gly
465                 470                 475                 480

Leu Asn Lys Tyr Ala Leu Arg Pro Lys Val Val Lys Met Asn Pro Pro
                485                 490                 495
```

Ala Ala Lys Pro Arg Ser Arg Ala Ala
        500                 505

<210> SEQ ID NO 5
<211> LENGTH: 1539
<212> TYPE: DNA
<213> ORGANISM: Marinobacter algicola DG893
<220> FEATURE:
<221> NAME/KEY: misc_feature
<223> OTHER INFORMATION: "MDG893_11561" reductase

<400> SEQUENCE: 5

```
atggcaacac agcagcaaca aaacggagcg tcagcgtccg gtgttcttga gcaactacgt      60
ggtaaacacg tgctgatcac cggcaccacc gggtttcttg gtaaggtggt actggaaaaa     120
ttgattcgca cggtgccgga tattggcggg atccatcttc ttatccgtgg taacaaaagg     180
catcctgcag cacgggaacg attcctcaac gagatcgcca gttcttccgt gttcgaacgc     240
cttcggcacg atgacaacga ggcgtttgaa acctttcttg aggaacgcgt tcactgcatc     300
accggcgaag tgacagagtc gcgtttcggg ctcacgccgg agcggttccg tgcacttgcc     360
gggcaggtcg atgcgtttat aaattccgca gccagtgtga acttccggga ggaactcgac     420
aaggcgctga agattaacac cctgtgcctg agaacgttgc cgctctggc ggagctcaat      480
agcgccatgg cggttatcca ggtgtccacc tgctacgtca atggcaagaa ttccggccag     540
atcacggagt ccgtcatcaa gccggcgggc gagtctattc cccgcagcac cgacggctac     600
tatgaaatcg aagagcttgt gcatttgctg caggacaaaa tttccgacgt gaaagcccga     660
tactccggca agtacttga aaaaagctg gtggacctgg ggattcgaga ggccaacaac       720
tacggctgga gtgacaccta cacgtttacc aaatggctgg gtgagcaact cctgatgaaa     780
gcccttttccg ggcgttcact tacgattgtt cgccttcca tcattgaaag tgcactggaa     840
gagccttcgc caggatggat tgaaggtgtg aaggtggcag acgccattat ccttgcctat     900
gcccgtgaga aggtctccct gttcccaggc aagcgtagcg gcattatcga tgtgatcccg     960
gtggacctgg tggccaacag tatcatcttg tccctggcag aagccctttc cgggtcaggg    1020
cagcgccgca tctatcaatg ctgcagtggc ggttctaatc cgatttcgct gggcaagttc    1080
attgactacc tgatggccga agccaagacc aactatgcag cgtatgacca gttgttctac    1140
cgacggccca cgaaaccgtt tgtggcggtc aatcgcaagc tgtttgatgt tgtggttggc    1200
ggcatgcgcg tgccgttgtc gattgctggc aaggcaatga ggctggctgg ccagaaccgt    1260
gagctcaagg ttctcaaaaa cctcgatacc acgcgttcac tggccaccat ctttggtttc    1320
tacacggcac cggattacat cttccgtaac gattcgctga tggccctggc ttcgcgcatg    1380
ggtgaactgg accgtgtcct gttcccggtg gatgcgcgtc agattgactg gcagctgtac    1440
ttgtgcaaga tccacctggg aggtctcaac cgctacgctc tgaaggagcg aaaactgtac    1500
agcctgcggg ccgccgacac ccgcaaaaaa gccgcctga                            1539
```

<210> SEQ ID NO 6
<211> LENGTH: 512
<212> TYPE: PRT
<213> ORGANISM: Marinobacter algicola DG893
<220> FEATURE:
<221> NAME/KEY: MISC_FEATURE
<223> OTHER INFORMATION: "MDG893_11561" reductase

<400> SEQUENCE: 6

Met Ala Thr Gln Gln Gln Gln Asn Gly Ala Ser Ala Ser Gly Val Leu

-continued

```
1               5                   10                  15
Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
                35                  40                  45

Gly Gly Ile His Leu Leu Ile Arg Gly Asn Lys Arg His Pro Ala Ala
                50                  55                  60

Arg Glu Arg Phe Leu Asn Glu Ile Ala Ser Ser Val Phe Glu Arg
65                      70                  75                  80

Leu Arg His Asp Asp Asn Glu Ala Phe Glu Thr Phe Leu Glu Arg
                    85                  90                  95

Val His Cys Ile Thr Gly Glu Val Thr Glu Ser Arg Phe Gly Leu Thr
                    100                 105                 110

Pro Glu Arg Phe Arg Ala Leu Ala Gly Gln Val Asp Ala Phe Ile Asn
                    115                 120                 125

Ser Ala Ala Ser Val Asn Phe Arg Glu Glu Leu Asp Lys Ala Leu Lys
                130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                    165                 170                 175

Asn Ser Gly Gln Ile Thr Glu Ser Val Ile Lys Pro Ala Gly Glu Ser
                180                 185                 190

Ile Pro Arg Ser Thr Asp Gly Tyr Tyr Glu Ile Glu Glu Leu Val His
                195                 200                 205

Leu Leu Gln Asp Lys Ile Ser Asp Val Lys Ala Arg Tyr Ser Gly Lys
                210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                    245                 250                 255

Leu Leu Met Lys Ala Leu Ser Gly Arg Ser Leu Thr Ile Val Arg Pro
                260                 265                 270

Ser Ile Ile Glu Ser Ala Leu Glu Glu Pro Ser Pro Gly Trp Ile Glu
                275                 280                 285

Gly Val Lys Val Ala Asp Ala Ile Ile Leu Ala Tyr Ala Arg Glu Lys
                290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                    325                 330                 335

Ser Gly Ser Gly Gln Arg Arg Ile Tyr Gln Cys Cys Ser Gly Gly Ser
                340                 345                 350

Asn Pro Ile Ser Leu Gly Lys Phe Ile Asp Tyr Leu Met Ala Glu Ala
                355                 360                 365

Lys Thr Asn Tyr Ala Ala Tyr Asp Gln Leu Phe Tyr Arg Arg Pro Thr
                370                 375                 380

Lys Pro Phe Val Ala Val Asn Arg Lys Leu Phe Asp Val Val Gly
385                 390                 395                 400

Gly Met Arg Val Pro Leu Ser Ile Ala Gly Lys Ala Met Arg Leu Ala
                    405                 410                 415

Gly Gln Asn Arg Glu Leu Lys Val Leu Lys Asn Leu Asp Thr Thr Arg
                420                 425                 430
```

```
Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
        450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
                500                 505                 510

<210> SEQ ID NO 7
<211> LENGTH: 1536
<212> TYPE: DNA
<213> ORGANISM: Marinobacter adhaerens HP15
<220> FEATURE:
<221> NAME/KEY: misc_feature
<223> OTHER INFORMATION: "HP15_810" reductase

<400> SEQUENCE: 7
atggcaacac agcagctgaa tcccgatgca tcatcaaaag tacttgagcg gctccggggc      60
aagcacgttc tgattaccgg caccacgggc tttctcggca aggtggttct ggaaaagctc     120
attcgcgccg ttccggacat aggcggcatt catctgctga tccgtggaaa caaacgtcac     180
cccgatgcgc gggatcgttt ttttgaggag atcgccacgt cgtcagtctt cgatcgtctg     240
cgccaggacg ataacgaggc ttttgaaacc ttcattgaag atcgtgtgca ttgcgtaacc     300
ggggaagtga ccgagccttt gtttggtctg tccgctgacc gtttccgcaa gctggctggc     360
ggcatcgatg tggttgtcaa ctccgcagcc agtgtgaact ccgggaaga gcttgataaa     420
gcgcttgcca tcaatacccg ttgcctcgac aacgtggccg agcttgcgcg acagaacaag     480
tcgctggcgg tgctgcaggt ttccacctgc tatgtaaacg gcatgaattc cggacagatc     540
acggagaccg tgatcaagcc ggcaggtgag gccatacccc ggagcactga aggttactat     600
gagatcgaag aacttgtccg gctgctggag gacaagatag cggacgtgcg ttcccgctac     660
tccggcaagg cactggaaaa gaagctggtg gaccttggca tccgtgaagc caaccattat     720
ggctggagcg ataccctatac ctttaccaaa tggctcggtg agcaactcct gctcaaggcc     780
ctgtccgggc gggcactgac cattgtgcgc ccatccatta ttgaaagtgc actcgaggaa     840
cccgcgccag gctggattga aggtgtgaag gtggcggatg ccattatcct tgcgtatgcc     900
cgcgagaagg tcacgctctt ccctggcaaa cgcgctggcg tcatcgatgt tattcccgtg     960
gatctggtgg ccaatgccat catcctggcg gcggctgaag ccgttgctga ttcgccacgt    1020
caccggattt accagtgttg cagtggcagc tccaacccgg tttctctcgg cagtttatt    1080
gaccacctca tggcggaatc aaaagccaac ttcgccgaat acgatcagct gttctaccga    1140
cagccgacca aacccttcat tgcagtcaac cgccggctgt tcgatgccgt cgtaggcggg    1200
gtgcgcattc cactgagcat taccgggaag gttttgcgca tgctgggcca aaatcgcgag    1260
ttgaaagtgc tccggaatct ggacacgaca cgctcgctgg cgaccatttt cggtttctac    1320
accgcgccag actatatctt ccggaatgat gatctgctgg ccctggcatc gaggatgggt    1380
gagctggaca aggtgctgtt cccggtagat gcccgccaga ttgactggtc ggtctatctg    1440
cgcaagatcc acctggcagg cctgaaccga tacgccctca aggagcgcaa ggtatacagc    1500
ctgcgctctg ccaaggcccg aaaaaaggca gcgtga                             1536
```

<210> SEQ ID NO 8
<211> LENGTH: 511
<212> TYPE: PRT
<213> ORGANISM: Marinobacter adhaerens HP15
<220> FEATURE:
<221> NAME/KEY: MISC_FEATURE
<223> OTHER INFORMATION: "HP15_810" reductase

<400> SEQUENCE: 8

```
Met Ala Thr Gln Gln Leu Asn Pro Asp Ala Ser Ser Lys Val Leu Glu
1               5                   10                  15

Arg Leu Arg Gly Lys His Val Leu Ile Thr Gly Thr Thr Gly Phe Leu
            20                  25                  30

Gly Lys Val Val Leu Glu Lys Leu Ile Arg Ala Val Pro Asp Ile Gly
        35                  40                  45

Gly Ile His Leu Leu Ile Arg Gly Asn Lys Arg His Pro Asp Ala Arg
    50                  55                  60

Asp Arg Phe Phe Glu Glu Ile Ala Thr Ser Ser Val Phe Asp Arg Leu
65                  70                  75                  80

Arg Gln Asp Asp Asn Glu Ala Phe Glu Thr Phe Ile Glu Asp Arg Val
                85                  90                  95

His Cys Val Thr Gly Glu Val Thr Glu Pro Leu Phe Gly Leu Ser Ala
            100                 105                 110

Asp Arg Phe Arg Lys Leu Ala Gly Gly Ile Asp Val Val Val Asn Ser
        115                 120                 125

Ala Ala Ser Val Asn Phe Arg Glu Glu Leu Asp Lys Ala Leu Ala Ile
    130                 135                 140

Asn Thr Arg Cys Leu Asp Asn Val Ala Glu Leu Ala Arg Gln Asn Lys
145                 150                 155                 160

Ser Leu Ala Val Leu Gln Val Ser Thr Cys Tyr Val Asn Gly Met Asn
                165                 170                 175

Ser Gly Gln Ile Thr Glu Thr Val Ile Lys Pro Ala Gly Glu Ala Ile
            180                 185                 190

Pro Arg Ser Thr Glu Gly Tyr Tyr Glu Ile Glu Glu Leu Val Arg Leu
        195                 200                 205

Leu Glu Asp Lys Ile Ala Asp Val Arg Ser Arg Tyr Ser Gly Lys Ala
    210                 215                 220

Leu Glu Lys Lys Leu Val Asp Leu Gly Ile Arg Glu Ala Asn His Tyr
225                 230                 235                 240

Gly Trp Ser Asp Thr Tyr Thr Phe Thr Lys Trp Leu Gly Glu Gln Leu
                245                 250                 255

Leu Leu Lys Ala Leu Ser Gly Arg Ala Leu Thr Ile Val Arg Pro Ser
            260                 265                 270

Ile Ile Glu Ser Ala Leu Glu Glu Pro Ala Pro Gly Trp Ile Glu Gly
        275                 280                 285

Val Lys Val Ala Asp Ala Ile Ile Leu Ala Tyr Ala Arg Glu Lys Val
    290                 295                 300

Thr Leu Phe Pro Gly Lys Arg Ala Gly Val Ile Asp Val Ile Pro Val
305                 310                 315                 320

Asp Leu Val Ala Asn Ala Ile Ile Leu Ala Ala Glu Ala Val Ala
                325                 330                 335

Asp Ser Pro Arg His Arg Ile Tyr Gln Cys Cys Ser Gly Ser Ser Asn
            340                 345                 350

Pro Val Ser Leu Gly Gln Phe Ile Asp His Leu Met Ala Glu Ser Lys
        355                 360                 365
```

```
Ala Asn Phe Ala Glu Tyr Asp Gln Leu Phe Tyr Arg Gln Pro Thr Lys
    370                 375                 380

Pro Phe Ile Ala Val Asn Arg Arg Leu Phe Asp Ala Val Val Gly Gly
385                 390                 395                 400

Val Arg Ile Pro Leu Ser Ile Thr Gly Lys Val Leu Arg Met Leu Gly
            405                 410                 415

Gln Asn Arg Glu Leu Lys Val Leu Arg Asn Leu Asp Thr Thr Arg Ser
        420                 425                 430

Leu Ala Thr Ile Phe Gly Phe Tyr Thr Ala Pro Asp Tyr Ile Phe Arg
        435                 440                 445

Asn Asp Asp Leu Leu Ala Leu Ala Ser Arg Met Gly Glu Leu Asp Lys
        450                 455                 460

Val Leu Phe Pro Val Asp Ala Arg Gln Ile Asp Trp Ser Val Tyr Leu
465                 470                 475                 480

Arg Lys Ile His Leu Ala Gly Leu Asn Arg Tyr Ala Leu Lys Glu Arg
            485                 490                 495

Lys Val Tyr Ser Leu Arg Ser Ala Lys Ala Arg Lys Lys Ala Ala
        500                 505                 510

<210> SEQ ID NO 9
<211> LENGTH: 1545
<212> TYPE: DNA
<213> ORGANISM: Oceanobacter sp. RED65
<220> FEATURE:
<221> NAME/KEY: misc_feature
<223> OTHER INFORMATION: "RED65_09894" reductase

<400> SEQUENCE: 9
atgagtcagt attctgcatt ttcagtgtct cagtctctca aaggtaagca catcttttta     60
acgggtgtga caggtttttt aggcaaagct attttagaaa agctcttgta cagtgtaccg    120
cagctagcac aaatccacat tttggtgcgc ggtggcaaag tttcagccaa aaagcgtttt    180
caacacgata tcctcggctc cagtattttt gagcgcctga agagcagca tggcgagcac     240 tttgaagaat gggtgcaatc aaaaatcaat ctggtggaag gtgaattgac acaacccatg    300
tttgatttgc ctagtgctga atttgcgggt ttggccaatc aactggactt aattattaac    360
tccgctgcca gtgttaattt ccgcgaaaac cttgagaaag cgctcaacat caacaccttg    420
tgtttaaaca atatcattgc gttagcgcag tacaatgtgg ccgctcaaac gccggtgatg    480
cagatatcta catgttatgt aaacggtttc aataaaggtc aaatcaatga gaagtggtt     540 ggtccagcaa gcggactgat cccacagttg tctcaggatt gttatgacat cgattcggtt    600
tttaaacgag tacatagcca gatagagcag gtcaaaaagc gcaaaacaga catagaacaa    660
caagaacaag cactgattaa attaggcata aagaccagcc agcattttgg ttggaacgat    720
acctatacat tcacaaagtg gttaggtgag cagctactca ttcaaaaact gggtaagcag    780
agtttaacta ttttgcgtcc gagtattatc gagagtgctg tacgtgaacc tgcgccgggt    840
tgggtcgagg gcgtgaaagt agcggatgcg ttgatttacg cttacgccaa gggtcgtgtt    900
tctattttcc caggtcgtga tgaaggcatc cttgacgtca ttcctgtgga tttggtggct    960
aatgcggcag ccttgtcagc ggcgcaatta atggaatcta atcagcagac ggggtatcgc   1020
atttatcagt gctgtagcgg tagtcgcaat cccataaagt tgaaggagtt tattcgccat   1080
attcaaaacg tggcgcaaag ctcgctatcag gagtggccaa aattgttcgc agataagcca   1140
caagaagcct tcaaaacggt ttccccaaaa cgtttcaaat tgtatatgag tggcttcacg   1200
```

-continued

```
gctatcactt gggcaaaaac gattatcgga cgagtgttcg gttccaacgc tgcgtcgcag   1260
catatgttaa aagcgaaaac cacggcgtca ctggcgaata ttttggtttt ttataccgcc   1320
cctaattatc gttttagtag tcagaaactt gaacagttag tcaagcagtt cgacaccaca   1380
gaacagcgct tatacgatat tcgcgccgat cactttgatt ggaaatatta tttgcaagag   1440
gtacacatgg atggactaca caaatacgcc ctagcggaca ggcaggaact gaagcccaag   1500
catgtgaaaa agcgtaagcg cgaaaccatc aggcaagcgg cgtaa              1545
```

<210> SEQ ID NO 10
<211> LENGTH: 514
<212> TYPE: PRT
<213> ORGANISM: Oceanobacter sp. RED65
<220> FEATURE:
<221> NAME/KEY: MISC_FEATURE
<223> OTHER INFORMATION: "RED65_09894" reductase

<400> SEQUENCE: 10

```
Met Ser Gln Tyr Ser Ala Phe Ser Val Ser Gln Ser Leu Lys Gly Lys
 1               5                  10                  15

His Ile Phe Leu Thr Gly Val Thr Gly Phe Leu Gly Lys Ala Ile Leu
            20                  25                  30

Glu Lys Leu Leu Tyr Ser Val Pro Gln Leu Ala Gln Ile His Ile Leu
        35                  40                  45

Val Arg Gly Gly Lys Val Ser Ala Lys Lys Arg Phe Gln His Asp Ile
    50                  55                  60

Leu Gly Ser Ser Ile Phe Glu Arg Leu Lys Glu Gln His Gly Glu His
65                  70                  75                  80

Phe Glu Glu Trp Val Gln Ser Lys Ile Asn Leu Val Glu Gly Glu Leu
                85                  90                  95

Thr Gln Pro Met Phe Asp Leu Pro Ser Ala Glu Phe Ala Gly Leu Ala
            100                 105                 110

Asn Gln Leu Asp Leu Ile Ile Asn Ser Ala Ala Ser Val Asn Phe Arg
        115                 120                 125

Glu Asn Leu Glu Lys Ala Leu Asn Ile Asn Thr Leu Cys Leu Asn Asn
    130                 135                 140

Ile Ile Ala Leu Ala Gln Tyr Asn Val Ala Ala Gln Thr Pro Val Met
145                 150                 155                 160

Gln Ile Ser Thr Cys Tyr Val Asn Gly Phe Asn Lys Gly Gln Ile Asn
                165                 170                 175

Glu Glu Val Val Gly Pro Ala Ser Gly Leu Ile Pro Gln Leu Ser Gln
            180                 185                 190

Asp Cys Tyr Asp Ile Asp Ser Val Phe Lys Arg Val His Ser Gln Ile
        195                 200                 205

Glu Gln Val Lys Lys Arg Lys Thr Asp Ile Glu Gln Glu Gln Ala
    210                 215                 220

Leu Ile Lys Leu Gly Ile Lys Thr Ser Gln His Phe Gly Trp Asn Asp
225                 230                 235                 240

Thr Tyr Thr Phe Thr Lys Trp Leu Gly Glu Gln Leu Leu Ile Gln Lys
                245                 250                 255

Leu Gly Lys Gln Ser Leu Thr Ile Leu Arg Pro Ser Ile Ile Glu Ser
            260                 265                 270

Ala Val Arg Glu Pro Ala Pro Gly Trp Val Glu Gly Val Lys Val Ala
        275                 280                 285

Asp Ala Leu Ile Tyr Ala Tyr Ala Lys Gly Arg Val Ser Ile Phe Pro
    290                 295                 300
```

Gly Arg Asp Glu Gly Ile Leu Asp Val Ile Pro Val Asp Leu Val Ala
305                 310                 315                 320

Asn Ala Ala Ala Leu Ser Ala Ala Gln Leu Met Glu Ser Asn Gln Gln
                325                 330                 335

Thr Gly Tyr Arg Ile Tyr Gln Cys Cys Ser Gly Ser Arg Asn Pro Ile
            340                 345                 350

Lys Leu Lys Glu Phe Ile Arg His Ile Gln Asn Val Ala Gln Ala Arg
        355                 360                 365

Tyr Gln Glu Trp Pro Lys Leu Phe Ala Asp Lys Pro Gln Glu Ala Phe
    370                 375                 380

Lys Thr Val Ser Pro Lys Arg Phe Lys Leu Tyr Met Ser Gly Phe Thr
385                 390                 395                 400

Ala Ile Thr Trp Ala Lys Thr Ile Ile Gly Arg Val Phe Gly Ser Asn
                405                 410                 415

Ala Ala Ser Gln His Met Leu Lys Ala Lys Thr Thr Ala Ser Leu Ala
            420                 425                 430

Asn Ile Phe Gly Phe Tyr Thr Ala Pro Asn Tyr Arg Phe Ser Ser Gln
        435                 440                 445

Lys Leu Glu Gln Leu Val Lys Gln Phe Asp Thr Glu Gln Arg Leu
    450                 455                 460

Tyr Asp Ile Arg Ala Asp His Phe Asp Trp Lys Tyr Tyr Leu Gln Glu
465                 470                 475                 480

Val His Met Asp Gly Leu His Lys Tyr Ala Leu Ala Asp Arg Gln Glu
                485                 490                 495

Leu Lys Pro Lys His Val Lys Lys Arg Lys Arg Glu Thr Ile Arg Gln
            500                 505                 510

Ala Ala

<210> SEQ ID NO 11
<211> LENGTH: 1542
<212> TYPE: DNA
<213> ORGANISM: Artificial Sequence
<220> FEATURE:
<223> OTHER INFORMATION: Synthetic construct (Maqu_2220 reductase,
      codon-optimized)

<400> SEQUENCE: 11

| | | | | | | |
|---|---|---|---|---|---|---|
| atggcgattc | aacaagttca | tcatgccgac | acgtccagta | gcaaagtgtt | gggccagctg | 60 |
| cgggggaagc | gggtcctgat | cacagggacc | accggattct | taggcaaagt | tgtgctagaa | 120 |
| cgtttaatcc | gggccgtgcc | cgatattggg | gcgatttatc | tattaattcg | tggtaataaa | 180 |
| cgtcaccccg | atgcgcgaag | ccgattccta | gaagaaatcg | cgacctcctc | cgtattcgat | 240 |
| cgcttgcggg | aggccgacag | tgaaggattt | gacgcgttct | tggaggagcg | gattcactgc | 300 |
| gtaactggtg | aagtgaccga | agcgggattt | gggatcggcc | aggaagatta | ccggaaatta | 360 |
| gcaaccgaat | tggatgccgt | gattaatagc | gcagcctctg | ttaatttccg | gaagagttg | 420 |
| gataaagcct | tggccatcaa | caccttatgt | ctgcgtaaca | ttgcaggcat | ggtggaccta | 480 |
| aatccgaagt | tagcagttct | ccaagtctcc | acctgttacg | ttaacgggat | gaattccggg | 540 |
| caagtcacgg | agtccgtgat | caaacccgct | ggggaagctg | tgccgcggtc | ccctgatggc | 600 |
| tttatgaga | tcgaagaact | cgtacgccta | ttgcaggaca | aaatcgaaga | tgtacaagcc | 660 |
| cgatactctg | ggaaggttct | ggaacgcaaa | ctggtggact | tgggtatccg | agaagccaac | 720 |
| cggtatggtt | ggagtgatac | atatacgttt | actaaatggt | tgggcgaaca | gttactaatg | 780 |

```
aaagctttga atggccgcac tttgactatc ttacggccca gtattatcga aagtgctctg    840
gaggagccag cccccggttg gattgaaggt gttaaagtcg cggatgctat tattttggct    900
tacgcccgcg agaaggtaac cttatttcct gggaagcgga gtggtattat tgacgtcatt    960
ccagtcgatt tggtcgctaa tagcattatt ctatctttag ctgaggcctt aggagaacct   1020
ggtcgtcgtc gtatttacca gtgctgttct ggcggtggta atcccatttc cctcggcgag   1080
tttattgatc atttgatggc cgaaagtaaa gctaattacg ccgcctacga ccatttgttt   1140
tatcggcaac catccaaacc ctttctcgcc gtaaaccggg cgttatttga tctagtgatt   1200
agtggcgtgc gcttgcccct aagtctaaca gaccgtgtgc tgaaactgct cggtaattct   1260
cgtgatttaa aaatgctgcg caacttagat accacccaaa gcctcgccac catttttggt   1320
ttttatactg cgcctgatta tatttttcgc aacgatgaat taatggccct cgccaatcgg   1380
atgggagaag tggataaggg gttgttcccg gttgacgccc gactcattga ttgggaactg   1440
tatctgcgca aaattcatct ggcaggcctg aatcgttatg cactcaagga acgcaaggtt   1500
tattccctca aaaccgctcg acaacgtaag aaagctgctt aa                      1542
```

<210> SEQ ID NO 12
<211> LENGTH: 1986
<212> TYPE: DNA
<213> ORGANISM: Marinobacter aquaeoli
<220> FEATURE:
<221> NAME/KEY: misc_feature
<223> OTHER INFORMATION: “Maqu_2507” reductase

<400> SEQUENCE: 12

```
atgaattatt tcctgacagg cggcaccggt tttatcggtc gttttctggt tgagaaactc     60
ttggcgcgcg gcggcaccgt gtatgttctg gttcgcgagc agtcccagga caagctggag    120
cggctccggg agcgctgggg tgcagacgac aagcaagtga aggctgtgat cggcgacctc    180
accagcaaaa accttggtat tgacgcgaaa acgctgaaat cactgaaagg aaatatcgac    240
cacgtattcc atcttgccgc ggtctacgac atgggcgcag acgaagaagc ccaggccgcc    300
accaatatcg aaggcaccag ggcggctgtt caggccgccg aagccatggg cgccaagcat    360
ttccatcatg tgtcatccat cgcggcagcg ggtctgttca agggtatctt ccgggaggat    420
atgttcgaag aagccgagaa gcttgatcat ccttacctgc gcaccaagca cgaatccgaa    480
aaagttgtgc gtgaagaatg caaggttccg ttccgcatct accgccctgg tatggtcatt    540
ggccattcgg aaaccggcga aatggacaag gttgacgggc cctattactt cttcaagatg    600
attcagaaga tccgtcatgc gttgccccag tgggtaccca ccatcggtat tgaaggtggc    660
cggctgaaca ttgtgccggt ggatttcgtg gtcgatgcac tggatcacat tgcccatctg    720
gaaggcgaag atggcaactg tttccatctg gtggactccg atccgtataa ggtgggtgag    780
atcctcaata ttttctgcga ggccggccat gccccccgca tgggtatgcg catcgattcc    840
cggatgttcg gttttattcc gccgtttatt cgccagagca tcaagaatct gcctccggtc    900
aagcgcatta ctggtgcgct tctggatgac atgggcattc cgccctcggt gatgtccttc    960
attaattacc cgacccgttt tgatacccgg gagctggagc gggttctgaa gggcacagac   1020
attgaggtgc cgcgtctgcc gtcctatgcc ccggttatct gggactactg ggagcgcaat   1080
ctggacccgg acctgttcaa ggaccgcacc ctcaagggca cggttgaagg taaggtttgc   1140
gtggtcaccg gcgcgacctc gggtattggc ctggcaacgg cagagaagct ggcagaggcc   1200
ggtgccattc tggtcattgg tgcgcgcacc aaggaaactc tggatgaagt ggcggccagt   1260
```

-continued

```
ctggaggcca agggtggcaa cgtgcatgcg taccagtgcg acttttcgga catggacgac      1320
tgcgaccgct ttgtgaagac ggtgctggat aatcacggcc acgtggatgt actggtgaat      1380
aacgcgggtc gctccatccg ccgctcgctg gcgttgtctt ttgaccggtt ccacgatttt      1440
gagcggacca tgcagctgaa ctactttggc tccgttcggc tgatcatggg ctttgcgcca      1500
gccatgctgg agcgtcgccg cgggcacgtg gtgaatattt cttccatcgg ggtacttacc      1560
aacgctccgc gtttctcggc ctatgtctcc tcgaaatccg cactgacgc gttcagccgc       1620 tgtgccgctg cagaatggtc ggatcgcaac gtgaccttca ccaccatcaa catgccgttg      1680
gtgaaaacgc cgatgatcgc gcccaccaag atctacgatt ccgtgccgac gctgacgccg      1740
gatgaagccg cccagatggt ggcggatgcg attgtgtacc ggcccaagcg cattgccacc      1800
cgtcttggcg tgttcgcgca ggttctgcat gcgctggcac cgaagatggg tgagatcatt      1860
atgaacactg gctaccggat gttcccggat tctccagcag ccgctggcag caagtccggc      1920
gaaaagccga agtctctac cgagcaggtg gcctttgcgg cgattatgcg ggggatatac      1980
tggtaa                                                                 1986
```

<210> SEQ ID NO 13
<211> LENGTH: 661
<212> TYPE: PRT
<213> ORGANISM: Marinobacter aquaeoli
<220> FEATURE:
<221> NAME/KEY: MISC_FEATURE
<223> OTHER INFORMATION: "Maqu_2507" reductase

<400> SEQUENCE: 13

```
Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
                165                 170                 175

Gly Met Val Ile Gly His Ser Glu Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Gly Arg Leu Asn Ile
    210                 215                 220
```

```
Val Pro Val Asp Phe Val Asp Ala Leu Asp His Ile Ala His Leu
225                 230                 235                 240

Glu Gly Glu Asp Gly Asn Cys Phe His Leu Val Asp Ser Asp Pro Tyr
            245                 250                 255

Lys Val Gly Glu Ile Leu Asn Ile Phe Cys Glu Ala Gly His Ala Pro
                260                 265                 270

Arg Met Gly Met Arg Ile Asp Ser Arg Met Phe Gly Phe Ile Pro Pro
            275                 280                 285

Phe Ile Arg Gln Ser Ile Lys Asn Leu Pro Pro Val Lys Arg Ile Thr
        290                 295                 300

Gly Ala Leu Leu Asp Asp Met Gly Ile Pro Pro Ser Val Met Ser Phe
305                 310                 315                 320

Ile Asn Tyr Pro Thr Arg Phe Asp Thr Arg Glu Leu Glu Arg Val Leu
                325                 330                 335

Lys Gly Thr Asp Ile Glu Val Pro Arg Leu Pro Ser Tyr Ala Pro Val
            340                 345                 350

Ile Trp Asp Tyr Trp Glu Arg Asn Leu Asp Pro Asp Leu Phe Lys Asp
        355                 360                 365

Arg Thr Leu Lys Gly Thr Val Glu Gly Lys Val Cys Val Val Thr Gly
370                 375                 380

Ala Thr Ser Gly Ile Gly Leu Ala Thr Ala Glu Lys Leu Ala Glu Ala
385                 390                 395                 400

Gly Ala Ile Leu Val Ile Gly Ala Arg Thr Lys Glu Thr Leu Asp Glu
                405                 410                 415

Val Ala Ala Ser Leu Glu Ala Lys Gly Gly Asn Val His Ala Tyr Gln
            420                 425                 430

Cys Asp Phe Ser Asp Met Asp Asp Cys Asp Arg Phe Val Lys Thr Val
        435                 440                 445

Leu Asp Asn His Gly His Val Asp Val Leu Val Asn Asn Ala Gly Arg
450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Gly His Val Val Asn
            500                 505                 510

Ile Ser Ser Ile Gly Val Leu Thr Asn Ala Pro Arg Phe Ser Ala Tyr
        515                 520                 525

Val Ser Ser Lys Ser Ala Leu Asp Ala Phe Ser Arg Cys Ala Ala Ala
530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
            580                 585                 590

Tyr Arg Pro Lys Arg Ile Ala Thr Arg Leu Gly Val Phe Ala Gln Val
        595                 600                 605

Leu His Ala Leu Ala Pro Lys Met Gly Glu Ile Ile Met Asn Thr Gly
610                 615                 620

Tyr Arg Met Phe Pro Asp Ser Pro Ala Ala Gly Ser Lys Ser Gly
                625                 630                 635                 640

Glu Lys Pro Lys Val Ser Thr Glu Gln Val Ala Phe Ala Ala Ile Met
```

```
                    645                 650                 655
Arg Gly Ile Tyr Trp
        660

<210> SEQ ID NO 14
<211> LENGTH: 989
<212> TYPE: DNA
<213> ORGANISM: Synechocystis sp. PCC 6803
<220> FEATURE:
<221> NAME/KEY: misc_feature
<223> OTHER INFORMATION: RS1 up sequence

<400> SEQUENCE: 14
attgctgaag cggaatccct ggttaatgcc gccgccgatg ccaattgcat tctccaagtg     60
gggcacattg aacgcttcaa cccggcattt ttagagctaa ccaaaattct caaaacggaa    120
gagttattgg cgatcgaagc ccatcgcatg agtccctatt cccagcgggc caatgatgtc    180
tccgtggtat tggatttgat gatccatgac attgacctgt tgctggaatt ggtgggttcg    240
gaagtggtta aactgtccgc cagtggcagt cgggcttctg ggtcaggata tttggattat    300
gtcaccgcta cgttaggctt ctcctccggc attgtggcca ccctcaccgc cagtaaggtc    360
acccatcgta aaattcgttc catcgccgcc cactgcaaaa attccctcac cgaagcggat    420
tttctcaata cgaaattttt gatccatcgc caaaccaccg ctgattggag cgcggactat    480
ggccaggtat tgtatcgcca ggatggtcta atcgaaaagg tttacaccag taatattgaa    540
cctctccacg ctgaattaga acattttatt cattgtgtta ggggaggtga tcaaccctca    600 gtgggggggag aacaggccct caaggccctg aagttagcca gtttaattga agaaatggcc    660
ctggacagtc aggaatggca tggggggggaa gttgtgacag aatatcaaga tgccaccctg    720
gccctcagtg cgagtgttta aatcaactta attaatgcaa ttattgcgag ttcaaactcg    780
ataactttgt gaaatattac tgttgaatta atctatgact attcaataca ccccccctagc    840 cgatcgcctg ttggcctacc tcgccgccga tcgcctaaat ctcagcgcca agagtagttc    900
cctcaacacc agtattctgc tcagcagtga cctattcaat caggaagggg gaattgtaac    960
agccaactat ggctttgatg gttatatgg                                       989

<210> SEQ ID NO 15
<211> LENGTH: 989
<212> TYPE: DNA
<213> ORGANISM: Synechocystis sp. PCC 6803
<220> FEATURE:
<221> NAME/KEY: misc_feature
<223> OTHER INFORMATION: RS1 down sequence

<400> SEQUENCE: 15
ccggtatgga tggcaccgat gcggaatccc aacagattgc ctttgacaac aatgtggcct     60
ggaataacct gggggatttg tccaccacca cccaacgggc ctacacttcg gctattagca    120
cagacacagt gcagagtgtt tatggcgtta atctggaaaa aaacgataac attcccattg    180
tttttgcgtg gcccattttt cccaccaccc ttaatcccac agattttcag gtaatgctta    240
acacggggga aattgtcacc ccggtgatcg cctcttttgat tcccaacagt gaatacaacg    300
aacggcaaac ggtagtaatt acgggcaatt ttggtaatcg tttaaccccca ggcacggagg    360 gagcgattta tccgtttttcc gtaggcacag tgttggacag tactccttttg gaaatggtgg    420 gacccaacgg cccggtcagt gcggtgggta ttaccattga tagtctcaac ccctacgtgg    480
ccggcaatgg tcccaaaatt gtcgccgcta agttagaccg cttcagtgac ctgggggaag    540
```

```
gggctcccct ctggttagcc accaatcaaa ataacagtgg cggggattta tatggagacc      600
aagcccaatt tcgtttgcga atttacacca gcgccggttt ttcccccgat ggcattgcca      660
gtttactacc cacagaattt gaacggtatt ttcaactcca agcggaagat attacgggac      720
ggacagttat cctaacccaa actggtgttg attatgaaat tcccggcttt ggtctggtgc      780
aggtgttggg gctggcggat tggccgggg ttcaggacag ctatgacctg acttacatcg      840
aagatcatga caactattac gacattatcc tcaaggggga cgaagccgca gttcgccaaa      900
ttaagagggt tgctttgccc tccgaagggg attattcggc ggtttataat cccggtggcc      960
ccggcaatga tccagagaat ggtccccca                                         989
```

```
<210> SEQ ID NO 16
<211> LENGTH: 1032
<212> TYPE: DNA
<213> ORGANISM: Synechocystis sp. PCC 6803
<220> FEATURE:
<221> NAME/KEY: misc_feature
<223> OTHER INFORMATION: RS2 up sequence

<400> SEQUENCE: 16
tatttgcccg tattctgccc tatcccaag ccctagccca ggcgatcgcc gctgggttta       60
cttccgaccg tatcattgct ttgcgccccc ccgtagccga accattggaa aaagccctgt      120
ggcaacaatg gcaaattcaa ggggtggtaa ctaaagcctc cggtgcccag gggggagaat      180
tggttaagca aaaagtggcg gaagcgttgg gggtaaatct gatcagaatt gcccgtcccc      240
agactattcc agggcaaata actgacgatt taagccagat caaccaattt tgccaaagac      300
atttgccaag ctaaaaacga aaatttgtta agtattgcaa cggtggtttc ccaggggcag      360
agcgtccccg taagatgaga ttttttaaaga ccccccattag cgtggggcta tcccttttaaa  420 aaccgtctt attctggaga atctcaatgc atagcttttt gttggccacc gccgttcccg      480
ccaccctgtc ctggagccct aaagttgctg gggtgatgat tgcttgcaac attttggcga     540
tcgcctttgg taaattgacc atcaaacaac aaaatgtggg caccccatg ccttcctcta      600 acttctttgg cggctttggt ttaggggctg tgctgggcac cgctagcttt ggccacatcc     660
tcggcgctgg agtaattctg gggctagcca atatgggagt actttaaggc tcgattctga    720
atggactagc ttttatccttt tgggaaaata tcaaaggcga tcgggcaatt gaaagaaaag   780
cctggtcgct ttttttgttag ggattaggga aaatgccaaa acgcaccaag gtggtaatta    840
tggctccgat gacggcaaga atcaacgccc aaatttgagc attagcccgc cctttgacat     900 cttttaacatc atccttgact gtacctatct ccatcctgac cgcagataac tcggttttca    960
ccgttgccat atcgatctta agagaagtta catcttttg gaggtcatcg agtttggtct     1020
taatttcccc ca                                                         1032
```

```
<210> SEQ ID NO 17
<211> LENGTH: 824
<212> TYPE: DNA
<213> ORGANISM: Synechocystis sp. PCC 6803
<220> FEATURE:
<221> NAME/KEY: misc_feature
<223> OTHER INFORMATION: RS2 down sequence

<400> SEQUENCE: 17
cctttaaatc ggtttctata gttacactca ttggcttttg cctgcaaagc aatatttcct       60
gataccccta gggtaaatca tgggaaatgg cgatcgccgg agtttctcct gtttgctgga     120
gggctgtctg caacatcttg gtgctgacca cggaatcggt ggcgaggtta aagagggat     180
```

```
tagccagaat acctgccagc gaggtagcaa ccaaagtagc gacaatgccc acctgtaggg      240
gacgcatgcc gggtaaattc catttgatgg ccgggtaatt tttgattact tcggacattt      300
cctggggctc cttcaccacc atcattttca ccacccggat gtagtagtag atggaaacta      360
cactggtaac cagaccaagt aggactaggc catacaatcc cgattgccaa ccggcccaga      420
agatgtaaat tttgccgaaa aagcccgcca gaggaggaat gccccccaag gataataaac      480
aaatgctcaa gcccaaggtt aacaaggggt ctttgtggta cagaccagcg taatcactaa      540
tttggtcact gccagtgcgg agggtgaaga gaataatgca actaaacgcc cccaggttca      600
taaacagata gatgagcatg tagaaaacca tgctggcgta accatcttca ctgccggcca      660
ctaggccaat catcacaaag cctgcttgac cgatggaaga gtaggccaac atccgtttca      720
tgctggtttg ggctaaagcc accacgttgc ccagcaccat gctcaacacg gccagagcgg      780
tgaaaataac gtgccactca tcggtaatac caccaaaggc agtc                      824
```

<210> SEQ ID NO 18
<211> LENGTH: 5767
<212> TYPE: DNA
<213> ORGANISM: Artificial Sequence
<220> FEATURE:
<223> OTHER INFORMATION: Synthetic construct (MexB, MexA, OprM operon,
      genes codon-optimized for expression in Synechocystis)

<400> SEQUENCE: 18

```
atgtccaaat tctttattga ccgcccaatt tttgcgtggg ttatcgcact cgtaattatg      60
ctggcaggtg gtctcagcat cctgtctctg cctgtcaacc agtatccagc aatcgcgcct      120
ccggctattg cagtgcaagt ttcttatccg ggtgcctctg cggagactgt tcaggacact      180
gttgttcaag taatcgagca acagatgaat ggcatcgaca acctccgcta tatcagctcc      240
gaaagcaatt ccgacggctc tatgaccatt actgtcacgt ttgaacaggg taccgaccca      300
gacatcgcgc aggtccaagt acagaacaaa ctccaactcg ccacgccgct gctcccgcag      360
gaggttcaac gtcaaggtat ccgtgttacc aaagctgtga agaacttcct catggtagtt      420
ggcgtagttt ctaccgacgg ttccatgacg aaggaggacc tctccaatta cattgtgtcc      480
aacattcaag accctctgtc ccgtactaaa ggcgttggtg acttccaggt atttggcagc      540
cagtactcca tgcgtatttg gctcgacccg gcaaaactca actcttacca gctcacgcca      600
ggcgatgtta gctccgcgat ccaggcccaa aacgtacaga ttagctctgg tcagctgggt      660
ggcctcccag ccgttaaggg tcagcaactg aatgccacga ttattggtaa acccgcctg      720 caaaccgcgg aacagttcga gaacattctg ctcaaagtaa acccggacgg tagccaagtc      780
cgtctgaaag acgtggcgga cgtggtctc ggtggccagg actactctat caacgcacaa      840
ttcaacggtt ctccggcgtc tggtatcgct attaagctcg caactggtgc gaacgctctg      900
gacactgcca aggcgattcg tcagactatc gcaaacctcg agccgtttat gccgcagggt      960
atgaaagttg tataccccata cgatactacc ccggtcgtgt ctgcctctat ccacgaagtc      1020
gttaaaactc tcggcgaagc gattctcctc gtatttctgg tgatgtatct gtttctccaa      1080
aacttccgcg cgactctgat cccgaccatc gcggtgccag ttgtgctgct cggcacctt      1140 ggtgtcctcg ctgcattcgg tttttccatc aacactctga ccatgttcgg catggtgctc      1200
gctatcggcc tgctcgtaga tgatgcgatt gttgtggttg aaaacgtcga acgtgttatg      1260
gcggaggaag gctctccccc gcgtgaagcc gcacgtaaat ctatgggtca gattcaaggc      1320
gcgctggtgg gtattgctat ggttctctcc gctgtctttc tgccgatggc tttcttcggc      1380
```

```
ggctccaccg gtgtgattta ccgccaattc tccattacca tcgtttctgc gatggccctg    1440
tccgttatcg tcgcgctcat tctcacccca gcactgtgcg cgaccatgct gaagccaatc    1500
gagaagggcg atcatggtga acacaagggc ggtttctttg gttggtttaa ccgtatgttt    1560
ctgtctacca ctcacggtta cgagcgtggt gttgcgtcca ttctgaaaca tcgtgcgccg    1620
tacctgctca tttatgtcgt gatcgtagcg ggcatgatct ggatgtttac ccgcatccca    1680
accgcattcc tgcctgacga ggaccaaggt gtgctcttcg cgcaagtgca gacccctcct    1740
ggctctagcg ctgaacgtac gcaagtagtt gtggacagca tgcgtgagta tctgctggaa    1800
aaggaaagct cctctgtaag ctccgttttt acggtgaccg ctttaacttt gcgggtcgt     1860 ggtcaatcta gcggtatggc cttcatcatg ctgaaacctt gggaagagcg ccctggtggc    1920
gaaaattctg tattcgaact cgcgaaacgc gcccagatgc acttcttctc tttcaaagac    1980
gccatggttt tcgcttttgc tccgccgtct gttctggaac tcggtaacgc gacgggtttc    2040
gacctgttcc tgcaagacca ggctggcgtc ggtcatgaag tactgctcca ggcgcgtaac    2100
aagttcctga tgctcgcggc acaaaaccct gccctccagc gtgttcgtcc gaacggcatg    2160
tctgatgaac gcagtacaa gctcgaaatt gacgacgaga agcgtccgc gctcggtgta     2220 tccctcgccg acattaactc tacggtgtct atcgcgtggg gcagcagcta tgtcaatgac    2280
ttcatcgacc gtggccgtgt gaagcgcgtc tatctccaag gtcgccctga cgcccgtatg    2340
aatccggacg acctcagcaa atggtacgtt cgtaacgaca aggcgaaat ggttccgttt     2400 aatgcgtttg ccacgggcaa gtgggagtac ggctccccga agctggaacg ctataacggt    2460
gttccggcaa tggaaatcct cggtgagcca gccccaggtc tctcttccgg tgacgcaatg    2520
gcggctgttg aagaaattgt caaacaactg cctaagggtg tcggctactc ctggaccggc    2580
ctgtcctacg aagaacgcct ctctggctcc caagctccag ccctctatgc tctctccctg    2640
ctggtagtct tcctgtgtct ggccgcgctg tatgagtctt ggagcatccc gttttccgtc    2700
atgctcgtgg ttccactcgg cgtgattggt gcgctcctcg cgacttctat gcgtggtctg    2760
agcaacgatg tattcttcca agttggtctc ctgaccacca ttggcctcag cgcgaaaaat    2820
gccatcctga ttgtggaatt tgcgaaagaa ctgcacgaac aaggcaaagg cattgtcgag    2880
gctgctatcg aagcctgtcg tatgcgcctg cgtccgatcg ttatgactag cctcgcgttc    2940
atcctgggtg ttgtgcctct ggcgattagc acgggtgcgg gttccggttc caacatgct   3000 attggcactg gtgtaatcgg tggtatggtt accgcgaccg ttctggccat cttctgggtg    3060
ccgctgtttt acgttgcagt cagcacccte ttcaaggatg aggcatctaa acagcaggcg    3120
agcgtagaga aggtcaata gcggccgca tgcaacgaac gccagccatg cgtgtactgg     3180
ttccggccct gctggtcgcg atttcggccc tttccgggtg cggaaaaagc gaggcgccgc    3240
cgccggcgca aacgccggag gtcgggatcg tgaccctgga agcgcagacg gtgaccctga    3300
ataccgagct gccgggccgg accaatgcgt tccgcatcgc cgaggtgcgt ccccaggtga    3360
acggcatcat cctcaagcgc ctgttcaagg aaggcagcga cgtcaaggcc gggcagcagc    3420
tctaccagat cgaccccgcc acctacgagg ccgactacca gagcgcccag gccaacctgg    3480
cttcgaccca ggaacaggcc cagcgctaca agctgctggt cgccgaccag gccgtgagca    3540
agcagcagta cgccgacgcc aatgccgcct acctgcagtc caaggcggcg gtggagcagg    3600
cgcggatcaa cctgcgctac accaaggtgc tgtcgccgat ctccggccgc atcggccgtt    3660
ccgcggtgac cgaaggcgcc ctggtgacca acggccaggc caacgcgatg gccaccgtgc    3720
```

-continued

```
aacagctcga cccgatctac gtcgacgtca cccagccgtc caccgccctg ctgcgcctgc    3780
gccgcgaact ggccagcggc cagttggagc gcgccggcga caacgcggcg aaggtctccc    3840
tgaagctgga ggacggtagc caataccgc tggaaggtcg cctcgaattc tccgaggttt    3900
ccgtcgacga aggcaccggc tcggtcacca tccgcgccgt gttccccaac ccgaacaacg    3960
agctgctgcc cggcatgttc gttcacgcgc agttgcagga aggcgtcaag cagaaggcca    4020
tcctcgctcc gcagcaaggc gtgacccgcg acctcaaggg ccaggctacc gcgctggtgg    4080
tgaacgcgca gaacaaggtc gagctgcggg tgatcaaggc cgaccgggtg atcggcgaca    4140
agtggctggt taccgaaggc ctgaacgccg gcgacaagat cattaccgaa ggcctgcagt    4200
tcgtgcagcc gggtgtcgag gtgaagaccg tgccggcgaa gaatgtcgcg tccgcgcaga    4260
aggccgacgc cgctccggcg aaaaccgaca gcaagggctg agtttaaaca tgaaacggtc    4320
cttcctttcc ctggcggtag ccgctgtcgt tctgtccggc tgctcgctga tccccgacta    4380
ccagcgcccc gaggcgccgg tagccgcggc ctacccgcaa gggcaggcct acgggcagaa    4440
caccggcgcg gcggccgttc cggccgccga catcggctgg cgcgagttct tccgcgaccc    4500
gcagttgcag caactgatcg gcgtggcgct ggaaaacaac cgcgacctgc gggtcgccgc    4560
gctgaacgtc gaggccttcc gggcgcagta ccgcatccag cgggccgacc tgttcccgcg    4620
gatcggcgtg gacggtagcg gcaccccgcca gcgtttgccg ggcgacctgt cgaccaccgg    4680
cagtccggcg atttccagcc agtacggggt gaccctgggc actaccgcct gggaactcga    4740
tctcttcggc cgcctgcgca gcctgcgcga ccaggccctg gagcagtacc tggcgaccga    4800
acaggcgcag cgcagcgcgc agaccaccct ggtggccagc gtggcgaccg cctacctgac    4860
gctgaaggcc gaccaggcgc agttgcagct gaccaaggac accctgggca cctaccagaa    4920
gagtttcgac ctgacccagc gcagctacga cgtcggcgtc gcctccgcgc tcgacctgcg    4980
ccaggcgcag accgccgtgg aaggcgcccg cgcgaccctg gcgcagtaca cccgcctggt    5040
agcccaggac cagaatgcgc tggtcctgct gctgggctcc gggatcccgg cgaacctgcc    5100
gcaaggcctg ggcctggacc agaccctgct gaccgaagtg ccggcgggtc tgccgtcgga    5160
cctgctgcaa cggcgcccgg acatcctcga ggccgagcac cagctcatgg ctgccaacgc    5220
cagcatcggc gccgcgcgcg cggcgttctt cccgagcatc agcctgaccg ccaacgccgg    5280
caccatgagc cgccaactgt ccggcctgtt cgacgccggt tcgggttcct ggttgttcca    5340
gccgtcgatc aacctgccga tcttcaccgc cggcagcctg cgtgccagcc tggactacgc    5400
gaagatccag aaggacatca acgtcgcgca gtacgagaag gcgatccaga cggcgttcca    5460
ggaagtcgcc gacggcctgg ccgcgcgcgg taccttcacc gagcagttgc aggcgcagcg    5520
cgatctggtc aaggccagcg acgagtacta ccagctcgcc gacaagcgct atcgcacggg    5580
ggtggacaac tacctgaccc tgctcgacgc gcaacgctcg ctgttcaccg cgcagcagca    5640
actgatcacc gaccgcctca atcagctgac cagcgaggtc aacctgtaca aggccctcgg    5700
cggcggctgg aaccagcaga ccgtgaccca gcagcagacc gcgaagaagg aagatcccca    5760
ggcttga                                                              5767
```

<210> SEQ ID NO 19
<211> LENGTH: 1046
<212> TYPE: PRT
<213> ORGANISM: Pseudomonas aeruginosa
<220> FEATURE:
<221> NAME/KEY: MISC_FEATURE
<223> OTHER INFORMATION: MexB

```
<400> SEQUENCE: 19

Met Ser Lys Phe Phe Ile Asp Arg Pro Ile Phe Ala Trp Val Ile Ala
1               5                   10                  15

Leu Val Ile Met Leu Ala Gly Gly Leu Ser Ile Leu Ser Leu Pro Val
            20                  25                  30

Asn Gln Tyr Pro Ala Ile Ala Pro Pro Ala Ile Ala Val Gln Val Ser
        35                  40                  45

Tyr Pro Gly Ala Ser Ala Glu Thr Val Gln Asp Thr Val Val Gln Val
    50                  55                  60

Ile Glu Gln Gln Met Asn Gly Ile Asp Asn Leu Arg Tyr Ile Ser Ser
65                  70                  75                  80

Glu Ser Asn Ser Asp Gly Ser Met Thr Ile Thr Val Thr Phe Glu Gln
                85                  90                  95

Gly Thr Asp Pro Asp Ile Ala Gln Val Gln Val Gln Asn Lys Leu Gln
            100                 105                 110

Leu Ala Thr Pro Leu Leu Pro Gln Glu Val Gln Arg Gln Gly Ile Arg
            115                 120                 125

Val Thr Lys Ala Val Lys Asn Phe Leu Met Val Val Gly Val Val Ser
130                 135                 140

Thr Asp Gly Ser Met Thr Lys Glu Asp Leu Ser Asn Tyr Ile Val Ser
145                 150                 155                 160

Asn Ile Gln Asp Pro Leu Ser Arg Thr Lys Gly Val Gly Asp Phe Gln
                165                 170                 175

Val Phe Gly Ser Gln Tyr Ser Met Arg Ile Trp Leu Asp Pro Ala Lys
            180                 185                 190

Leu Asn Ser Tyr Gln Leu Thr Pro Gly Asp Val Ser Ser Ala Ile Gln
            195                 200                 205

Ala Gln Asn Val Gln Ile Ser Ser Gly Gln Leu Gly Gly Leu Pro Ala
        210                 215                 220

Val Lys Gly Gln Gln Leu Asn Ala Thr Ile Ile Gly Lys Thr Arg Leu
225                 230                 235                 240

Gln Thr Ala Glu Gln Phe Glu Asn Ile Leu Leu Lys Val Asn Pro Asp
                245                 250                 255

Gly Ser Gln Val Arg Leu Lys Asp Val Ala Asp Val Gly Leu Gly Gly
            260                 265                 270

Gln Asp Tyr Ser Ile Asn Ala Gln Phe Asn Gly Ser Pro Ala Ser Gly
            275                 280                 285

Ile Ala Ile Lys Leu Ala Thr Gly Ala Asn Ala Leu Asp Thr Ala Lys
        290                 295                 300

Ala Ile Arg Gln Thr Ile Ala Asn Leu Glu Pro Phe Met Pro Gln Gly
305                 310                 315                 320

Met Lys Val Val Tyr Pro Tyr Asp Thr Thr Pro Val Val Ser Ala Ser
                325                 330                 335

Ile His Glu Val Val Lys Thr Leu Gly Glu Ala Ile Leu Leu Val Phe
            340                 345                 350

Leu Val Met Tyr Leu Phe Leu Gln Asn Phe Arg Ala Thr Leu Ile Pro
            355                 360                 365

Thr Ile Ala Val Pro Val Val Leu Leu Gly Thr Phe Gly Val Leu Ala
        370                 375                 380

Ala Phe Gly Phe Ser Ile Asn Thr Leu Thr Met Phe Gly Met Val Leu
385                 390                 395                 400

Ala Ile Gly Leu Leu Val Asp Asp Ala Ile Val Val Val Glu Asn Val
                405                 410                 415
```

```
Glu Arg Val Met Ala Glu Gly Leu Ser Pro Arg Glu Ala Ala Arg
            420                 425                 430

Lys Ser Met Gly Gln Ile Gln Gly Ala Leu Val Gly Ile Ala Met Val
        435                 440                 445

Leu Ser Ala Val Phe Leu Pro Met Ala Phe Gly Gly Ser Thr Gly
    450                 455                 460

Val Ile Tyr Arg Gln Phe Ser Ile Thr Ile Val Ser Ala Met Ala Leu
465             470                 475                 480

Ser Val Ile Val Ala Leu Ile Leu Thr Pro Ala Leu Cys Ala Thr Met
                485                 490                 495

Leu Lys Pro Ile Glu Lys Gly Asp His Gly Glu His Lys Gly Gly Phe
            500                 505                 510

Phe Gly Trp Phe Asn Arg Met Phe Leu Ser Thr Thr His Gly Tyr Glu
        515                 520                 525

Arg Gly Val Ala Ser Ile Leu Lys His Arg Ala Pro Tyr Leu Leu Ile
    530                 535                 540

Tyr Val Val Ile Val Ala Gly Met Ile Trp Met Phe Thr Arg Ile Pro
545             550                 555                 560

Thr Ala Phe Leu Pro Asp Glu Asp Gln Gly Val Leu Phe Ala Gln Val
                565                 570                 575

Gln Thr Pro Pro Gly Ser Ser Ala Glu Arg Thr Gln Val Val Asp
            580                 585                 590

Ser Met Arg Glu Tyr Leu Leu Glu Lys Glu Ser Ser Ser Val Ser Ser
        595                 600                 605

Val Phe Thr Val Thr Gly Phe Asn Phe Ala Gly Arg Gly Gln Ser Ser
    610                 615                 620

Gly Met Ala Phe Ile Met Leu Lys Pro Trp Glu Glu Arg Pro Gly Gly
625             630                 635                 640

Glu Asn Ser Val Phe Glu Leu Ala Lys Arg Ala Gln Met His Phe Phe
                645                 650                 655

Ser Phe Lys Asp Ala Met Val Phe Ala Phe Ala Pro Pro Ser Val Leu
            660                 665                 670

Glu Leu Gly Asn Ala Thr Gly Phe Asp Leu Phe Leu Gln Asp Gln Ala
        675                 680                 685

Gly Val Gly His Glu Val Leu Leu Gln Ala Arg Asn Lys Phe Leu Met
    690                 695                 700

Leu Ala Ala Gln Asn Pro Ala Leu Gln Arg Val Arg Pro Asn Gly Met
705             710                 715                 720

Ser Asp Glu Pro Gln Tyr Lys Leu Glu Ile Asp Asp Glu Lys Ala Ser
                725                 730                 735

Ala Leu Gly Val Ser Leu Ala Asp Ile Asn Ser Thr Val Ser Ile Ala
            740                 745                 750

Trp Gly Ser Ser Tyr Val Asn Asp Phe Ile Asp Arg Gly Arg Val Lys
        755                 760                 765

Arg Val Tyr Leu Gln Gly Arg Pro Asp Ala Arg Met Asn Pro Asp Asp
    770                 775                 780

Leu Ser Lys Trp Tyr Val Arg Asn Asp Lys Gly Glu Met Val Pro Phe
785             790                 795                 800

Asn Ala Phe Ala Thr Gly Lys Trp Glu Tyr Gly Ser Pro Lys Leu Glu
                805                 810                 815

Arg Tyr Asn Gly Val Pro Ala Met Glu Ile Leu Gly Glu Pro Ala Pro
            820                 825                 830
```

```
Gly Leu Ser Ser Gly Asp Ala Met Ala Ala Val Glu Ile Val Lys
            835                 840                 845

Gln Leu Pro Lys Gly Val Gly Tyr Ser Trp Thr Gly Leu Ser Tyr Glu
850                 855                 860

Glu Arg Leu Ser Gly Ser Gln Ala Pro Ala Leu Tyr Ala Leu Ser Leu
865                 870                 875                 880

Leu Val Val Phe Leu Cys Leu Ala Ala Leu Tyr Glu Ser Trp Ser Ile
                885                 890                 895

Pro Phe Ser Val Met Leu Val Val Pro Leu Gly Val Ile Gly Ala Leu
                900                 905                 910

Leu Ala Thr Ser Met Arg Gly Leu Ser Asn Asp Val Phe Phe Gln Val
                915                 920                 925

Gly Leu Leu Thr Thr Ile Gly Leu Ser Ala Lys Asn Ala Ile Leu Ile
            930                 935                 940

Val Glu Phe Ala Lys Glu Leu His Glu Gln Gly Lys Gly Ile Val Glu
945                 950                 955                 960

Ala Ala Ile Glu Ala Cys Arg Met Arg Leu Arg Pro Ile Val Met Thr
                965                 970                 975

Ser Leu Ala Phe Ile Leu Gly Val Val Pro Leu Ala Ile Ser Thr Gly
                980                 985                 990

Ala Gly Ser Gly Ser Gln His Ala Ile Gly Thr Gly Val Ile Gly Gly
            995                 1000                1005

Met Val Thr Ala Thr Val Leu Ala Ile Phe Trp Val Pro Leu Phe
    1010                1015                1020

Tyr Val Ala Val Ser Thr Leu Phe Lys Asp Glu Ala Ser Lys Gln
    1025                1030                1035

Gln Ala Ser Val Glu Lys Gly Gln
    1040                1045

<210> SEQ ID NO 20
<211> LENGTH: 383
<212> TYPE: PRT
<213> ORGANISM: Pseudomonas aeruginosa
<220> FEATURE:
<221> NAME/KEY: MISC_FEATURE
<223> OTHER INFORMATION: MexA

<400> SEQUENCE: 20

Met Gln Arg Thr Pro Ala Met Arg Val Leu Val Pro Ala Leu Leu Val
1               5                   10                  15

Ala Ile Ser Ala Leu Ser Gly Cys Gly Lys Ser Glu Ala Pro Pro Pro
            20                  25                  30

Ala Gln Thr Pro Glu Val Gly Ile Val Thr Leu Glu Ala Gln Thr Val
        35                  40                  45

Thr Leu Asn Thr Glu Leu Pro Gly Arg Thr Asn Ala Phe Arg Ile Ala
    50                  55                  60

Glu Val Arg Pro Gln Val Asn Gly Ile Ile Leu Lys Arg Leu Phe Lys
65                  70                  75                  80

Glu Gly Ser Asp Val Lys Ala Gly Gln Gln Leu Tyr Gln Ile Asp Pro
                85                  90                  95

Ala Thr Tyr Glu Ala Asp Tyr Gln Ser Ala Gln Ala Asn Leu Ala Ser
            100                 105                 110

Thr Gln Glu Gln Ala Gln Arg Tyr Lys Leu Leu Val Ala Asp Gln Ala
        115                 120                 125

Val Ser Lys Gln Gln Tyr Ala Asp Ala Asn Ala Ala Tyr Leu Gln Ser
    130                 135                 140
```

Lys Ala Ala Val Glu Gln Ala Arg Ile Asn Leu Arg Tyr Thr Lys Val
145                 150                 155                 160

Leu Ser Pro Ile Ser Gly Arg Ile Gly Arg Ser Ala Val Thr Glu Gly
            165                 170                 175

Ala Leu Val Thr Asn Gly Gln Ala Asn Ala Met Ala Thr Val Gln Gln
        180                 185                 190

Leu Asp Pro Ile Tyr Val Asp Val Thr Gln Pro Ser Thr Ala Leu Leu
    195                 200                 205

Arg Leu Arg Arg Glu Leu Ala Ser Gly Gln Leu Glu Arg Ala Gly Asp
210                 215                 220

Asn Ala Ala Lys Val Ser Leu Lys Leu Glu Asp Gly Ser Gln Tyr Pro
225                 230                 235                 240

Leu Glu Gly Arg Leu Glu Phe Ser Glu Val Ser Val Asp Glu Gly Thr
            245                 250                 255

Gly Ser Val Thr Ile Arg Ala Val Phe Pro Asn Pro Asn Asn Glu Leu
        260                 265                 270

Leu Pro Gly Met Phe Val His Ala Gln Leu Gln Glu Gly Val Lys Gln
    275                 280                 285

Lys Ala Ile Leu Ala Pro Gln Gln Gly Val Thr Arg Asp Leu Lys Gly
290                 295                 300

Gln Ala Thr Ala Leu Val Val Asn Ala Gln Asn Lys Val Glu Leu Arg
305                 310                 315                 320

Val Ile Lys Ala Asp Arg Val Ile Gly Asp Lys Trp Leu Val Thr Glu
            325                 330                 335

Gly Leu Asn Ala Gly Asp Lys Ile Ile Thr Glu Gly Leu Gln Phe Val
        340                 345                 350

Gln Pro Gly Val Glu Val Lys Thr Val Pro Ala Lys Asn Val Ala Ser
    355                 360                 365

Ala Gln Lys Ala Asp Ala Ala Pro Ala Lys Thr Asp Ser Lys Gly
370                 375                 380

<210> SEQ ID NO 21
<211> LENGTH: 485
<212> TYPE: PRT
<213> ORGANISM: Pseudomonas aeruginosa
<220> FEATURE:
<221> NAME/KEY: MISC_FEATURE
<223> OTHER INFORMATION: oprM

<400> SEQUENCE: 21

Met Lys Arg Ser Phe Leu Ser Leu Ala Val Ala Val Val Leu Ser
1               5                   10                  15

Gly Cys Ser Leu Ile Pro Asp Tyr Gln Arg Pro Glu Ala Pro Val Ala
            20                  25                  30

Ala Ala Tyr Pro Gln Gly Gln Ala Tyr Gly Gln Asn Thr Gly Ala Ala
        35                  40                  45

Ala Val Pro Ala Ala Asp Ile Gly Trp Arg Glu Phe Phe Arg Asp Pro
    50                  55                  60

Gln Leu Gln Gln Leu Ile Gly Val Ala Leu Glu Asn Asn Arg Asp Leu
65                  70                  75                  80

Arg Val Ala Ala Leu Asn Val Glu Ala Phe Arg Ala Gln Tyr Arg Ile
            85                  90                  95

Gln Arg Ala Asp Leu Phe Pro Arg Ile Gly Val Asp Gly Ser Gly Thr
        100                 105                 110

Arg Gln Arg Leu Pro Gly Asp Leu Ser Thr Thr Gly Ser Pro Ala Ile

```
       115                 120                 125
Ser Ser Gln Tyr Gly Val Thr Leu Gly Thr Thr Ala Trp Glu Leu Asp
    130                 135                 140

Leu Phe Gly Arg Leu Arg Ser Leu Arg Asp Gln Ala Leu Glu Gln Tyr
145                 150                 155                 160

Leu Ala Thr Glu Gln Ala Gln Arg Ser Ala Gln Thr Thr Leu Val Ala
                165                 170                 175

Ser Val Ala Thr Ala Tyr Leu Thr Leu Lys Ala Asp Gln Ala Gln Leu
            180                 185                 190

Gln Leu Thr Lys Asp Thr Leu Gly Thr Tyr Gln Lys Ser Phe Asp Leu
        195                 200                 205

Thr Gln Arg Ser Tyr Asp Val Gly Val Ala Ser Ala Leu Asp Leu Arg
    210                 215                 220

Gln Ala Gln Thr Ala Val Glu Gly Ala Arg Ala Thr Leu Ala Gln Tyr
225                 230                 235                 240

Thr Arg Leu Val Ala Gln Asp Gln Asn Ala Leu Val Leu Leu Leu Gly
                245                 250                 255

Ser Gly Ile Pro Ala Asn Leu Pro Gln Gly Leu Gly Leu Asp Gln Thr
            260                 265                 270

Leu Leu Thr Glu Val Pro Ala Gly Leu Pro Ser Asp Leu Leu Gln Arg
        275                 280                 285

Arg Pro Asp Ile Leu Glu Ala Glu His Gln Leu Met Ala Ala Asn Ala
    290                 295                 300

Ser Ile Gly Ala Ala Arg Ala Ala Phe Phe Pro Ser Ile Ser Leu Thr
305                 310                 315                 320

Ala Asn Ala Gly Thr Met Ser Arg Gln Leu Ser Gly Leu Phe Asp Ala
                325                 330                 335

Gly Ser Gly Ser Trp Leu Phe Gln Pro Ser Ile Asn Leu Pro Ile Phe
            340                 345                 350

Thr Ala Gly Ser Leu Arg Ala Ser Leu Asp Tyr Ala Lys Ile Gln Lys
        355                 360                 365

Asp Ile Asn Val Ala Gln Tyr Glu Lys Ala Ile Gln Thr Ala Phe Gln
    370                 375                 380

Glu Val Ala Asp Gly Leu Ala Ala Arg Gly Thr Phe Thr Glu Gln Leu
385                 390                 395                 400

Gln Ala Gln Arg Asp Leu Val Lys Ala Ser Asp Glu Tyr Tyr Gln Leu
                405                 410                 415

Ala Asp Lys Arg Tyr Arg Thr Gly Val Asp Asn Tyr Leu Thr Leu Leu
            420                 425                 430

Asp Ala Gln Arg Ser Leu Phe Thr Ala Gln Gln Leu Ile Thr Asp
        435                 440                 445

Arg Leu Asn Gln Leu Thr Ser Glu Val Asn Leu Tyr Lys Ala Leu Gly
    450                 455                 460

Gly Gly Trp Asn Gln Gln Thr Val Thr Gln Gln Thr Ala Lys Lys
465                 470                 475                 480

Glu Asp Pro Gln Ala
            485

<210> SEQ ID NO 22
<211> LENGTH: 401
<212> TYPE: DNA
<213> ORGANISM: Synechocystis PCC 6803
<220> FEATURE:
<221> NAME/KEY: misc_feature
<223> OTHER INFORMATION: nrsB promoter
```

<400> SEQUENCE: 22

```
catctagtcc ttcgacacgg ttttccggtt ctcctaacgc tgttaacatc aacaccggca        60
aggaattacc ctgggttctc agtttttgac agagttccaa acccgataat cccggcagta       120
accaatccac aatggcaagg gtgtattccg tccattgatt ttccaaataa tcccaagctt       180
gggagccatc cgtcacccaa tccaccacat acttttcact aactagcact ttcttaatag       240
ccattcccaa atccgtctca tcttccacca gcaaaattcg catcgcctct gcctttttta       300
taacggtctg atcttagcgg gggaaggaga ttttcacctg aatttcatac cccctttggc       360
agactgggaa atcttggac aaattcccaa tttgaggtgg t                            401
```

<210> SEQ ID NO 23
<211> LENGTH: 1089
<212> TYPE: DNA
<213> ORGANISM: Artificial Sequence
<220> FEATURE:
<223> OTHER INFORMATION: Synthetic construct (Cc1 FatB1 gene, truncated, codon optimized for Synechocystis)

<400> SEQUENCE: 23

```
atggcgaacg gtagcgctgt ctctctgaag agcggctcct tgaatacgca agaggacact        60
tcttcttccc caccgccacg cgcgttcatc aaccaattac ccgactggtc catgttattg       120
acggcgatta ccactgtctt tgttgccgca gagaaacagt ggactatgtt agaccgcaag       180
agcaagcgct ccgatatgtt agtggattct tttggcatgg aacgcattgt gcaggatggc       240
ttagtgtttc gtcaatcttt tagcattcgt tcttatgaaa tcggtgcaga tcgtcgtgca       300
tccattgaaa ccttaatgaa ccatctgcag gaaactagct tgaatcattg caaatccatt       360
cgcttgttga tgagggttt tggtcgcacc cccgagatgt gcaaacgtga cttgatctgg       420
gtggttaccc gcatgcacat catggtcaac cgctacccta cctggggtga taccgttgag       480
attaacactt gggtttccca aagcggcaag aatggtatgg tcgtgattg gctgatttcc       540
gactgtaata ccggcgaaat cctgatccgc gcgacgtctg catgggcgat gatgaaccaa       600
aagacccgtc gtctgtctaa actgccttac gaagtcagcc aagagattgc tccgcacttc       660
gtcgacagcc ctcccgtgat cgaggacggc gaccgtaagt tacacaagtt cgatgtgaaa       720
accggcgaca gcatccgtaa aggtttgact ccgcgttgga tgacttaga tgttaatcag       780
cacgttaaca acgttaagta tcggctggg atcttagaga gcatgccgac cgaggtcttg       840
gaaactcatg aactgtgttt cttaactctg gagtatcgtc gcgagtgcgg tcgcgatagc       900
gtgctggaat ctgtgaccgc gatggatcct tctaatgaag gtggtcgctc ccactaccag       960
catttactgc gcttggagga cggtactgac atcgttaagg ccgcactgag gtggcgtcca      1020
aagaatgccc ggaatattgg tgccattagt accggtaaaa ccagtaatgg taatcccgcc      1080
agttaataa                                                              1089
```

<210> SEQ ID NO 24
<211> LENGTH: 361
<212> TYPE: PRT
<213> ORGANISM: Cuphea carthagenensis
<220> FEATURE:
<221> NAME/KEY: MISC_FEATURE
<223> OTHER INFORMATION: Cc1FatB1 thioesterase (N-terminally truncated)

<400> SEQUENCE: 24

```
Met Ala Asn Gly Ser Ala Val Ser Leu Lys Ser Gly Ser Leu Asn Thr
1               5                   10                  15
```

Gln Glu Asp Thr Ser Ser Pro Pro Arg Ala Phe Ile Asn Gln
            20                  25                  30

Leu Pro Asp Trp Ser Met Leu Leu Thr Ala Ile Thr Val Phe Val
        35                  40                  45

Ala Ala Glu Lys Gln Trp Thr Met Leu Asp Arg Lys Ser Lys Arg Ser
 50                  55                  60

Asp Met Leu Val Asp Ser Phe Gly Met Glu Arg Ile Val Gln Asp Gly
 65                  70                  75                  80

Leu Val Phe Arg Gln Ser Phe Ser Ile Arg Ser Tyr Glu Ile Gly Ala
                 85                  90                  95

Asp Arg Arg Ala Ser Ile Glu Thr Leu Met Asn His Leu Gln Glu Thr
                100                 105                 110

Ser Leu Asn His Cys Lys Ser Ile Arg Leu Leu Asn Glu Gly Phe Gly
            115                 120                 125

Arg Thr Pro Glu Met Cys Lys Arg Asp Leu Ile Trp Val Val Thr Arg
130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
                180                 185                 190

Ser Ala Trp Ala Met Met Asn Gln Lys Thr Arg Arg Leu Ser Lys Leu
            195                 200                 205

Pro Tyr Glu Val Ser Gln Glu Ile Ala Pro His Phe Val Asp Ser Pro
210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Asn Val Lys Tyr Ile Gly Trp Ile Leu
            260                 265                 270

Glu Ser Met Pro Thr Glu Val Leu Glu Thr His Glu Leu Cys Phe Leu
            275                 280                 285

Thr Leu Glu Tyr Arg Arg Glu Cys Gly Arg Asp Ser Val Leu Glu Ser
        290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
                325                 330                 335

Glu Trp Arg Pro Lys Asn Ala Arg Asn Ile Gly Ala Ile Ser Thr Gly
            340                 345                 350

Lys Thr Ser Asn Gly Asn Pro Ala Ser
            355                 360

<210> SEQ ID NO 25
<211> LENGTH: 90
<212> TYPE: DNA
<213> ORGANISM: Artificial Sequence
<220> FEATURE:
<223> OTHER INFORMATION: Synthetic construct (TrcY promoter)

<400> SEQUENCE: 25
ctgaaatgag ctgttgacaa ttaatcatcc ggctcgtata atgtgtggaa ttgtgagcgg    60

```
ataacaattt cacactaagg aggaaaaaaa                                    90
```

<210> SEQ ID NO 26
<211> LENGTH: 1404
<212> TYPE: DNA
<213> ORGANISM: Synechocystis PCC 6803
<220> FEATURE:
<221> NAME/KEY: misc_feature
<223> OTHER INFORMATION: Sll0141 MFP-175 gene

<400> SEQUENCE: 26

```
ctattttct gataaaacgc tgagacgaat ttgactatcc ggttgtagcg gtctactact     60
gcggaccaca aaacgttcct ggggagctaa gcctgccaca atttccacct tcccgttggc   120
agtttgcccc agggtaaccg atcgccgttc cagcacgtct ttttcccctg ctttggtcac   180
cacaaaaatg gcatcttcat cgacaatggc agattctgga actaccacat ggtatctgc    240
actggcatca aaactgaccc tggccaacag cccagcgcca atttttttcac caggattatc   300
catggttatt ccaccggca caaggcgaga attaacgtca gcctgggggg aaatgcgggt    360
taccacgccc gtaaaagtct ggccaggaaa cgcatctagc ttgacgttga ccttttgctg   420
tagggcaatt tgggccagtt gcaactccga tacctgcacg tcaatttcta actgacgaaa   480
atcccccagt tgcaaaattt ccgtccccgg ctgcactaaa ttgcctggtt cacttaatcg   540
tcgtaacacc cgccccggaa atggtgctct gacggtggcg tactgttgcc tagtttgggc   600
ctgttcaatg gaagctcgct gggcattcat ctgggcggtg gccgccccca ccctctgctg   660
ttcgatctgc acctgggcga tcgccgagtt gaggatttgg gacgcagttt tggccgctgt   720
tttagcttgg cttaattgtt ggctagcgct ggcctgttcg ttacgcaaaa tttccttggc   780
ttgacgggct ctggtttctg cctgttccgc ctgttgggca ccgccagctc cctcttcggc   840
taatagtcgg aagcgagcag catcggcctg ggtttgatct acttccagcc gggcttgttc   900
aatgcgggcg ttgagggaag tttccaaacg gataatgtcc gcctgggcct gttgcagttg   960
caaacgggcc tgttctaccc gaatttgggc atcccccacc tgactttggg cagttaaaac  1020
ttccgaacgt tgggccattt tctccgcttt ggcctggtct accgccccca gtaataaatc  1080
atcttcaatt tccgccaata tttcttctcc cctgaccga tcgccacat ccactggtag   1140
cctttgcagt cgtccttcaa tctgggcttt gatggaggct tcccgcactg gggctgtggt  1200
gcccgtatat tccaactcct tggtcaatgc ttggggtcga gctagggcca catccacggc  1260
gatcgcctgg tttgattcag tattctccgt ttgggctttg acattttgtt cccagagatc  1320
gctgcaaccc atcagggaaa aacttaataa acctagcagg gaaagttgcc gtcgcagacg  1380
ttggtggggg atgtacttgt tcat                                        1404
```

<210> SEQ ID NO 27
<211> LENGTH: 467
<212> TYPE: PRT
<213> ORGANISM: Synechocystis PCC 6803
<220> FEATURE:
<221> NAME/KEY: MISC_FEATURE
<223> OTHER INFORMATION: Sll0141 MFP-175 protein

<400> SEQUENCE: 27

```
Met Asn Lys Tyr Ile Pro His Gln Arg Leu Arg Arg Gln Leu Ser Leu
1               5                   10                  15

Leu Gly Leu Leu Ser Phe Ser Leu Met Gly Cys Ser Asp Leu Trp Glu
            20                  25                  30

Gln Asn Val Lys Ala Gln Thr Glu Asn Thr Glu Ser Asn Gln Ala Ile
```

```
                35                  40                  45
Ala Val Asp Val Ala Leu Ala Arg Pro Gln Ala Leu Thr Lys Glu Leu
 50                  55                  60
Glu Tyr Thr Gly Thr Thr Ala Pro Val Arg Glu Ala Ser Ile Lys Ala
 65                  70                  75                  80
Gln Ile Glu Gly Arg Leu Gln Arg Leu Pro Val Asp Val Gly Asp Arg
                 85                  90                  95
Val Arg Gly Glu Glu Ile Leu Ala Glu Ile Asp Asp Leu Leu Leu
                100                 105                 110
Gly Ala Val Asp Gln Ala Lys Ala Glu Lys Met Ala Gln Arg Ser Glu
                115                 120                 125
Val Leu Thr Ala Gln Ser Gln Val Gly Asp Ala Gln Ile Arg Val Glu
        130                 135                 140
Gln Ala Arg Leu Gln Leu Gln Gln Ala Gln Ala Asp Ile Ile Arg Leu
145                 150                 155                 160
Glu Thr Ser Leu Asn Ala Arg Ile Glu Gln Ala Arg Leu Glu Val Asp
                165                 170                 175
Gln Thr Gln Ala Asp Ala Ala Arg Phe Arg Leu Leu Ala Glu Glu Gly
                180                 185                 190
Ala Gly Gly Ala Gln Gln Ala Glu Gln Ala Glu Thr Arg Ala Arg Gln
        195                 200                 205
Ala Lys Glu Ile Leu Arg Asn Glu Gln Ala Ser Ala Ser Gln Gln Leu
210                 215                 220
Ser Gln Ala Lys Thr Ala Ala Lys Thr Ala Ser Gln Ile Leu Asn Ser
225                 230                 235                 240
Ala Ile Ala Gln Val Gln Ile Glu Gln Arg Val Gly Ala Ala Thr
                245                 250                 255
Ala Gln Met Asn Ala Gln Arg Ala Ser Ile Glu Gln Ala Gln Thr Arg
                260                 265                 270
Gln Gln Tyr Ala Thr Val Arg Ala Pro Phe Pro Gly Arg Val Leu Arg
        275                 280                 285
Arg Leu Ser Glu Pro Gly Asn Leu Val Gln Pro Gly Thr Glu Ile Leu
290                 295                 300
Gln Leu Gly Asp Phe Arg Gln Leu Glu Ile Asp Val Gln Val Ser Glu
305                 310                 315                 320
Leu Gln Leu Ala Gln Ile Ala Leu Gln Gln Lys Val Asn Val Lys Leu
                325                 330                 335
Asp Ala Phe Pro Gly Gln Thr Phe Thr Gly Val Val Thr Arg Ile Ser
                340                 345                 350
Pro Gln Ala Asp Val Asn Ser Arg Leu Val Pro Val Glu Ile Thr Met
        355                 360                 365
Asp Asn Pro Gly Glu Lys Ile Gly Ala Gly Leu Leu Ala Arg Val Ser
        370                 375                 380
Phe Asp Ala Ser Ala Asp Thr Asn Val Val Pro Glu Ser Ala Ile
385                 390                 395                 400
Val Asp Glu Asp Ala Ile Phe Val Val Thr Lys Ala Gly Glu Lys Asp
                405                 410                 415
Val Leu Glu Arg Arg Ser Val Thr Leu Gly Gln Thr Ala Asn Gly Lys
        420                 425                 430
Val Glu Ile Val Ala Gly Leu Ala Pro Gln Glu Arg Phe Val Val Arg
        435                 440                 445
Ser Ser Arg Pro Leu Gln Pro Asp Ser Gln Ile Arg Leu Ser Val Leu
450                 455                 460
```

Ser Glu Lys
465

<210> SEQ ID NO 28
<211> LENGTH: 3228
<212> TYPE: DNA
<213> ORGANISM: Synechocystis PCC 6803
<220> FEATURE:
<221> NAME/KEY: misc_feature
<223> OTHER INFORMATION: Sll0142 IMP-174 gene

<400> SEQUENCE: 28

| | | | | | |
|---|---|---|---|---|---|
| ttattggatt | tttgttggta | catcttcttc | ggttaagcgg | gattccaaat | cggttttgac | 60 |
| tttttctata | tcaaccccTT | cccattggtg | tagcaacacg | tacaagcagg | gaattaaaaa | 120 |
| tagggttagt | aaggtagcga | gggaaagacc | ggaaaacacc | acaatgccca | aaggttggag | 180 |
| caattctgat | ccttgtccaa | tgcccagggc | gaggggaaac | atgcccagca | cggtggtaat | 240 |
| ggtggtcatc | aaaatcggtc | gtaagcgttg | ggggctgcc | cgtaagatag | ctgcttctcg | 300 |
| actgatgcct | tcttcggccc | agatttggtt | agctaactcc | accatgatga | tggcgttgtt | 360 |
| gaccacaatc | cccaccagga | gtactgtacc | aacaattacc | gtggcaccga | tcgccgtttg | 420 |
| ggtaacgtat | aaacccaaaa | tgcctccagc | caaagccaaa | ggtagggtga | acataattac | 480 |
| cagaggatcg | aggagagaat | tgtattgcac | cgccataacc | acaaagacga | gaaacgccgc | 540 |
| caagccccct | aaaatcacca | gggaagactg | taactgttca | ttgctcgccg | ccgctgtact | 600 |
| gggcagtcga | gacaccccgg | ggggaaactc | catggcggat | aaaacttggt | caacttctgt | 660 |
| gagagcttca | ctcaaactag | ccccttccac | taacgtacca | gcaattaaaa | acaccggccg | 720 |
| ttggttaatg | cgttgaattt | ccccccggtgc | ccgaccttgg | tcaatggtgg | ccacatcccc | 780 |
| caaacggatc | gggcgatcgc | catcaataaa | gaggggaatt | tgtgccaaat | ccccagggcc | 840 |
| agagagcaaa | tcattgtcca | atttcactcg | cacatccacc | aggcgatttt | cccgttgcaa | 900 |
| ctgggtgggc | acagcaccgt | ctaaagcagt | ttggactgtc | tgcccaatgg | cttgggtggt | 960 |
| taaacctaat | tccgtcgccc | tttgccaatc | gggacgaatc | tgcacttccg | gttgacgggg | 1020 |
| atcggcatcg | ggacgaaaac | gggccaatgt | aactttttct | cctaattccg | ccaacactgc | 1080 |
| ccgcccccgct | tcatctaaca | catcggcatc | attcccctgc | aaaaccacat | ccacatctac | 1140 |
| gttacgtagg | ggggaattgc | ttaaaatcag | accccgcaac | tgtcccggtg | ccatccgcag | 1200 |
| acgaatatcc | accaagttca | gcgcttccaa | ttccgccgtc | acccgttcgg | tgaatgcctc | 1260 |
| cacatcggta | ttgggtttta | gggtaatggt | gctggaactg | cgcagagcat | tagcattaac | 1320 |
| gttactgcca | aagagaaacc | ccccccaccgt | ggtgaaagcg | tattcggttt | ccggctgatt | 1380 |
| gatgaggatg | tcatccacga | tcgccattaa | gcgttggttt | tcctctaagg | gagtgccggg | 1440 |
| ggggaactgg | gcaaacatac | tggcttgacc | cgtattgatg | cggggcaaaa | tttcctgggg | 1500 |
| aatctgtccg | atcatccaca | aactactgcc | accaaaaaca | atgaaaatag | aagccaccgc | 1560 |
| caccaatcga | tgtcggatca | ggatggataa | aaaacgggcg | taggccgccg | tggcccctgc | 1620 |
| aaaacgtcgg | ttaaattccc | gaaaaaataa | ccaattaccc | aaaccactcc | ggcggcgaat | 1680 |
| ggccaataaa | cgggaagcgg | ccatgggcac | tagggtcact | gccaccagga | tggaagccgc | 1740 |
| caccgcaaaa | ctgatggtca | aaattaattc | attaaaaatc | agggcaatga | agccaccaat | 1800 |
| catcaaaaat | ggcaataccg | ccaccaagtt | agtgctagtg | gaagccacca | gtgccgattc | 1860 |
| caccgtttga | ctactggcga | tcgcctggtt | gcgcatttcc | cctttagtta | gtgggagggg | 1920 |

```
attaactttg ccggggtca tgcccgcccc ttccgcaatg gtttccaaca tgacgatgga    1980
gttatccacc acaatgccca ccccagggc caagcccccc aaactaaaaa cgttcaagga    2040
taaaccaaag gccttcatga caatgatggc cgccatggtg gccaagggaa tagccaacac    2100
aataattaac gtctgtcgca agaaccgag aaataacaaa acggcgatcg ccgccaggac    2160
cgtaccaatt aaccccgaaa caacaacgtt attgaccgag ttacggataa aaactgaatc    2220
atctaaggta ggggttaatt ccgccgcctg gggaataatg ccttctgtgc gtaactcctc    2280
caaacgtttt ttaaccccat ccactacttc aatggtgtta gcctccggtt gtttctgcac    2340
actcactttt accgccggat taccgttgag ggtcacaaaa atccgttctt cctctgtacc    2400
gtcaataaca gtggccacat cccgcagata aacttttttgg gccgattgat cctccagacc    2460
agacactgtg cccaccacta aatcctcaat ttcctgggct gaagcaaatc tacccactgt    2520
acgggttaaa ggttccgact ccgtaccaac aattctgccc ccggaaatat ccacatttcg    2580
gctctgtaaa gcatccaata cctgggtcaa actcaccccc gaccgctgta gtcgttgtaa    2640
atccacattg atccggactt cttcctgggc tgccccgac acattcaccg atgccacccc    2700
cggcaccact cccaattccc gtgctaactc ctcttctgca aatacccgca acgatggccc    2760
cgacaactcc ggggaggtaa cggcaaattc atacaccggc aactgggaag gatcaaactt    2820
aaataaccgg ggggtttcca gatcatccgg caactggttg cgggcccggt taaaggtagc    2880
ggtggcgtca ttcaacgctt ggtcaatatt gcccccggc tcgaaaaaca aatccaggct    2940
aatttgcccc tccctggttt gagagtaaac ctgcaccacc ccttccgtgg ctgacagggc    3000
cgcttccaag ggtctggtaa tttcgtccac cgccacttcc ggagataccc ctggagcatc    3060
tagtcgcacg ccaatgcggg gataggtgat ggaaggcaac agatccaccg gcagggaaaa    3120
aacagcgaaa accccaaca caataatggc cagggtgagc ataagggtgg caatgtgccg    3180
acggatggcc aggccactca gactaaaaac ggagttgggg gaggacat              3228
```

<210> SEQ ID NO 29
<211> LENGTH: 1075
<212> TYPE: PRT
<213> ORGANISM: Synechocystis PCC 6803
<220> FEATURE:
<221> NAME/KEY: MISC_FEATURE
<223> OTHER INFORMATION: Sll0142 IMP-174 protein

<400> SEQUENCE: 29

```
Met Ser Ser Pro Asn Ser Val Phe Ser Leu Ser Gly Leu Ala Ile Arg
1               5                   10                  15

Arg His Ile Ala Thr Leu Met Leu Thr Leu Ala Ile Ile Val Leu Gly
            20                  25                  30

Val Phe Ala Val Phe Ser Leu Pro Val Asp Leu Leu Pro Ser Ile Thr
        35                  40                  45

Tyr Pro Arg Ile Gly Val Arg Leu Asp Ala Pro Gly Val Ser Pro Glu
    50                  55                  60

Val Ala Val Asp Glu Ile Thr Arg Pro Leu Glu Ala Ala Leu Ser Ala
65                  70                  75                  80

Thr Glu Gly Val Val Gln Val Tyr Ser Gln Thr Arg Glu Gly Gln Ile
                85                  90                  95

Ser Leu Asp Leu Phe Phe Glu Pro Gly Gly Asn Ile Asp Gln Ala Leu
            100                 105                 110

Asn Asp Ala Thr Ala Thr Phe Asn Arg Ala Arg Asn Gln Leu Pro Asp
        115                 120                 125
```

```
Asp Leu Glu Thr Pro Arg Leu Phe Lys Phe Asp Pro Ser Gln Leu Pro
    130                 135                 140
Val Tyr Glu Phe Ala Val Thr Ser Pro Glu Leu Ser Gly Pro Ser Leu
145                 150                 155                 160
Arg Val Phe Ala Glu Glu Leu Ala Arg Glu Leu Gly Val Val Pro
                165                 170                 175
Gly Val Ala Ser Val Asn Val Ser Gly Ala Ala Gln Glu Glu Val Arg
            180                 185                 190
Ile Asn Val Asp Leu Gln Arg Leu Gln Arg Ser Gly Val Ser Leu Thr
        195                 200                 205
Gln Val Leu Asp Ala Leu Gln Ser Arg Asn Val Asp Ile Ser Gly Gly
210                 215                 220
Arg Ile Val Gly Thr Glu Ser Glu Pro Leu Thr Arg Thr Val Gly Arg
225                 230                 235                 240
Phe Ala Ser Ala Gln Glu Ile Glu Asp Leu Val Val Gly Thr Val Ser
                245                 250                 255
Gly Leu Glu Asp Gln Ser Ala Gln Lys Val Tyr Leu Arg Asp Val Ala
            260                 265                 270
Thr Val Ile Asp Gly Thr Glu Glu Arg Ile Phe Val Thr Leu Asn
        275                 280                 285
Gly Asn Pro Ala Val Lys Val Ser Val Gln Lys Gln Pro Glu Ala Asn
290                 295                 300
Thr Ile Glu Val Val Asp Gly Val Lys Lys Arg Leu Glu Glu Leu Arg
305                 310                 315                 320
Thr Glu Gly Ile Ile Pro Gln Ala Ala Glu Leu Thr Pro Thr Leu Asp
                325                 330                 335
Asp Ser Val Phe Ile Arg Asn Ser Val Asn Asn Val Val Ser Gly
            340                 345                 350
Leu Ile Gly Thr Val Leu Ala Ala Ile Ala Val Leu Leu Phe Leu Gly
        355                 360                 365
Ser Leu Arg Gln Thr Leu Ile Ile Val Leu Ala Ile Pro Leu Ala Thr
370                 375                 380
Met Ala Ala Ile Ile Val Met Lys Ala Phe Gly Leu Ser Leu Asn Val
385                 390                 395                 400
Phe Ser Leu Gly Gly Leu Ala Leu Gly Val Gly Ile Val Val Asp Asn
                405                 410                 415
Ser Ile Val Met Leu Glu Thr Ile Ala Glu Gly Ala Gly Met Thr Pro
            420                 425                 430
Gly Lys Val Asn Pro Leu Pro Leu Thr Lys Gly Glu Met Arg Asn Gln
        435                 440                 445
Ala Ile Ala Ser Ser Gln Thr Val Glu Ser Ala Leu Val Ala Ser Thr
450                 455                 460
Ser Thr Asn Leu Val Ala Val Leu Pro Phe Leu Met Ile Gly Gly Phe
465                 470                 475                 480
Ile Ala Leu Ile Phe Asn Glu Leu Ile Leu Thr Ile Ser Phe Ala Val
                485                 490                 495
Ala Ala Ser Ile Leu Val Ala Val Thr Leu Val Pro Met Ala Ala Ser
            500                 505                 510
Arg Leu Leu Ala Ile Arg Arg Ser Gly Leu Gly Asn Trp Leu Phe
        515                 520                 525
Phe Arg Glu Phe Asn Arg Arg Phe Ala Gly Ala Thr Ala Ala Tyr Ala
530                 535                 540
Arg Phe Leu Ser Ile Leu Ile Arg His Arg Leu Val Ala Val Ala Ser
```

```
545                 550                 555                 560

Ile Phe Ile Val Phe Gly Gly Ser Ser Leu Trp Met Ile Gly Gln Ile
                565                 570                 575

Pro Gln Glu Ile Leu Pro Arg Ile Asn Thr Gly Gln Ala Ser Met Phe
                580                 585                 590

Ala Gln Phe Pro Pro Gly Thr Pro Leu Glu Glu Asn Gln Arg Leu Met
                595                 600                 605

Ala Ile Val Asp Asp Ile Leu Ile Asn Gln Pro Glu Thr Glu Tyr Ala
610                 615                 620

Phe Thr Thr Val Gly Gly Phe Leu Phe Gly Ser Asn Val Asn Ala Asn
625                 630                 635                 640

Ala Leu Arg Ser Ser Ser Thr Ile Thr Leu Lys Pro Asn Thr Asp Val
                645                 650                 655

Glu Ala Phe Thr Glu Arg Val Thr Ala Glu Leu Glu Ala Leu Asn Leu
                660                 665                 670

Val Asp Ile Arg Leu Arg Met Ala Pro Gly Gln Leu Arg Gly Leu Ile
                675                 680                 685

Leu Ser Asn Ser Pro Leu Arg Asn Val Asp Val Asp Val Val Leu Gln
690                 695                 700

Gly Asn Asp Ala Asp Val Leu Asp Glu Ala Gly Arg Ala Val Leu Ala
705                 710                 715                 720

Glu Leu Gly Glu Lys Val Thr Leu Ala Arg Phe Arg Pro Asp Ala Asp
                725                 730                 735

Pro Arg Gln Pro Glu Val Gln Ile Arg Pro Asp Trp Gln Arg Ala Thr
                740                 745                 750

Glu Leu Gly Leu Thr Thr Gln Ala Ile Gly Gln Thr Val Gln Thr Ala
                755                 760                 765

Leu Asp Gly Ala Val Pro Thr Gln Leu Gln Arg Glu Asn Arg Leu Val
770                 775                 780

Asp Val Arg Val Lys Leu Asp Asn Asp Leu Leu Ser Gly Pro Gly Asp
785                 790                 795                 800

Leu Ala Gln Ile Pro Leu Phe Ile Asp Gly Asp Arg Pro Ile Arg Leu
                805                 810                 815

Gly Asp Val Ala Thr Ile Asp Gln Gly Arg Ala Pro Gly Glu Ile Gln
                820                 825                 830

Arg Ile Asn Gln Arg Pro Val Phe Leu Ile Ala Gly Thr Leu Val Glu
                835                 840                 845

Gly Ala Ser Leu Ser Glu Ala Leu Thr Glu Val Asp Gln Val Leu Ser
850                 855                 860

Ala Met Glu Phe Pro Pro Gly Val Ser Arg Leu Pro Ser Thr Ala Ala
865                 870                 875                 880

Ala Ser Asn Glu Gln Leu Gln Ser Ser Leu Val Ile Leu Gly Gly Leu
                885                 890                 895

Ala Ala Phe Leu Val Phe Val Val Met Ala Val Gln Tyr Asn Ser Leu
                900                 905                 910

Leu Asp Pro Leu Val Ile Met Phe Thr Leu Pro Leu Ala Leu Ala Gly
                915                 920                 925

Gly Ile Leu Gly Leu Tyr Val Thr Gln Thr Ala Ile Gly Ala Thr Val
                930                 935                 940

Ile Val Gly Thr Val Leu Leu Val Gly Ile Val Val Asn Asn Ala Ile
945                 950                 955                 960

Ile Met Val Glu Leu Ala Asn Gln Ile Trp Ala Glu Glu Gly Ile Ser
                965                 970                 975
```

```
Arg Glu Ala Ala Ile Leu Arg Ala Ala Pro Gln Arg Leu Arg Pro Ile
            980                 985                 990

Leu Met Thr Thr Ile Thr Thr Val Leu Gly Met Phe Pro Leu Ala Leu
            995                 1000                1005

Gly Ile Gly Gln Gly Ser Glu Leu Leu Gln Pro Leu Gly Ile Val
        1010                1015                1020

Val Phe Ser Gly Leu Ser Leu Ala Thr Leu Leu Thr Leu Phe Leu
    1025                1030                1035

Ile Pro Cys Leu Tyr Val Leu Leu His Gln Trp Glu Gly Val Asp
        1040                1045                1050

Ile Glu Lys Val Lys Thr Asp Leu Glu Ser Arg Leu Thr Glu Glu
        1055                1060                1065

Asp Val Pro Thr Lys Ile Gln
        1070            1075

<210> SEQ ID NO 30
<211> LENGTH: 1792
<212> TYPE: DNA
<213> ORGANISM: Artificial Sequence
<220> FEATURE:
<223> OTHER INFORMATION: Synthetic construct (CAT cassette integration
      construct)

<400> SEQUENCE: 30
ggctgacgtt aattctcgcc ttgtgccggt ggaaataacc atggataatc ctggtgaaaa     60
aattggcgct gggctgttgg ccagggtcag ttttgatgcc agtgcagata ccaatgtggt    120
agttccagaa tctgccattg tcgatgaaga tgccattttt gtggtgacca agcagggga    180 aaaagacgtg ctggaacggc gatcggttac cctggggcaa actgccaacg ggaaggtgga    240
aattgtggca ggcttagctc cccaggaacg ttttgtggtc cgcagtagta gaccgctaca    300
accggatagt caaattcgtc tcagcgtttt atcagaaaaa tagcaggaac aatagtgtta    360
atggagactg ttaagttttt gttcgtttta gctccactgg aactgttcaa ataaatcgat    420
taaacctctc cgacattttc ccagtcaaaa gactcgaatc ctcgaaccat tgaaattttt    480 ccttcccca ggaattattg aagctttggc gaaaatgaga cgttgatcgg cacgtaagag    540
gttccaactt tcaccataat gaaataagat cactaccggg cgtatttttt gagttatcga    600
gattttcagg agctaaggaa gctaaaatgg agaaaaaaat cactggatat accaccgttg    660
atatatccca tggcatcgt aaagaacatt ttgaggcatt tcagtcagtt gctcaatgta    720
cctataacca gaccgttcag ctggatatta cggccttttt aaagaccgta agaaaaata    780 agcacaagtt ttatccggcc tttattcaca ttcttgcccg cctgatgaat gctcatccgg    840
aattccgtat ggcaatgaaa gacggtgagc tggtgatatg ggatagtgtt caccttgtt    900 acaccgtttt ccatgagcaa actgaaacgt tttcatcgct ctggagtgaa taccacgacg    960
atttccggca gttctacac atatattcgc aagatgtggc gtgttacggt gaaaacctgg   1020
cctatttccc taaagggttt attgagaata tgttttcgt ctcagccaat ccctgggtga   1080
gtttcaccag ttttgattta aacgtggcca atatggacaa cttcttcgcc ccgttttca   1140 ccatgggcaa atattatacg caaggcgaca aggtgctgat gccgctggcg attcaggttc   1200
atcatgccgt ctgtgatggc ttccatgtcg gcagaatgct taatgaatta caacagtact   1260
gcgatgagtg gcaggcggg gcgtaaggat ccacctcctc tgttcccat ccccccagcc    1320 cctatgtcct ccccccaactc cgttttagt ctgagtggcc tggccatccg tcggcacatt   1380
```

```
gccacccttc tgctcaccct ggccattatt gtgttggggg ttttcgctgt ttttccctg      1440 ccggtggatc tgttgccttc catcacctat ccccgcattg gcgtgcgact agatgctcca     1500
ggggtatctc cggaagtggc ggtggacgaa attaccagac ccttggaagc ggccctgtca     1560
gccacggaag gggtggtgca ggtttactct caaaccaggg aggggcaaat tagcctggat     1620
ttgtttttcg agccgggggg caatattgac caagcgttga atgacgccac cgctacctt     1680 aaccgggccc gcaaccagtt gccggatgat ctggaaaccc cccggttatt taagtttgat    1740
ccttcccagt tgccggtgta tgaatttgcc gttacctccc cggagttgtc gg            1792

<210> SEQ ID NO 31
<211> LENGTH: 126
<212> TYPE: DNA
<213> ORGANISM: Escherichia coli
<220> FEATURE:
<221> NAME/KEY: misc_feature
<223> OTHER INFORMATION: CAT promoter

<400> SEQUENCE: 31
aagctttggc gaaaatgaga cgttgatcgg cacgtaagag gttccaactt tcaccataat     60
gaaataagat cactaccggg cgtattttt gagttatcga gattttcagg agctaaggaa     120
gctaaa                                                                126

<210> SEQ ID NO 32
<211> LENGTH: 657
<212> TYPE: DNA
<213> ORGANISM: Escherichia coli
<220> FEATURE:
<221> NAME/KEY: misc_feature
<223> OTHER INFORMATION: Chloramphenicol acetyl transferase gene

<400> SEQUENCE: 32
atggagaaaa aaatcactgg atataccacc gttgatatat cccaatggca tcgtaaagaa     60
cattttgagg catttcagtc agttgctcaa tgtacctata accagaccgt tcagctggat    120
attacggcct ttttaaagac cgtaaagaaa aataagcaca gttttatcc ggcctttatt     180 cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
gccaatatgg acaacttctt cgccccgtt ttcaccatgg gcaaatatta tacgcaaggc    540
gacaaggtgc tgatgccgct ggcgattcag gttcatcatg ccgtctgtga tggcttccat    600
gtcggcagaa tgcttaatga attacaacag tactgcgatg agtggcaggg cggggcg       657

<210> SEQ ID NO 33
<211> LENGTH: 500
<212> TYPE: DNA
<213> ORGANISM: Synechocystis PCC 6803
<220> FEATURE:
<221> NAME/KEY: misc_feature
<223> OTHER INFORMATION: Genomic sequence upstream of sll0142

<400> SEQUENCE: 33
ggctgacgtt aattctcgcc ttgtgccggt ggaaataacc atggataatc ctggtgaaaa     60
aattggcgct gggctgttgg ccagggtcag ttttgatgcc agtgcagata ccaatgtggt    120
```

```
agttccagaa tctgccattg tcgatgaaga tgccattttt gtggtgacca aagcagggga    180
aaaagacgtg ctggaacggc gatcggttac cctggggcaa actgccaacg ggaaggtgga    240
aattgtggca ggcttagctc cccaggaacg ttttgtggtc cgcagtagta gaccgctaca    300
accggatagt caaattcgtc tcagcgtttt atcagaaaaa tagcaggaac aatagtgtta    360
atggagactg ttaagttttt gttcgtttta gctccactgg aactgttcaa ataaatcgat    420
taaacctctc cgacattttc ccagtcaaaa gactcgaatc ctcgaaccat tgaaattttt    480 cctttccca ggaattattg                                                500
```

<210> SEQ ID NO 34
<211> LENGTH: 499
<212> TYPE: DNA
<213> ORGANISM: Synechocystis PCC 6803
<220> FEATURE:
<221> NAME/KEY: misc_feature
<223> OTHER INFORMATION: Genomic sequence downstream of sll0142

<400> SEQUENCE: 34

```
cctcctctgt tccccatccc cccagccct atgtcctccc ccaactccgt ttttagtctg     60
agtggcctgg ccatccgtcg gcacattgcc acccttatgc tcaccctggc cattattgtg    120
ttgggggttt tcgctgtttt ttccctgccg gtggatctgt tgccttccat cacctatccc    180
cgcattggcg tgcgactaga tgctccaggg gtatctccgg aagtggcggt ggacgaaatt    240
accagaccct tggaagcggc cctgtcagcc acggaagggg tggtgcaggt ttactctcaa    300
accagggagg ggcaaattag cctggatttg ttttcgagc cggggggcaa tattgaccaa    360
gcgttgaatg acgccaccgc tacctttaac cgggcccgca accagttgcc ggatgatctg    420 gaaaccccc ggttatttaa gtttgatcct tcccagttgc cggtgtatga atttgccgtt    480
acctccccgg agttgtcgg                                                499
```

<210> SEQ ID NO 35
<211> LENGTH: 526
<212> TYPE: PRT
<213> ORGANISM: Synechocystis PCC 6803
<220> FEATURE:
<221> NAME/KEY: MISC_FEATURE
<223> OTHER INFORMATION: TolC

<400> SEQUENCE: 35

Met Lys Ser Ile His Pro Leu Lys Phe Trp Ser Ser Thr Leu Leu
1               5                   10                  15

Leu Leu Leu Ser Thr Ser Val Gly Val Phe Leu Pro Gly Phe Ser Gly
            20                  25                  30

Gly Gln Gly Ala Ile Ala Val Ala Gln Ser Val Ser Pro Pro Asp Asn
        35                  40                  45

Ala Pro Ser Ala Glu Thr Gly Asn Asn Ala Asp Asp Ser Gly Phe Pro
    50                  55                  60

Leu Pro Gln Leu Pro Asp Thr Ala Pro Asn Glu Arg Leu Asn Pro Ser
65                  70                  75                  80

Gly Asn Pro Leu Met Phe Pro Thr Lys Pro Asp Glu Val Asp Thr Thr
                85                  90                  95

Val Arg Gln Ala Ile Thr Leu Asp Glu Ala Ile Asp Leu Ala Leu Arg
            100                 105                 110

Asn Asn Glu Gln Leu Gln Gln Ala Lys Leu Ser Leu Glu Gln Gln Glu
        115                 120                 125

Ala Gly Leu Met Ala Ala Arg Ala Ala Leu Phe Pro Ser Leu Asp Thr

```
                130                 135                 140
Asp Phe Thr Phe Ser Arg Asp Ser Ala Ala Ala Glu Ala Thr Asn
145                 150                 155                 160

Ala Leu Ile Ala Asn Gln Asn Gln Thr Thr Thr Val Asn Pro Glu Leu
                165                 170                 175

Arg Ser Glu Thr Ser Thr Asn Ala Val Gly Asn Ile Asn Leu Thr Tyr
                180                 185                 190

Ser Ile Tyr Ala Gly Gly Glu Arg Ser Ala Gln Ile Ala Lys Ala Glu
                195                 200                 205

Gln Leu Val Gln Asn Ser Arg Leu Gln Val Glu Val Ala Glu Gln
210                 215                 220

Thr Arg Phe Glu Ala Thr Asp Arg Tyr Tyr Ala Leu Gln Gly Ala Asp
225                 230                 235                 240

Ala Gln Val Ala Ile Ala Gln Ala Ser Val Glu Asp Ala Ser Gln Ser
                245                 250                 255

Leu Arg Asp Ala Arg Leu Leu Glu Gln Ala Gly Leu Gly Thr Arg Phe
                260                 265                 270

Asp Val Leu Arg Ala Glu Gly Asp Leu Ala Thr Ala Asn Glu Ala Leu
                275                 280                 285

Thr Arg Ser Ile Ala Asp Gln Arg Asn Ala Arg Arg Leu Ala Gln
290                 295                 300

Leu Leu Ser Val Gly Gln Arg Val Glu Leu Thr Ala Ala Asp Glu Ile
305                 310                 315                 320

Val Glu Ala Gly Asp Trp Ser Leu Pro Leu Asp Glu Ser Ile Val Gln
                325                 330                 335

Ala Tyr Lys Asn Arg Ala Glu Leu Glu Gln Gln Leu Val Gln Ile Glu
                340                 345                 350

Val Ser Glu Gln Asp Arg Tyr Ile Ala Leu Ala Ala Ile Lys Pro Arg
                355                 360                 365

Val Asp Phe Leu Ala Asn Tyr Thr Tyr Gln Asn Asn Phe Asp Ser Ser
                370                 375                 380

Ala Gly Leu Val Asp Gly Tyr Ala Phe Ala Ala Arg Val Arg Trp Asn
385                 390                 395                 400

Phe Phe Asp Gly Gly Arg Ala Phe Ala Glu Ala Arg Ala Asp Arg
                405                 410                 415

Gln Met Asp Ile Ala Lys Thr Ala Phe Ser Glu Gln Arg Asn Gln Ile
                420                 425                 430

Arg Leu Glu Val Glu Glu Ser Tyr Tyr Thr Leu Ile Ser Asn Lys Glu
                435                 440                 445

Asn Ile Gly Ser Thr Arg Thr Asn Val Ile Arg Phe Glu Glu Ala Leu
                450                 455                 460

Arg Leu Ala Arg Leu Arg Phe Gln Ala Gly Val Gly Thr Gln Thr Asp
465                 470                 475                 480

Val Ile Asn Ala Gln Arg Asp Leu Ala Asn Ala Arg Gly Arg Phe Leu
                485                 490                 495

Gln Ala Ile Ile Gly Tyr Asn Gln Ser Leu Asn Gln Leu Gln Arg Ser
                500                 505                 510

Ile Ser Asn Leu Pro Asn Asn His Leu Phe Asp Ile Gln Pro
                515                 520                 525

<210> SEQ ID NO 36
<211> LENGTH: 2149
<212> TYPE: DNA
<213> ORGANISM: Pseudomonas fluorescens
```

<220> FEATURE:
<221> NAME/KEY: misc_feature
<223> OTHER INFORMATION: Genomic fragment

<400> SEQUENCE: 36

```
cgtgtggaag cacttcgaat tgctgggcct gtacgaaatc atcccaggct tcatcttcgc      60
cagcctggcg atctacttcg tgagcaagat gggcgcaccg acggtgggta tggtcgagcg     120
ttttgacgcg gcggaaaaag attacaactt gaacaagtaa ttcgctgggc gtttaacgcc     180
tgctgagcga acaagaaagg cccacgtccg aaggacgctg ggcctttttt tgctgggctg     240
attggtgcaa tagccgccga tgcccgtgga ttccagcggt gctcacgtag gaccttactt     300
atttgccgag gcagcgctcg gccaggcgaa cggctggtgc agaatcggcc gcccacccct     360
cgcagagaaa caccggatgt tcgctcctgc caatcaaagt gcctttaccc tgtccctcga     420
cggtgagctc agtgaactca aggtgttcga gtttacgggc cgtgaatcca tcagccagcc     480
ttaccatttt gatctcgagt tggtcagcga acagcccgat ctcgacctgg aaggcttgct     540
gcatcgccag gtgtacttgg gcttcgatga tcagggccat ggtgttcatg ggctggtcta     600
ccgggtggcg cagggcgatt ccggacggcg cctgacgcgt tatcagttga cgcttgtgcc     660
gcagctggcc tatctggcgc acagcagcca ccagcgcatt ttccagcaca agacggtgcc     720
gcagattgtt gcgcaggtac tggaggggca gggcatccag agtgaccgct tcgaattccg     780
gctcagcggt gcctaccccg agcgcgagta ttgtgtgcag tttggcgaga ctgacctggc     840
gttcattcag cggctgtgcg cggagttggg cattcactat cacttccagc attcggccga     900
ggggcatttg ctggtgtttg gggatgacca acggtctttt gcccagcccg aacagcccac     960
gccttacacc cccggttccg ggatggtggc ggatacccccg gcaatcaagc ggtttgcggt    1020
gcaggtgcag acccgcacca cggctgtgaa cctgcgcgat tacgactttc gcaagccgaa    1080
cctgggcctg gaaagcgcgg tcgctggcga gcagcttccg atgcttgaaa cgcaggatta    1140
ccccggtcat ttcagcgacc gcgcccatgg caaataccct tgcgcagcgag gcctggagcg    1200
tcatcgcagt gattaccgca tcgcccatgg caacggtgat gagccggcat tggccggcgg    1260
caggttcctc aggctggcgg gccacccacg gggagactgg aatggcctgt ggttggcgac    1320
acacgtgacc cacgagggta acaaccgcaa agtcctggaa gaggctgtga ccgaggtcgc    1380
cggtggggac tttcgccagg gttatcgcaa caactttatt gccgcgccgt gggacgtgat    1440
tttccgcccg ctctggacag agcatgcgcg cccagtgatc tcgggttatc aacatgccgt    1500
ggtgaccggc cccgccgaca gtgaaatcca ttgcgatgag tacggccggg tcaaggtgca    1560
actggcctgg gaccgtgccg gtgaacataa cgaccattcc agttgctggc tgagggttgc    1620
cagtgggtgg gcgcatgatc gctatggttc ggtgctgatc ccgcgagtcg gcatggaagt    1680
gctggtgggt ttcgtcaatg gcgacatgga catgccgttg gtgatgggct gtttgcccaa    1740
cgcggcgacg ccaggtgccc ctcgacctgc cggcggacaa gacccgcagt atcttgcgca    1800
gccagagcag cccgggcggc ggtggctaca acgagctacg tatcgaggac cgcaagggcg    1860
ccgaggaaat ttacctgcgc gcccagcggg attggacgca gcatgtactg catgatcaac    1920
aggtgcaggt cgataacggg cgtcgtatgc aggtgggtgg cgagtcgcac catgagttgc    1980
gcggtgaaga gcagcgcatt acccacggca atcgtctgac gcagctcaag caggatgatc    2040
acgtggtggt cgccggttcg cagcacatgc gtgccgggcg gactattgcg ttaggggccg    2100
ggcaaaacat cgtcattgat gcgggcgcga ctgtgacgat ccaggcggg                2149
```

```
<210> SEQ ID NO 37
<211> LENGTH: 512
<212> TYPE: PRT
<213> ORGANISM: Artificial Sequence
<220> FEATURE:
<223> OTHER INFORMATION: Synthetic construct (Truncated VgrG protein )

<400> SEQUENCE: 37
```

Met Phe Ala Pro Ala Asn Gln Ser Ala Phe Thr Leu Ser Leu Asp Gly
1               5                   10                  15

Glu Leu Ser Glu Leu Lys Val Phe Glu Phe Thr Gly Arg Glu Ser Ile
            20                  25                  30

Ser Gln Pro Tyr His Phe Asp Leu Glu Leu Val Ser Glu Gln Pro Asp
        35                  40                  45

Leu Asp Leu Glu Gly Leu Leu His Arg Gln Val Tyr Leu Gly Phe Asp
50                  55                  60

Asp Gln Gly His Gly Val His Gly Leu Val Tyr Arg Val Ala Gln Gly
65                  70                  75                  80

Asp Ser Gly Arg Arg Leu Thr Arg Tyr Gln Leu Thr Leu Val Pro Gln
                85                  90                  95

Leu Ala Tyr Leu Ala His Ser Ser His Gln Arg Ile Phe Gln His Lys
            100                 105                 110

Thr Val Pro Gln Ile Val Ala Gln Val Leu Glu Gly Gln Gly Ile Gln
        115                 120                 125

Ser Asp Arg Phe Glu Phe Arg Leu Ser Gly Ala Tyr Pro Glu Arg Glu
    130                 135                 140

Tyr Cys Val Gln Phe Gly Glu Thr Asp Leu Ala Phe Ile Gln Arg Leu
145                 150                 155                 160

Cys Ala Glu Leu Gly Ile His Tyr His Phe Gln His Ser Ala Glu Gly
                165                 170                 175

His Leu Leu Val Phe Gly Asp Asp Gln Thr Val Phe Ala Gln Pro Glu
            180                 185                 190

Gln Pro Thr Pro Tyr Thr Pro Gly Ser Gly Met Val Ala Asp Thr Pro
        195                 200                 205

Ala Ile Lys Arg Phe Ala Val Gln Val Gln Thr Arg Thr Thr Ala Val
    210                 215                 220

Asn Leu Arg Asp Tyr Asp Phe Arg Lys Pro Asn Leu Gly Leu Glu Ser
225                 230                 235                 240

Ala Val Ala Gly Glu Gln Leu Pro Met Leu Glu Thr Gln Asp Tyr Pro
                245                 250                 255

Gly His Phe Ser Asp Arg Ala His Gly Lys Tyr Leu Ala Gln Arg Gly
            260                 265                 270

Leu Glu Arg His Arg Ser Asp Tyr Arg Ile Ala His Gly Asn Gly Asp
        275                 280                 285

Glu Pro Ala Leu Ala Gly Gly Arg Phe Leu Arg Leu Ala Gly His Pro
    290                 295                 300

Arg Gly Asp Trp Asn Gly Leu Trp Leu Ala Thr His Val Thr His Glu
305                 310                 315                 320

Gly Lys Gln Pro Gln Val Leu Glu Glu Ala Val Thr Glu Val Ala Gly
                325                 330                 335

Gly Asp Phe Arg Gln Gly Tyr Arg Asn Asn Phe Ile Ala Ala Pro Trp
            340                 345                 350

Asp Val Ile Phe Arg Pro Leu Trp Thr Glu His Ala Arg Pro Val Ile
        355                 360                 365

Ser Gly Tyr Gln His Ala Val Val Thr Gly Pro Ala Asp Ser Glu Ile

```
                370              375              380
His Cys Asp Glu Tyr Gly Arg Val Lys Val Gln Leu Ala Trp Asp Arg
385                 390                 395                 400

Ala Gly Glu His Asn Asp His Ser Ser Cys Trp Leu Arg Val Ala Ser
                405                 410                 415

Gly Trp Ala His Asp Arg Tyr Gly Ser Val Leu Ile Pro Arg Val Gly
                420                 425                 430

Met Glu Val Leu Val Gly Phe Val Asn Gly Asp Met Asp Met Pro Leu
                435                 440                 445

Val Met Gly Cys Leu Pro Asn Ala Ala Thr Pro Gly Ala Pro Arg Pro
                450                 455                 460

Ala Gly Gly Gln Asp Pro Gln Tyr Leu Ala Gln Pro Glu Gln Pro Gly
465                 470                 475                 480

Arg Arg Trp Leu Gln Arg Ala Thr Tyr Arg Gly Pro Gln Gly Arg Arg
                485                 490                 495

Gly Asn Leu Pro Ala Arg Pro Ala Gly Leu Asp Ala Ala Cys Thr Ala
                500                 505                 510
```

<210> SEQ ID NO 38
<211> LENGTH: 2025
<212> TYPE: DNA
<213> ORGANISM: Pseudomonas fluorescens
<220> FEATURE:
<221> NAME/KEY: misc_feature
<223> OTHER INFORMATION: VgrG gene

<400> SEQUENCE: 38

```
atgttcgctc tgccaatca agtgccttt accctgtccc tcgacggtga gctcagtgaa      60
ctcaaggtgt cgagtttac gggccgtgaa tccatcagcc agccttacca ttttgatctc    120
gagttggtca gcgaacagcc cgatctcgac ctggaaggct tgctgcatcg ccaggtgtat    180
ctcgggttcg atgatcaggg ccatggtgtt catgggctgg tctaccgggt ggcgcagggc    240
gattccggac ggcgcctgac gcgttatcag ttgacgcttg gccgcagct ggcctatctg     300 gcgcacagca gccaccagcg cattttccag cacaagacgg tgccgcagat tgttgcgcag    360
gtactggagg ggcagggcat ccagagtgac cgcttcgaat ccggctcag cggtgcctac     420 cccgagcgcg agtattgtgt gcagtttggc gagactgacc tggcgttcat tcagcggctg    480
tgcgcggagt tgggcattca ctatcacttc cagcattcgg ccgaggggca tttgctggtg    540
tttggggatg accagacggt ctttgcccag cccgaacagc ccacgcctta caccccggt    600 tccgggatgg tggcggatac cccggcaatc aagcggtttg cggtgcaggt gcagacccgc    660
accacggctg tgaacctgcg cgattacgac tttcgcaagc cgaacctggg cctggaaagc    720
gcggtcgctg gcgagcagct tccgatgctt gaaacgcagg attaccccgg tcatttcagc    780
gaccgcgccc atggcaaata ccttgcgcag cgaggcctgg agcgtcatcg cagtgattac    840
cgcatcgccc atggcaacgg tgatgagccg gcattggccg gcggcaggtt cctcaggctg    900
gcgggccacc cacggggaga ctggaatggc ctgtggttgg cgacacacgt gacccacgag    960
ggtaaacaac cgcaagtcct ggaagaggct gtgaccgagg tcgccggtgg ggactttcgc   1020
cagggttatc gcaacaactt tattgccgcg ccgtgggacg tgattttccg cccgtctctg   1080
gacgagcatg cgcgcccagt gatctcgggt tatcaacatg ccgtggtgac cggccccgcc   1140
gacagtgaaa tccattgcga tgagtacggc cgggtcaagg tgcaactggc ctggaccgt   1200 gccggtgaac ataacgacca ttccagttgc tggctgaggg ttgccagtgg gtgggcgcat   1260
```

-continued

```
gatcgctatg gttcggtgct gatcccgcga gtcggcatgg aagtgctggt gggtttcgtc    1320
aatggcgaca tggacatgcc gttggtgatg ggctgtttgc ccaacgcggc gacccaggtg    1380
cccctcgacc tgccggcgga caagacccgc agtatcttgc gcagccagag cagcccgggc    1440
ggcggtggct acaacgagct acgtatcgag gaccgcaagg gcgccgagga aatttacctg    1500
cgcgcccagc gggattggac gcagcatgta ctgcatgatc aacaggtgca ggtcgataac    1560
gggcgtcgta tcaccgtggg tggcgagtcg caccatgagt tgcgcggtga agagcagcgc    1620
attacccacg gcaatcgtct gacgcagctc aagcaggatg atcacgtggt ggtcgccggt    1680
tcgcagcagg tgcgcgccga gcggactatt cagatagggg cagggcaaag cgtcgtcatt    1740
gatgcgggcg cgactgtcac gatccaggcg ggtgggcagt cgattacgct gtcggccggt    1800
gggattttca gcagtgtgcc gatccagctt ggcagctcgc ccgctccggc ggccgcaccg    1860
ttgatgcctg gcgtgaaaga gacgttactg gccgtgattc cggcgccgct gagccgtgtg    1920
caagtggcca gcttcaagcg tagcgcaccg ttttgcgaag agtgtgagcg ctgcaagaac    1980
ggccagtgcg atctcctccg acacagcaat gcaccccaac cttaa                   2025
```

<210> SEQ ID NO 39
<211> LENGTH: 674
<212> TYPE: PRT
<213> ORGANISM: Pseudomonas fluorescens
<220> FEATURE:
<221> NAME/KEY: MISC_FEATURE
<223> OTHER INFORMATION: VgrG protein

<400> SEQUENCE: 39

```
Met Phe Ala Pro Ala Asn Gln Ser Ala Phe Thr Leu Ser Leu Asp Gly
1               5                   10                  15

Glu Leu Ser Glu Leu Lys Val Phe Glu Phe Thr Gly Arg Glu Ser Ile
            20                  25                  30

Ser Gln Pro Tyr His Phe Asp Leu Glu Leu Val Ser Glu Gln Pro Asp
        35                  40                  45

Leu Asp Leu Glu Gly Leu Leu His Arg Gln Val Tyr Leu Gly Phe Asp
    50                  55                  60

Asp Gln Gly His Gly Val His Gly Leu Val Tyr Arg Val Ala Gln Gly
65                  70                  75                  80

Asp Ser Gly Arg Arg Leu Thr Arg Tyr Gln Leu Thr Leu Val Pro Gln
                85                  90                  95

Leu Ala Tyr Leu Ala His Ser Ser His Gln Arg Ile Phe Gln His Lys
            100                 105                 110

Thr Val Pro Gln Ile Val Ala Gln Val Leu Glu Gly Gln Gly Ile Gln
        115                 120                 125

Ser Asp Arg Phe Glu Phe Arg Leu Ser Gly Ala Tyr Pro Glu Arg Glu
    130                 135                 140

Tyr Cys Val Gln Phe Gly Glu Thr Asp Leu Ala Phe Ile Gln Arg Leu
145                 150                 155                 160

Cys Ala Glu Leu Gly Ile His Tyr His Phe Gln His Ser Ala Glu Gly
                165                 170                 175

His Leu Leu Val Phe Gly Asp Asp Gln Thr Val Phe Ala Gln Pro Glu
            180                 185                 190

Gln Pro Thr Pro Tyr Thr Pro Gly Ser Gly Met Val Ala Asp Thr Pro
        195                 200                 205

Ala Ile Lys Arg Phe Ala Val Gln Val Gln Thr Arg Thr Thr Ala Val
    210                 215                 220
```

```
Asn Leu Arg Asp Tyr Asp Phe Arg Lys Pro Asn Leu Gly Leu Glu Ser
225                 230                 235                 240

Ala Val Ala Gly Glu Gln Leu Pro Met Leu Glu Thr Gln Asp Tyr Pro
            245                 250                 255

Gly His Phe Ser Asp Arg Ala His Gly Lys Tyr Leu Ala Gln Arg Gly
        260                 265                 270

Leu Glu Arg His Arg Ser Asp Tyr Arg Ile Ala His Gly Asn Gly Asp
    275                 280                 285

Glu Pro Ala Leu Ala Gly Gly Arg Phe Leu Arg Leu Ala Gly His Pro
290                 295                 300

Arg Gly Asp Trp Asn Gly Leu Trp Leu Ala Thr His Val Thr His Glu
305                 310                 315                 320

Gly Lys Gln Pro Gln Val Leu Glu Glu Ala Val Thr Glu Val Ala Gly
            325                 330                 335

Gly Asp Phe Arg Gln Gly Tyr Arg Asn Asn Phe Ile Ala Ala Pro Trp
        340                 345                 350

Asp Val Ile Phe Arg Pro Ser Leu Asp Glu His Ala Arg Pro Val Ile
    355                 360                 365

Ser Gly Tyr Gln His Ala Val Val Thr Gly Pro Ala Asp Ser Glu Ile
370                 375                 380

His Cys Asp Glu Tyr Gly Arg Val Lys Val Gln Leu Ala Trp Asp Arg
385                 390                 395                 400

Ala Gly Glu His Asn Asp His Ser Ser Cys Trp Leu Arg Val Ala Ser
            405                 410                 415

Gly Trp Ala His Asp Arg Tyr Gly Ser Val Leu Ile Pro Arg Val Gly
        420                 425                 430

Met Glu Val Leu Val Gly Phe Val Asn Gly Asp Met Asp Met Pro Leu
    435                 440                 445

Val Met Gly Cys Leu Pro Asn Ala Ala Thr Gln Val Pro Leu Asp Leu
450                 455                 460

Pro Ala Asp Lys Thr Arg Ser Ile Leu Arg Ser Gln Ser Ser Pro Gly
465                 470                 475                 480

Gly Gly Gly Tyr Asn Glu Leu Arg Ile Glu Asp Arg Lys Gly Ala Glu
            485                 490                 495

Glu Ile Tyr Leu Arg Ala Gln Arg Asp Trp Thr Gln His Val Leu His
        500                 505                 510

Asp Gln Gln Val Gln Val Asp Asn Gly Arg Arg Ile Thr Val Gly Gly
    515                 520                 525

Glu Ser His His Glu Leu Arg Gly Glu Glu Arg Ile Thr His Gly
530                 535                 540

Asn Arg Leu Thr Gln Leu Lys Gln Asp Asp His Val Val Val Ala Gly
545                 550                 555                 560

Ser Gln Gln Val Arg Ala Glu Arg Thr Ile Gln Ile Gly Ala Gly Gln
            565                 570                 575

Ser Val Val Ile Asp Ala Gly Ala Thr Val Thr Ile Gln Ala Gly Gly
        580                 585                 590

Gln Ser Ile Thr Leu Ser Ala Gly Gly Ile Phe Ser Ser Val Pro Ile
    595                 600                 605

Gln Leu Gly Ser Ser Pro Ala Pro Ala Ala Pro Leu Met Pro Gly
610                 615                 620

Val Lys Glu Thr Leu Leu Ala Val Ile Pro Ala Pro Leu Ser Arg Val
625                 630                 635                 640

Gln Val Ala Ser Phe Lys Arg Ser Ala Pro Phe Cys Glu Glu Cys Glu
```

-continued

```
                645                 650                 655
Arg Cys Lys Asn Gly Gln Cys Asp Leu Leu Arg His Ser Asn Ala Pro
            660                 665                 670
Gln Pro
```

<210> SEQ ID NO 40
<211> LENGTH: 694
<212> TYPE: PRT
<213> ORGANISM: Vibrio cholera
<220> FEATURE:
<221> NAME/KEY: MISC_FEATURE
<223> OTHER INFORMATION: vgrG-2 gene product

<400> SEQUENCE: 40

```
Met Ala Thr Leu Ala Tyr Ser Ile Glu Val Glu Gly Leu Glu Asp Glu
1               5                   10                  15

Thr Leu Val Val Arg Gly Phe His Gly Gln Glu Pro Leu Ser Asn Ser
            20                  25                  30

Val Phe Leu Gly Gln Ala Cys Tyr Gly Phe Arg Tyr Glu Val Gln Leu
        35                  40                  45

Ala Ser Arg Val Ser Asn Leu Thr Ala Glu Gln Met Val Asp Lys Arg
    50                  55                  60

Ala Glu Leu Lys Ile Tyr Arg Asn Ser Gln Leu Val Gln Arg Val His
65                  70                  75                  80

Gly Ile Val Arg Ala Phe Ser Gln Gly Asp Ile Gly His His His Thr
                85                  90                  95

Phe Tyr Glu Leu Thr Leu Val Pro Ala Leu Glu Arg Leu Ser Leu Arg
            100                 105                 110

His Asn Ser Arg Ile Phe Gln Lys Gln Thr Val Pro Glu Ile Leu Ser
        115                 120                 125

Ile Leu Leu Gln Glu Met Gly Ile His Asp Tyr Ala Phe Ala Leu Lys
    130                 135                 140

Arg Asp Cys Val Gln Arg Glu Phe Cys Val Gln Tyr Arg Glu Ser Asp
145                 150                 155                 160

Ile Asp Phe Leu His Arg Leu Ala Ala Glu Glu Gly Leu Val Tyr Ser
                165                 170                 175

Phe Val His Glu Ala Gly Lys His Thr Leu Tyr Phe Ser Asp Ala Ser
            180                 185                 190

Asp Ser Leu Ser Lys Leu Pro Glu Pro Ile Pro Tyr Asn Ala Leu Ala
        195                 200                 205

Gly Gly Thr Met Asp Thr Pro Tyr Ile His Gly Leu Thr Tyr Arg Thr
    210                 215                 220

Gln Ala Glu Val Ser Glu Val Gln Leu Lys Asp Tyr Ser Phe Lys Lys
225                 230                 235                 240

Pro Thr Tyr Ser Phe Leu Gln Thr Val Gln Gly Thr Glu Leu Asp Tyr
                245                 250                 255

Gln Gln Thr Arg Tyr Gln His Phe Asp Ala Pro Gly Tyr Lys Asp
            260                 265                 270

Asp Val Asn Gly Ala Ala Phe Ser Gln Ile Arg Leu Asp Tyr Leu Arg
        275                 280                 285

Arg His Ala His Thr Ala Thr Gly Gln Ser Asn Glu Pro Leu Leu Arg
    290                 295                 300

Ala Gly Tyr Lys Phe Asp Leu Gln Glu His Leu Asp Pro Ala Met Asn
305                 310                 315                 320

Arg Asp Trp Val Val Val Ser Ile Asn His Gln Gly Glu Gln Pro Gln
```

```
                    325                 330                 335
Ala Leu Gln Glu Glu Gly Gly Ser Gly Ala Thr Thr Tyr Asn Asn Gln
                340                 345                 350
Phe Ser Leu Ile Pro Gly His Leu His Trp Arg Ala Glu Pro Gln Pro
            355                 360                 365
Lys Pro Gln Val Asp Gly Pro Met Ile Ala Thr Val Val Gly Pro Glu
        370                 375                 380
Gly Glu Glu Ile Phe Cys Asp Glu His Gly Arg Val Lys Ile His Phe
385                 390                 395                 400
Pro Trp Asp Arg Tyr Ser Asn Gly Asn Glu Gln Ser Ser Cys Trp Val
                405                 410                 415
Arg Val Ser Gln Gly Trp Ala Gly Ser Gln Tyr Gly Phe Ile Ala Ile
                420                 425                 430
Pro Arg Ile Gly His Glu Val Ile Val Ser Phe Leu Asn Gly Asp Pro
                435                 440                 445
Asp Gln Pro Ile Ile Thr Gly Arg Thr Tyr His Ala Thr Asn Thr Pro
            450                 455                 460
Pro Tyr Thr Leu Pro Glu His Lys Thr Lys Thr Val Leu Arg Thr Glu
465                 470                 475                 480
Thr His Gln Gly Glu Gly Phe Asn Glu Leu Ser Phe Glu Asp Gln Ala
                485                 490                 495
Gly Lys Glu Gln Ile Tyr Leu His Ala Gln Lys Asp Phe Asp Gly Leu
                500                 505                 510
Ile Glu Asn Asp His Thr Thr Val Ile Arg His Asp Gln His Leu Thr
            515                 520                 525
Val Glu Asn Asp Gln Phe Thr Gln Ile Lys His Asn Gln His Leu Thr
        530                 535                 540
Val Glu Gly Glu Ser Arg Thr Leu Val Lys Leu Asp Cys Ser Ser Glu
545                 550                 555                 560
Ile Gly Gly Ser Leu Gln Gln Lys Ile Gly Ser Lys Ala Ile Tyr Asp
                565                 570                 575
Ala Gly Thr Glu Val His Leu Lys Ala Gly Asn Lys Leu Val Leu Glu
                580                 585                 590
Ala Gly Asn Glu Leu Thr Ile Lys Ala Gly Gly Ser Phe Ile Lys Val
            595                 600                 605
Asp Ala Gly Gly Val His Val Val Gly Ser Ala Ile Asn Leu Asn Ser
        610                 615                 620
Gly Gly Ser Ala Gly Ser Gly Ser Tyr Gly Gly Lys Met Ala Glu
625                 630                 635                 640
Leu Pro Gln Gly Val Asp Lys Ala Lys Thr Pro Gln Glu Ile Glu Leu
                645                 650                 655
Ala Ala Val Thr Pro Thr Gln Gln Ser Met Ser Pro Leu Leu Lys Ala
                660                 665                 670
Arg Gln Ile Glu Ala Leu Lys Gly Pro Ala Pro Val Cys Glu Val Cys
            675                 680                 685
Glu Glu Ala Lys Gly Asn
    690
```